US010288610B2

(12) United States Patent
Charles et al.

(10) Patent No.: US 10,288,610 B2
(45) Date of Patent: May 14, 2019

(54) VITRO ASSAYS FOR DETECTING *SALMONELLA ENTERICA* SEROTYPE TYPHI

(71) Applicants: The General Hospital Corporation, Boston, MA (US); International Centre for Diarrhoeal Disease Research, Bangladesh (ICDDR,B), Dacca (BD); The Chancellor, Masters and Scholars of the University of Oxford, Oxford (GB)

(72) Inventors: Richelle Charles, Cambridge, MA (US); Edward T. Ryan, Wellesley, MA (US); Firdausi Qadri, Dacca (BD); Stephen Baker, Ho Chi Minh (VN)

(73) Assignees: THE GENERAL HOSPITAL CORPORATION, Boston, MA (US); INTERNATIONAL CENTRE FOR DIARRHOEAL DISEASE RESEARCH, BANGLADESH (ICDDR,B), Dacca (BD); THE CHANGELLOR, MASTERS AND SCHOLARS OF THE UNIVERSITY OF OXFORD, Oxford (GB)

(*) Notice: Subject to any disclaimer, the term of this patent is extended or adjusted under 35 U.S.C. 154(b) by 0 days.

(21) Appl. No.: 14/441,642

(22) PCT Filed: Nov. 12, 2013

(86) PCT No.: PCT/US2013/069571
§ 371 (c)(1),
(2) Date: May 8, 2015

(87) PCT Pub. No.: WO2014/078270
PCT Pub. Date: May 22, 2014

(65) Prior Publication Data
US 2015/0293093 A1 Oct. 15, 2015

Related U.S. Application Data

(60) Provisional application No. 61/725,755, filed on Nov. 12, 2012, provisional application No. 61/814,568, filed on Apr. 22, 2013.

(51) Int. Cl.
A61K 39/112 (2006.01)
A61K 39/02 (2006.01)
G01N 33/53 (2006.01)
G01N 33/569 (2006.01)
G01N 33/543 (2006.01)

(52) U.S. Cl.
CPC ... *G01N 33/56916* (2013.01); *A61K 39/0275* (2013.01); *G01N 33/54313* (2013.01); *G01N 2333/255* (2013.01); *G01N 2469/20* (2013.01)

(58) Field of Classification Search
CPC ........ A61K 39/00; A61K 39/02; A61K 39/04; A61K 39/0275

USPC ...... 424/184.1, 185.1, 234.1, 258.1; 435/7.1, 435/7.2
See application file for complete search history.

(56) References Cited

U.S. PATENT DOCUMENTS

| 6,610,836 | B1* | 8/2003 | Breton | C07K 14/26 435/320.1 |
|---|---|---|---|---|
| 6,747,137 | B1* | 6/2004 | Weinstock | C12Q 1/6895 435/6.13 |
| 7,041,814 | B1* | 5/2006 | Weinstock | C07K 14/265 435/252.3 |
| 2003/0148324 | A1* | 8/2003 | Bingen | C07K 14/245 435/6.15 |
| 2004/0029129 | A1* | 2/2004 | Wang | C07K 14/195 435/6.18 |
| 2007/0292927 | A1* | 12/2007 | Donaldson | C12N 9/0006 435/160 |
| 2008/0038250 | A1* | 2/2008 | Zlatkin | C07K 14/44 424/130.1 |
| 2010/0087373 | A1 | 4/2010 | Yang et al. | |
| 2010/0323343 | A1 | 12/2010 | Egan et al. | |
| 2014/0356389 | A1* | 12/2014 | Masignani | A61K 39/0258 424/190.1 |

OTHER PUBLICATIONS

Lienau, E.K., et al. The New England Journal of Medicine, vol. 364, pp. 981-982, 2011.*
Baars, L., et al. , Journal of Biological Chemistry, vol. 281, No. 15, pp. 10024-10034, 2006.*
Lienau et al., New England Journal of Medicine, vol. 364:981-982, 2011.*
Boyd et al., "Differences in Gene Content among *Salmonella enterica sevorar typhi* Isolates", Journal of Clinical Microbiology, 41(8):3823-3828 (2003).
Charles et al., "Characterization of Anti-*Salmonella enterica serotype typhi* Antibody Responses in Bacteremic Bangladeshi Patients by an Immunoaffinity Proteomics-Based Technology", Clinical and Vaccine Immunology, vol. 17 No. 8: pp. 1188-1195 (2010).
Charles et al., "Identification of Immunogenic *Salmonella enterica serotype typhi* Antigens Expressed in Chronic Biliary Carriers of *S. typhi* in Kathmandu, Nepal", PLOS Neglected Tropical Diseases, 7(8):e2335 (2013).
Rodas et al., "*Salmonella enterica sevorar typhi* has a 4.1 kb genetic island inserted within the sapABCDF operon that causes loss of resistance to the antimicrobial peptide protamine", J. Antimicrob Chemother, 65:1624-1630 (2010).

(Continued)

Primary Examiner — Rodney P Swartz
(74) Attorney, Agent, or Firm — Nixon Peabody LLP

(57) ABSTRACT

Provided are assays, kits and compositions for testing subjects, particularly asymptomatic subjects, to ascertain whether or not they are carriers of *Salmonella enterica* serotype *Typhi*. Methods for detecting the presence of *Salmonella enterica* serotype *Typhi* indicating molecules by a variety of methods such as immunoassays and mass spectrometry also are provided.

1 Claim, 3 Drawing Sheets
Specification includes a Sequence Listing.

(56) References Cited

OTHER PUBLICATIONS

Harris et al. "Identification of in vivo-induced bacterial protein antigens during human infection with *Salmonella anterica serovar typhi*." Infection and Immunity 74(9):5161-5168 (2006).

Losonsky et al., "Development and evaluation of an enzyme-linked immunosorbent assay for serum Vi antibodies for detection of chronic *Salmonella typhi* carriers." Journal of Clinical Microbiology 25(12):2266-2269 (1987).

Nolan et al. "Evaluation of a new assay for Vi antibody in chronic carriers of *Salmonella typhi*." Journal of Clinical Microbiology 12(1):22-26 (1980).

* cited by examiner

VITRO ASSAYS FOR DETECTING *SALMONELLA ENTERICA* SEROTYPE *TYPHI*

CROSS-REFERENCE TO RELATED APPLICATIONS

This application is a 35 U.S.C. § 371 National Phase Entry Application of International Application No. PCT/US13/69571 filed Nov. 12, 2013, and which claims benefit under 35 U.S.C. § 119(e) of U.S. Provisional Application No. 61/725,755 filed Nov. 13, 2012 and of U.S. Provisional Application No. 61/814,568 filed Apr. 22, 2013, the contents of each of which are incorporated herein by reference in their entireties.

GOVERNMENT SUPPORT

This invention was made with Government support under Grant Number AI100023 awarded by the National Institute of Health. The Government has certain rights to this invention.

SEQUENCE LISTING

The instant application contains a Sequence Listing which has been submitted electronically in ASCII format and is hereby incorporated by reference in its entirety. Said ASCII copy, created on Nov. 11, 2013, is named 030258-075872-PCT_SL.txt and is 58,121 bytes in size.

BACKGROUND

Field of the Invention

The present invention relates to in vitro assays, kits and methods for identifying *Salmonella enterica* serotype *Typhi* in a biological sample, for example, in a biological sample taken from an asymptomatic human subject.

Background of the Invention

*Salmonella enterica* serotype *Typhi* (*S. Typhi*) is a human-specific pathogen. It is the cause of typhoid fever and the predominant cause of enteric fever with S. Paratyphi A. Enteric fever affects over 21 million people each year, resulting in 200,000 deaths [Crump J A, Luby S P, Mintz E D (2004) The global burden of typhoid fever. Bull World Health Organ 82: 346-353]. A small percentage of *S. Typhi* (and S. Paratyphi A) infected individuals go on to develop a chronic but asymptomatic infection in the biliary tract that can persist for decades [Gonzalez-Escobedo G, Marshall J M, Gunn J S (2011) Chronic and acute infection of the gall bladder by *Salmonella Typhi*: understanding the carrier state. Nat Rev Microbiol 9: 9-14]. Since *S. Typhi* and *S. Paratyphi* A are human-restricted pathogens, chronic carriers may act as a reservoir of infection within a community. The carriers may contribute to transmission of infection through intermittent shedding of bacteria in feces, especially in areas of low transmission, and they may act as vehicles for introducing *S. Typhi* and *S. Paratyphi* A into previously uninfected communities. Correctly identifying asymptomatic chronic carriers could be critical for disease control.

Little is known about host-pathogen interactions in the biliary tract of chronic carriers, and there is currently no reliable diagnostic assay to identify asymptomatic *S. Typhi* and *S. Paratyphi* A carriage. The use of the bacterial culture of stool is challenging due to the expense and logistics of obtaining multiple samples from patients since shedding is typically at low level and intermittent. Measurement of antibody responses to the *S. Typhi* capsular Vi antigen has been previously evaluated as a method to detect chronic *S. Typhi* carriers [Nolan C M, Feeley J C, White P C, Jr, Hambie E A, Brown S L, et al (1980) Evaluation of a new assay for Vi antibody in chronic carriers of *Salmonella typhi*. J Clin Microbiol 12: 22-26; Parry C M, Wijedoru L, Arjyal A, Baker S (2011) The utility of diagnostic tests for enteric fever in endemic locations. Expert Rev Anti Infect Ther 9: 711-725; Losonsky G A, Ferreccio C, Kotloff K L, Kaintuck S, Robbins J B, et al (1987) Development and evaluation of an enzyme-linked immunosorbent assay for serum Vi antibodies for detection of chronic *Salmonella typhi* carriers. J Clin Microbiol 25: 2266-2269; Nath G, Mauryal P, Gulati A K, Singh T B, Srivastava R, et al (2010) Comparison of Vi serology and nested PCR in diagnosis of chronic typhoid carriers in two different study populations in typhoid endemic area of India. Southeast Asian J Trop Med Public Health 41: 636-640]. In Chile, anti-Vi antibody responses had a sensitivity of 75% and specificity of 92%-97% for *S. Typhi* carriage [Lanata C F, Levine M M, Ristori C, Black R E, Jimenez L, et al (1983) Vi serology in detection of chronic *Salmonella typhi* carriers in an endemic area. Lancet 2: 441-443]. However, due to a low prevalence rate of carriage in the general population its positive predictive value was only 8-17%. In Vietnam, a large community based survey for anti-Vi antibodies demonstrated a 3% positivity rate in the population; however, *S. Typhi* was never detected in the stool of individuals identified by anti-Vi screening [Gupta A, My Thanh N T, Olsen S J, Sivapalasingam S, My Trinh T T, et al (2006) Evaluation of community-based serologic screening for identification of chronic *Salmonella typhi* carriers in Vietnam. Int J Infect Dis 10: 309-314].

SUMMARY

We have identified a novel set of biomarkers to indicate *S. Typhi* from a sample taken from an asymptomatic human subject. These markers can be used to identify, for example, *S. Typhi* can identified by assaying immunoglobulins in the sample that are specific for these biomarkers, or antigenic fragments thereof or by direct analysis of the antigens by antigen-specific antibodies from the biological sample.

The identification of *S. Typhi* in a biological sample is useful, for example, in classifying asymptomatic humans as *S. Typhi* carriers and as *S. Typhi* non-carriers, which can be used in identifying individuals or households for using particularly stringent hygienic standards for preventing spreading S. *Typhi* infection by asymptomatic carrier individuals. The classification can also assist hospitals in determining allocating space for humans who are asymptomatic carriers for *S. Typhi* and separating such humans from subjects whose condition poses a particular risk of contracting *S. Typhi* whether from a symptomatic or asymptomatic but *S. Typhi* positive human contact.

The novel set of biomarkers comprises STY1364; STY2657; HCM2.0069c; HCM2.0043; HCM1.137; STY2386; STY1479; STY2454; STY2248; STY3709; STY2155; HCM1.213c; and STY0712. One can detect the presence of immunoglobulins against any one of these biomarkers or any combination thereof.

Accordingly, we provide methods, compositions, assays and kits which are designed to detect, e.g., immunoglobulins against these specific biomarkers or presence of these specific biomarkers in a biological sample. The biomarkers are particularly useful for in vitro analysis of biological samples, for example from asymptomatic humans to detect whether, e.g., immunoglobulins against *S. Typhi* or the biomarkers are present in the sample or not.

Accordingly, we provide an in vitro assay for identifying *Salmonella enterica* serotype *Typhi* (*S. Typhi*) in a biological sample taken from an asymptomatic human subject comprising: contacting at least one antigen selected from: STY1479; STY1364; STY2657; HCM2.0069c; HCM2.0043; HCM1.137; STY2386; STY2454; STY2248; STY3709; STY2155; HCM1.213c; and STY0712 or one or more fragments thereof or a combination thereof with the biological sample to form an antigen-sample mixture; (a) contacting the antigen-sample mixture with a labeled human immunoglobulin-specific antibody to form a labeled antigen-immunoglobulin complex; (b) detecting presence of the labeled antigen-immunoglobulin complex, and if/when the labeled antigen-immunoglobulin complex is present then identifying *Salmonella enterica* serotype *Typhi* in the biological sample.

In some aspects of all the embodiments of the invention, the in vitro assay can further comprise detecting the amount of the immunoglobulin-antigen complex and comparing the amount of the immunoglobulin-antigen complex to a reference value and if the amount of the immunoglobulin-antigen complex is higher than the reference value, then identifying the biological sample as comprising *Salmonella enterica* serotype *Typhi*.

In some aspects of all the embodiments of the invention, the step of detecting can be performed by a non-human machine.

In some aspects of all the embodiments of the invention, the step of comparing can performed by a non-human medium.

In some aspects of all the embodiments of the invention, the at least one biomarker comprises biomarker STY 1479.

In some aspects of all the embodiments of the invention, the at least one biomarker is STY 1479.

We also provide an in vitro assay comprising a solid surface comprising no more than 20 probe sets for a biomarker wherein the no more than 20 probe sets comprise at least one of the proteins selected from: STY1364; STY2657; HCM2.0069c; HCM2.0043; HCM1.137; STY2386; STY1479; STY2454; STY2248; STY3709; STY2155; HCM1.213c; STY0712 and one or more fragments thereof.

In some aspects of all the embodiments of the invention, the assay further comprises a positive and a negative control.

In some aspects of all the embodiments of the invention, the solid surface comprises no more than 15 probe sets.

In some aspects of all the embodiments of the invention, the probe sets comprise at least STY1479.

In some aspects of all the embodiments of the invention, the solid surface consists essentially of a probe set for STY1479 and a positive and a negative assay control comprising a human immunoglobulin.

We further provide an in vitro assay for identifying *Salmonella enterica* serotype *Typhi* in a biological sample taken from an asymptomatic human subject comprising: (a) contacting the biological sample with a labeled antibody against at least one or any combination of the biomarkers selected from: STY1364; STY2657; HCM2.0069c; HCM2.0043; HCM1.137; STY2386; STY1479; STY2454; STY2248; STY3709; STY2155; HCM1.213c; and STY0712 to form an antibody-biomarker complex; (b) detecting the antibody-biomarker complex and if/when the antibody-biomarker complex is detected, then identifying *Salmonella enterica* serotype *Typhi* in the biological sample.

In some aspects of all the embodiments of the invention, the assay further comprises detecting the amount of the antibody-biomarker complex and comparing the amount of the antibody-biomarker complex to a reference value and if the amount of the antibody-biomarker complex is higher than the reference value, then identifying the biological sample as comprising *Salmonella enterica* serotype *Typhi*.

In some aspects of all the embodiments of the invention, the step of detecting is performed by a non-human machine.

In some aspects of all the embodiments of the invention, the step of comparing is performed by a non-human medium.

In some aspects of all the embodiments of the invention, the at least one biomarker comprises biomarker STY 1479.

In some aspects of all the embodiments of the invention, the at least one biomarker is STY 1479.

We also provide an in vitro assay comprising a solid surface comprising no more than 20 probes for a biomarker wherein the no more than 20 probes comprise at least one of the biomarkers selected from: STY1364; STY2657; HCM2.0069c; HCM2.0043; HCM1.137; STY2386; STY1479; STY2454; STY2248; STY3709; STY2155; HCM1.213c; and STY0712.

In some aspects of all the embodiments of the invention, the assay further comprises a positive and a negative control probe.

In some aspects of all the embodiments of the invention, the solid surface comprises no more than 15 probes.

In some aspects of all the embodiments of the invention, the solid surface comprises a probe for detecting at least biomarker STY1479.

In some aspects of all the embodiments of the invention, the solid surface consists essentially a probe for detecting biomarker STY1479 and a positive and a negative assay control.

We further provide a test strip for detecting the presence of a *Salmonella enterica* serotype *Typhi* indicating molecule in a sample, comprising: a non-specific binding region; and an analyte binding region comprising at least one first binding partner immobilized thereon, wherein the at least one first binding partner is selected from an antigen selected from proteins STY1364; STY2657; HCM2.0069c; HCM2.0043; HCM1.137; STY2386; STY1479; STY2454; STY2248; STY3709; STY2155; HCM1.213c; and STY0712 or one or more fragments thereof; wherein the analyte binding region is downstream of the sample fluid flow pathway relative to the non-specific binding region.

In some aspects of all the embodiments of the invention, the test strip further comprises: a conjugate pad, which serves as a sample application component; an absorbent pad, which serves to draw the sample continuously through the device, wherein the materials of the membrane system form a single fluid flow pathway; and a porous or bibulous member in fluid communication with the absorbent pad and conjugate pad, which porous or bibulous member accommodates a liquid sample and contains the analyte binding region.

In some aspects of all the embodiments of the invention, the test strip further comprises: a mobilization region containing a second binding partner, wherein: the second binding partner is mobilized upon contact with the sample; and the mobilization region is upstream of the analyte binding region.

In some aspects of all the embodiments of the invention, the test strip further comprises: a control region containing a biomolecule that specifically binds the second biomarker binding partner, wherein: the control region is downstream of the analyte binding region.

In some aspects of all the embodiments of the invention, the non-specific binding region contains a non-specific binding protein immobilized thereon; and the non-specific binding protein is selected from among BSA, methylated BSA, W632 and mouse IgG.

In some aspects of all the embodiments of the invention, the test strip can further comprise non-specific binding components to reduce the background, and positive and negative control zones or probes for standardization markers, such as creatinine.

We also provide a kit comprising at least one antigen selected from STY1364; STY2657; HCM2.0069c; HCM2.0043; HCM1.137; STY2386; STY1479; STY2454; STY2248; STY3709; STY2155; HCM1.213c; STY0712 and any fragment or combination thereof optionally bound to a solid surface; a positive control corresponding to at least one human immunoglobulin; and at least one antibody against at least one human immunoglobulin.

In some aspects of all the embodiments of the invention, the antigen is STY 1479.

In some aspects of all the embodiments of the invention, the kit comprises no more than 20 antigen sets directed to no more than 20 biomarkers.

In some aspects of all the embodiments of the invention, the kit comprises no more than 10 antigen sets directed to no more than 10 biomarkers. It can also comprise no more than 9, 8, 7, 6, 5, 4, 3, or 2 S. Typhi antigen sets directed to no more than 9, 8, 7, 6, 5, 4, 3, or 2 S. Typhi biomarkers. One antigen set may comprise a plurality of same antigen fragment or a plurality of different antigen fragments against one biomarker and still be considered an "antigen set" against one biomarker.

In some aspects of all the embodiments of the invention, the kit can further comprise non-specific binding components to reduce the background, and positive and negative control zones or probes for standardization markers, such as creatinine.

In some aspects of all the embodiments of the invention, the at least one human immunoglobulin comprises IgG.

We provides a kit comprising at least one probe that is specific for a biomarker selected from STY1364; STY2657; HCM2.0069c; HCM2.0043; HCM1.137; STY2386; STY1479; STY2454; STY2248; STY3709; STY2155; HCM1.213c; and STY0712; a positive control corresponding to the biomarker selected from STY1364; STY2657; HCM2.0069c; HCM2.0043; HCM1.137; STY2386; STY1479; STY2454; STY2248; STY3709; STY2155; HCM1.213c; and STY0712; and a negative biological sample that does not comprise any one of the biomarkers STY1364; STY2657; HCM2.0069c; HCM2.0043; HCM1.137; STY2386; STY1479; STY2454; STY2248; STY3709; STY2155; HCM1.213c; or STY0712.

In some aspects of all the embodiments of the invention, the kit consists essentially of a probe that is specific for biomarker STY1479, and a positive control comprising STY1479. The kit can further comprise non-specific binding components to reduce the background, and positive and negative controls or probes for standardization markers, such as creatinine.

We also provide a method for treatment of S. Typhi infection in an asymptomatic human subject comprising the steps of (a) detecting S. Typhi infection from a biological sample taken from the asymptomatic human subject by detecting the presence of at least one immunoglobulin specific for a biomarker selected from STY1364; STY2657; HCM2.0069c; HCM2.0043; HCM1.137; STY2386; STY1479; STY2454; STY2248; STY3709; STY2155; HCM1.213c; or STY0712; and if the at least one immunoglobulin specific for the biomarker is detected then administering to the subject an antibiotic effective against S. Typhi; if the at least one biomarker is not detected then not administering the antibiotic to the human subject.

We provide a microfluidic device comprising at least one S. Typhi specific antigen selected from the group consisting of STY1364; STY2657; HCM2.0069c; HCM2.0043; HCM1.137; STY2386; STY1479; STY2454; STY2248; STY3709; STY2155; HCM1.213c; or STY0712 and any combination or fragment thereof.

We provide a composition comprising no more than 20 different antigen sets selected from STY1364; STY2657; HCM2.0069c; HCM2.0043; HCM1.137; STY2386; STY1479; STY2454; STY2248; STY3709; STY2155; HCM1.213c; STY0712 and fragments thereof and a solid support. The device can further comprise non-specific binding components to reduce the background, and positive and negative control zones or probes for standardization markers, such as creatinine.

In some aspects of all the embodiments of the invention, the composition comprises no more than 10 different antigen sets. In some aspects of all the embodiments of the invention, the compositions comprises no more than 9, 8, 7, 6, 5, 4, 3, 2, or 1 S. Typhi biomarker-specific antigen set.

We provide a composition comprising at least one antibody against an isolated S. Typhi antigen selected from the group consisting of STY1364; STY2657; HCM2.0069c; HCM2.0043; HCM1.137; STY2386; STY1479; STY2454; STY2248; STY3709; STY2155; HCM1.213c; or STY0712 and any combination thereof.

DETAILED DESCRIPTION OF THE INVENTION

Figure 1A:
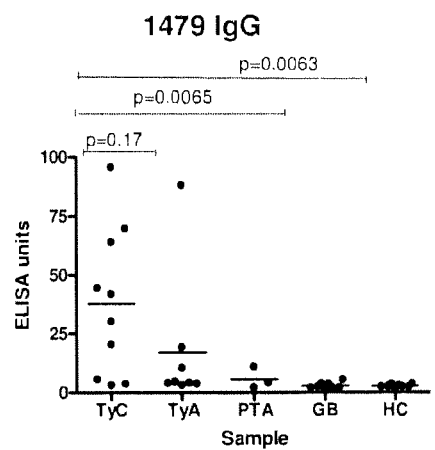
FIGS. 1A-1B show anti-STY1479 IgG (FIG. 1A) and IgA (FIG. 1B) responses in S. Typhi Carriers (TyC), Convalescent Acute Typhoid Patients (TyA), S. Paratyphi A Carriers (PTA), Nepalese controls undergoing elective cholestecomy with negative bile cultures (GB), and Healthy Bangladeshi controls (HC).
Figure 1B:
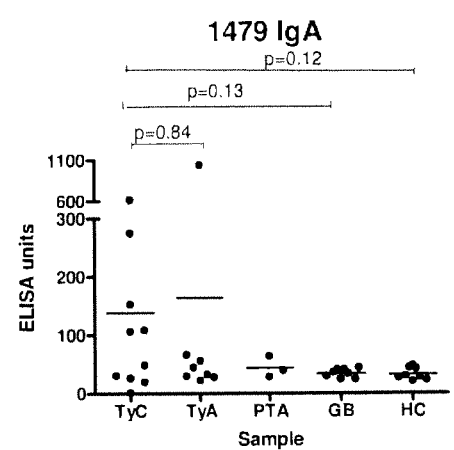
Figure 2A:
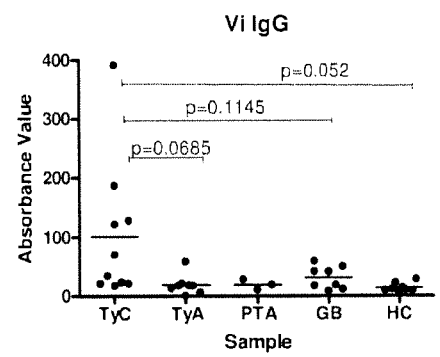
FIGS. 2A-2B show anti-Vi Antigen IgG (FIG. 2A) and IgA (FIG. 2B) responses were evaluated in S. Typhi Carriers (TyC), Convalescent Acute Typhoid Patients (TyA), S. Paratyphi A Carriers (PTA), Nepalese controls undergoing elective cholestecomy with negative bile cultures (GB), and Healthy Bangladeshi controls (HC).
Figure 2B:
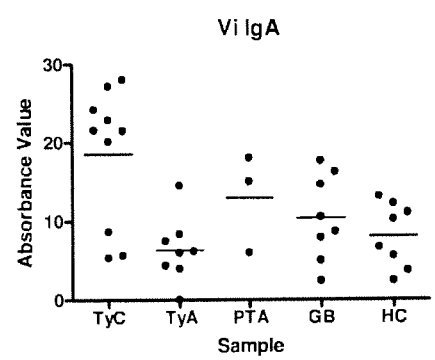

We describe a novel method of detecting the presence of Salmonella enterica serotype Typhi (S. Typhi) in a biological sample, in vitro, by detection of the presence of one or more surrogate biomarkers that we have discovered being associated with the presence of S. Typhi, particularly in a sample from an asymptomatic human who serves as a carrier of S. Typhi and that are absent in a human individual who is not a carrier of S. Typhi. The novel biomarkers associated with the presence of S. Typhi provide a significant improvement in the detection of asymptomatic carriers compared to the methods previously described, which can lead to improved treatment of the carriers and improvement in containing spread of S. Typhi in communities through the asymptomatic carriers.

Salmonella enterica serotype Typhi can colonize and persist in the biliary tract of infected individuals. This can result in an asymptomatic chronic carrier state, and chronic carriers may be persistent reservoirs of infection within a community and may introduce infection to new communities. Unfortunately, little is known about host-pathogen interactions in the biliary tract of chronic carriers, and there is currently no reliable diagnostic assay to identify asymptomatic *S. Typhi* carriers.

To study host-pathogen interactions in the biliary tract, we applied an immunoscreening technique called in vivo-induced antigen technology (IVIAT), to identify potential biomarkers unique to *S. Typhi* chronic carriers. IVIAT identifies humorally immunogenic bacterial antigens expressed uniquely in the in vivo environment, and we hypothesized that *S. Typhi* surviving in the biliary tract of humans may express a distinct proteomic profile. Thirteen *S. Typhi* antigens that were immunoreactive in carriers, but not in healthy individuals from a typhoid endemic area were identified. The identified antigens included a number of putative membrane proteins, lipoproteins, and hemolysin-related proteins.

YncE (STY1479), an uncharacterized protein with an ATP-binding motif, gave prominent responses in our screen. The response to YncE in patients whose biliary tract contained *S. Typhi* was compared to responses in patients whose biliary tract did not contain *S. Typhi*, patients with acute typhoid fever, and healthy controls residingin a typhoid endemic area. Seven of 10 (70%) chronic carriers, 0 of 8 bile culture-negative controls (0%), 0 of 8 healthy Bangladeshis (0%), and 1 of 8 (12.5%) Bangladeshis with acute typhoid fever had detectable anti-YncE IgG in blood. IgA responses were also present.

Therefore, we provide assays to measure the immune response, including detecting the presence of immunoglobulins, such as IgG, IgA, or IgM against these specific biomarkers or antigens we have discovered.

The invention is based, at least in part, on our discovery of a particular proteomic profile comprising biomarkers that are present in biological samples or antibodies against which are present in the biological samples from asymptomatic carriers of *S. Typhi* but not present in non-carriers. The proteomic profile comprises, consists essentially of or consists of the following biomarkers: STY1364; STY2657; HCM2.0069c; HCM2.0043; HCM1.137; STY2386; STY1479; STY2454; STY2248; STY3709; STY2155; HCM1.213c; and STY0712. Detecting one or more of the antibodies against these proteins or one or more of the proteins of this profile, one can detect presence of *S. Typhi* in an in vitro biological sample.

We generated a 120,000 clone genomic inducible expression library of *S. Typhi* CT18 (500-1500 bp fragments) in *E. coli* BL21DE3, and screened the library against pooled sera of patients, pre-adsorbed with in vitro grown *S. Typhi* and *E. coli* BL21DE3, who had bile cultures positive for *S. Typhi* at the time of elective cholecystectomy. We identified and sub-cloned 268 genes of interest from our primary screen. We identified 50 proteins that are immunoreactive in *S. Typhi* carriers. Of these, 13, namely STY1364; STY2657; HCM2.0069c; HCM2.0043; HCM1.137; STY2386; STY1479; STY2454; STY2248; STY3709; STY2155; HCM1.213c; and STY0712 are not immunoreactive in healthy individuals from a typhoid endemic area (Dhaka, Bangladesh).

Based on our findings, we can now provide assays to identify the presence or absence of antibodies against the specific *S. Typhi* proteins we discovered, wherein one or more of the newly identified biomarkers or antigens, or fragments thereof, is contacted with a biological sample. Any antigen-immunoglobulin complex that is formed as a result of the contact can then be detected by an antibody against the immunoglobulin.

The 13 identified proteins included a number of putative membrane proteins, lipoproteins, and hemolysin-related proteins (Table 1). YncE (or STY1479), a possible ATP-binding protein, had the overall highest differential immunoreactivity compared to healthy endemic-zone control sera in our immunoblot assay.

Therefore, we also provide methods of using anti-YncE serum responses as a diagnostic biomarker for asymptomatic *S. Typhi* carriage. To further characterize whether the immunoreactivity to YncE in *S. Typhi* carriers was specific, we also evaluated the immunoreactivity to YncE using sera of 5 groups of individuals: (1)*S. Typhi* carriers, (2) patients at the acute and convalescent phase of typhoid fever, (3)*S. Paratyphi* A carriers, (4) individuals who underwent cholecystectomy in Nepal whose bile cultures were negative for any pathogen, and (5) healthy controls from a typhoid endemic area (Dhaka, Bangladesh).

We found significantly higher IgG immunoreactivity to YncE in *S. Typhi* carriers compared to bile culture-negative patients (p=0.0205), healthy Bangladeshis (p=0.0005), and patients at the acute and convalescent phases of typhoid infection (p=0.0044 and p=0.0266, respectively); there was a trend toward statistical significance when compared to *S. Paratyphi* A carriers (p=0.22) (FIG. 1A). Of the 10 *S. Typhi* carriers, 7 (70%) had an anti-YncE IgG response (ELISA unit >100). None of 8 bile culture negative controls (0%), 0 of 8 healthy Bangladeshis (0%), 0 of 3 *S. Paratyphi* A carriers (0%) and 1 of 8 (12.5%) Bangladeshis at the acute and convalescent phase of *S. Typhi* had an anti-YncE IgG response. Thus, in our small subset of patients, using a cut-off value of >100 Elisa Units (EU), anti-YncE IgG had a sensitivity of 70%, and specificity of 100% when using endemic zone healthy individuals and cholecystectomy patients without detectable *S. Typhi* as controls. The specificity decreased to 95% if we included patients with acute typhoid fever.

*S. Typhi* carriers also had a higher IgA immunoreactivity to YncE compared to our two control groups: bile culture-negative patients (p=0.2370) and healthy Bangladeshis (p=0.2031) (FIG. 3B).

The trending higher anti-YncE IgA levels in *S. Typhi* carriers than in control groups, that information could support a salivary diagnostic to facilitate community-based screening for carriage.

For example, in our analysis, using a cut-off value of >100 EU of anti YncE IgG and/or >20 EU anti-Vi IgA, we could identify 9 out 10 *S. Typhi* carriers. There was no added benefit seen when pairing anti-YncE responses with anti-Vi IgG. Another potential pairing could include a marker of biliary tract inflammation such as elevated bilirubin values, since *S. Typhi* carriage is often associated with chronic inflammation of the gallbladder [Gonzalez-Escobedo G, Marshall J M, Gunn J S (2011) Chronic and acute infection of the gall bladder by *Salmonella Typhi*: understanding the carrier state. Nat Rev Microbiol 9: 9-14].

Accordingly, in some aspects, the invention provides a salivary diagnostic to detect higher IgA and/or IgG immunoreactivity to purified YncE protein. The assay can further include detecticng anti-Vi IgG and/or a marker for biliary tract inflammation, such as elevated bilirubin values to detect an *S. Typhi* carrier. The assay can be, for example, an ELISA based assay.

For example, plates can be coated with about 50-200, such as 100 ng/well of YncE and then patient sera is added at about 1:100-1:500, such as 1:200 dilution. Bound antibody was detected with anti-human IgG or IgA conjugated with horseradish peroxidase (Jackson Laboratories, Bar Harbor, Me.) at a 1:1000 dilution, and peroxidase activity was measured with the substrate 2,2-azinobis (ethylbenzthiazolinesulfonic acid). One of ordinary skill in the art can easily substitute the anti-human IgG and IgA conjugation with other detectable labels than horseradish peroxidase, such as fluorescent labels.

In our example, to compare across plates, readings of samples was divided by readings of an in-house pooled standard, multiplied by 100, and results were expressed as ELISA units (EU). One can further use, e.g., the Mann-Whitney U test, or another equivalent test to compare differences between groups. Other well-known techniques can be used to standardize the results across the plates.

For evaluation of anti-Vi IgG and IgA responses, ELISA plates can be coated with, e.g., 50-500 ng/well, e.g., 200 ng/well of Vi antigen (Sanofi Pasteur, Lyon, France). The above sera were applied at a 1:100 dilution, but other dilutions may also be used, such as 1:50 to 1:500 dilutions, and bound antibody can be detected with anti-human IgG and IgA conjugated, e.g., with horseradish peroxidase at, for example, a 1:1000 dilution. Peroxidase activity was measured with the substrate 2,2-azinobis (ethylbenzthiazolinesulfonic acid). One can further assess the differences between groups using, e.g., the Mann-Whitney U test or other equivalent test.

In some aspects, the immunoglobulin assays of the present invention measure the presence or absence or the immunoglobulins or antibodies, and in some aspects, the assays of the invention measure the amount of immunoglobulins, or antibodies, in the biological sample.

The body makes different immunoglobulins. The five known subclasses of antibodies include IgA, IgG, IgM, IgE, and IgD.

Immunoglobulin A (IgA), is typically found in high concentrations in the mucous membranes, particularly those lining the respiratory passages and gastrointestinal tract, as well as in saliva and tears. Thus, saliva can be used as a biological material on the methods of the invention.

Immunoglobulin G (IgG), is the most abundant type of antibody, and it is found in all body fluids and protects against bacterial and viral infections. IgG comprises at least four subclasses, namely IgG1, IgG2, IgG3, and IgG4, and any one of them or any combination of them can be used in the assays of the invention.

Immunoglobulin M (IgM), is found mainly in the blood and lymph fluid, is the first to be made by the body to fight a new infection.

Immunoglobulin E (IgE), is associated mainly with allergic reactions (when the immune system overreacts to environmental antigens such as pollen or pet dander). It is found in the lungs, skin, and mucous membranes.

Immunoglobulin D (IgD), exists in minute amounts in the blood. While it is the least understood antibody, it is possible that also IgD can be used in the assays of the invention.

Thus, in the assays of the invention, to detect any one or more antigen-immunoglobulin complex, one can use a secondary antibody against IgA, IgG, IgM, IgE, and IgD or any subclass thereof. For example, IgA, IgG, and IgM are frequently measured simultaneously.

The assays are tailored to the specific sample source. For example, IgA is particularly present in saliva and tears, and thus if saliva or tears are used as the biological sample in the assays of the invention, then IgA can be a good immunoglobulin to add to the at least one immunoglobulins used to detect the biomarkers. Similarly, if a stool sample or urine sample is used, one can select IgG as one of the immunoglobulins to be detected.

In the present invention the terms "antibody" and "immunoglobulin" are used interchangeably.

We discovered a specific set of antigens that are indicative of asymptomatic *S. Typhi* infection the in the sample. The body produces antibodies against these biomarkers and thus they can be detected using detection of biomarker- or antigen-specific immunoglobulins.

Several immunodiagnostic methods based on detection of antigen-antibody complexes can be used for detecting *S. Typhi* according to the present invention. Examples of methods include ELISA, immunofluorescence, Western blot, immunodiffusion, immunoelectrophoresis, and magnetic immunoassay, just to name a few. Any one of these methods can be used when combined with a reagent specific for one or any combination or all of the *S. Typhi* biomarkers which we have discovered. For example, we showed that in an ELISA assay format a significantly higher IgG immunoreactivity was detected to, for example, STY1479 in *S. Typhi* carriers compared to bile culture-negative patients (p<0.0065) and healthy Bangladeshis (p<0.0063). One can similarly measure other immunoglobulins using any one or a combination of the biomarkers of the invention.

Table below sets fort examples of possible combinations of the biomarkers that can be used in the assays and combined into the kits and detection or diagnostic strips of the invention. Immunoglobulins against any one of these antigens or any combination thereof can be analyzed using the proteins or antigenic fragments or epitopes thereof.

|  | STY 2657 | HCM 2.0069c | HCM 2.0043 | HCM 1.137 | STY 2386 | STY 1479 | STY 2454 | STY 2248 | STY 3709 | STY 2155 | HCM 1.213c | STY 0712 |
|---|---|---|---|---|---|---|---|---|---|---|---|---|
| STY 1364 | X | X | X | X | X | X | X | X | X | X | X | X |
| STY 2657 | X | X | X | X | X | X | X | X | X | X | X | X |
| HCM 2.0069c | X | X | X | X | X | X | X | X | X | X | X | X |
| HCM 2.0043 | X | X | X | X | X | X | X | X | X | X | X | X |

-continued

|        | STY 2657 | HCM 2.0069c | HCM 2.0043 | HCM 1.137 | STY 2386 | STY 1479 | STY 2454 | STY 2248 | STY 3709 | STY 2155 | HCM 1.213c | STY 0712 |
|--------|----------|-------------|------------|-----------|----------|----------|----------|----------|----------|----------|------------|----------|
| HCM 1.137   | X | X | X | X | X | X | X | X | X | X | X | X |
| STY 2386    | X | X | X | X | X | X | X | X | X | X | X | X |
| STY 1479    | X | X | X | X | X | X | X | X | X | X | X | X |
| STY 2454    | X | X | X | X | X | X | X | X | X | X | X | X |
| STY 2248    | X | X | X | X | X | X | X | X | X | X | X | X |
| STY 3709    | X | X | X | X | X | X | X | X | X | X | X | X |
| STY 2155    | X | X | X | X | X | X | X | X | X | X | X | X |
| HCM 1.213c  | X | X | X | X | X | X | X | X | X | X | X | X |
| STY 0712    | X | X | X | X | X | X | X | X | X | X | X | X |

While our finding is based on the analysis of exemplary serum samples, i.e. serum as a biological sample, the methods and assays can be applied using other biological samples as well. The assays of the invention are in vitro assays for detecting whether a biological sample from a human comprises immunoglobulins against STY1364; STY2657; HCM2.0069c; HCM2.0043; HCM1.137; STY2386; STY1479; STY2454; STY2248; STY3709; STY2155; HCM1.213c; and STY0712. The biological sample may be any sample, and can be, for example, serum, stool, saliva, urine, blood, plasma, or sputum. Additional sample sources can also be used, such as spinal fluid and bone marrow, although these sample materials may not be as practical in the areas of the interest for use in a quick and simple diagnostic assay.

Immunoglobulins against STY1364; STY2657; HCM2.0069c; HCM2.0043; HCM1.137; STY2386; STY1479; STY2454; STY2248; STY3709; STY2155; HCM1.213c; and STY0712 or the biomarkers STY1364; STY2657; HCM2.0069c; HCM2.0043; HCM1.137; STY2386; STY1479; STY2454; STY2248; STY3709; STY2155; HCM1.213c; and STY0712 or even nucleic acids encoding these specific identified proteins can be present throughout the bodily fluids although the abundance of them may vary. However, we have discovered that detection of an immunoglobulin, protein or nucleic acid specific for any one of the biomarkers selected from STY1364; STY2657; HCM2.0069c; HCM2.0043; HCM1.137; STY2386; STY1479; STY2454; STY2248; STY3709; STY2155; HCM1.213c; and STY0712 or a combination thereof, is indicative of the presence of S. Typhi in the human individual from whom the sample was taken.

If/when S. Typhi infection is detected in a sample from an asymptomatic human subject, the subject carrying S. Typhi can be separated into a separate space, e.g., in a hospital or other institution and can also optionally be administered antibiotics to eliminate the silent S. Typhi infection so that the spread if the infection can be restricted or eliminated. Thus, the invention also provides a method of treating an asymptomatic human subject comprising detecting, in vitro, S. Typhi in a sample taken from the human subject and when S. Typhi is detected, then administering a treatment such as an antibiotic or providing the asymptomatic carrier with a separate isolated space in a hospital or other treatment facility. The method can further comprise performing an in vitro repeat test after the antibiotic treatment to allow assessment whether the treatment was successful, i.e., that the patient does not test positive for S. Typhi using the method of the invention or needs to be repeated, i.e., the patient still tests positive using the method of the invention.

One can use probes or sets of probes for detecting the markers that can be applied to a kit or an assay for detecting asymptomatic S. Typhi infection with a biological sample, such as blood, serum, plasma, sputum, buccal sample, urine and stool samples. The kits and assays preferably also comprise a positive control that includes the biomarker or a set of biomarkers that were discovered or alternatively comprise the immunoglobulins that one wishes to use for detection of the immunoglobulins, a biomarker or an antigen or combinations thereof. The types of immunoassays described in connection with the immunoglobulin detection assays, can all be applied to also direct biomarker assays in which one can use an antibody that is specific against the biomarker protein. The antibody-antigen complex formed between the biomarker-specific antibody and the biomarker can thus also be measured, in vitro, from the biological sample.

The signature profile of a sample comprising an asymptomatic S. Typhi infection compared to a sample not comprising asymptomatic S. Typhi infection comprises at least one immunoglobulin to the following biomarkers: STY1364; STY2657; HCM2.0069c; HCM2.0043; HCM1.137; STY2386; STY1479; STY2454; STY2248; STY3709; STY2155; HCM1.213c; and STY0712. These proteins can be used as antigens as a whole or fragments thereof can also be used. The antigens can be labeled or unlabeled. The antigens can be isolated or can be produced recombinantly using the nucleic acid sequences set forth below for each of them. One can use any one of the markers, any combination thereof or all of them. In some aspects the kits, assays and methods use no more than 20 different biomarkers as targets. Out of the 20, at least 1, 2, 3, 4, 5, 6, 7, 8, 9, 10, 11, 12, or all 13 can be the profile biomarkers, namely, STY1364; STY2657; HCM2.0069c; HCM2.0043; HCM1.137; STY2386; STY1479; STY2454; STY2248; STY3709; STY2155; HCM1.213c; and STY0712 or fragments thereof or specific antibodies against them. In some aspects, no more than 19, 18, 17, 16, 15, 14, 13, 12, 11, 10, 9, 8, 7, 6, 5, 4, 3, 2, or one probe is used in the assay or a kit or a method or a composition.

Amino acid sequences for the biomarkers of the invention are set forth below. These sequences or their fragments can be used as antigens either directly in the assays or to make specific antibodies against them. The proteins can be isolated or produced recombinantly and some short fragments can also be chemically synthesized according to the well-known protein synthesis techniques available to one of ordinary skill in the art.

```
>STY1364 hypothetical periplasmic protein
{Salmonella enterica serovar Typhi CT18}
                                   (SEQ ID NO: 1)
MKKKLKVLTLALASISSVCYAAMADYDTYVSNVQINNLSYGVYTSGGKET

QFFCIGLKHGSEAISINAMCKVDVYGNHKQGFDNMLNTAKYYYTTGGDVR

IYYKENVWRDPDFKSAFSSRELIAITTCSSSSYCMGPTVTN

>STY2657 xanthosine permease (xapB) {Salmonella
enterica serovar Typhi CT18}
                                   (SEQ ID NO: 2)
MGITSRLKVMSFLQYFIWGSWLVTLGSYMINTLDFTGANVGMVYSSKGLA

AIIMPGIMGIIADKWLRAERAYMLCHLVCAGALLYATTVTDPQTMFWVML

VNAMAYMPTIALSNSVSYSCLAKAGQDPVTSFPPVRVFGTIGFIVAMWTV

SLMGLELSSAQLYIASGASLLLALYALTLPKIPVAEKKANTTLVSKLGLD

AFVLFKNPRMAIFFLFAMMLGAVLQITNVFGNPFLHDFARNPEFADSFVV

KYPSILLSVSQMAEVGFILTIPFFLKRFGIKTVMLMSMLAWTLRFGFFAF

GDPSPFGFVLLLLSMIVYGCAFDFFNISGSVFVEQEVDSSIRASAQGLFM

TMVNGVGAWIGSLLSGMAVDYFSIDGVKDWQTIWLVFAAYALALAVIFAL

FFKYQHHPEKLSTKSLAH

>sty:HCM2.0069c hypothetical protein (A)
                                   (SEQ ID NO: 3)
MELTDKQIKDLVARRHPEYEKKKEHWDFLASTYAGGRAWFNDNIFRYFKE

GDQEFKERLERAYRFNHTREVVNLINKYLFKEVIHRNTDEAPEQIRNFWK

RATRQNTSIDAFMAAIDLQSSIYGRIWVVVDSTMNVDVESIADEKKNDAR

AYAYWISPQQLLDVAWDEDGNMLWALIVEIARDDEDPFTSTGQEYQRYRL

WTQNEWYLFREEVKKGSGNSGRRQAKVVLEDSGEHNLGVVPVFPVDCIGE

SESPYFSPSLIDDIAYLDRAVANYLSNLDAIIQDQTFSQLAIPVQSLLPG

DENHTKVLEMGTKRVFTFDSESGNQPFYLSPDPKQAQMIITTIKTVINEI

YHSVGVAGERTKQDNAQGIDNSSGAAKMYDFQRVNSLLVTKAERLERAER

QMMQLAAKWMGVELDEDHSLIAYPESFDIRGLTDEFAVAEKLSLLQAPDS

VRRHQMEMLIEKVFPNISEAMQKEFQKDLLKFPPKNDLNTLENKSVLTYD

RDAAQESGQDQPRGNGDSSTQETE

>sty:HCM2.0043 hypothetical protein (A)
                                   (SEQ ID NO: 4)
MRLNKLPGYGLPELAFWPQPKYERNEWSIYCLKLRTDGTPAWYRHFVDRG

TEYRAYGDDYEDYQTAKERALELNKSVDFNIDELPLSPAEKESLRLKVEK

ALTAKMRLMDEEHMMFNEAVKRHAKSPRVSIEELILKPDNENLRPLLFEA

LKQMPYLHFVLLPTFRVYLQLTGPNTWEWSYAGAREAKIGYKERIARGFG

LSGAAHWGKTKATIRSMLLPQANKLLQHASVKRMLDEALRNGQRVLVSGN

FVFWFEDKNQIGWSVKAVNESENTSNGNTLWKEGTIISKNHGRIVVLPYT

KENGEHVRGYTKNAPNDGNALPRHKNEYVELPFEVLEGDLMIGLLGELNY

E

>sty:HCM1.137 rep; replication protein (A)
                                   (SEQ ID NO: 5)
MAEIAVINHKKRKNSPRIVQSNELTEAAYSLSRDQKRLLYLFVHQIRKSD

GSLQEHDGICEIHVAKYAETFGLTSAEASKDIRQALKGFAGKEVVFYRPE

EDAGDEKGYESFPWFIKRAHSPSRGLYSVHINPYLIPFFIGLQNRFTQFR

LSETKEITNPYAMRLYESLCQYRKPDGSGVVSLKIDWIMERYQLPQSYQR

MPDFRRRFLKASVDEINSRTPMRLSYIEKKKGRQTTHIVFSFRDITSMTI

E

>STY2386 putative lipoprotein {Salmonella enterica
serovar Typhi CT18}
                                   (SEQ ID NO: 6)
MQVLRLMALPLFALSLSVSITGCDQKNDTLQGKQNNMTAFIKKIAASKES

EETQRYVGNLNGIEIKLTYYYKGDIVLRQISEHKLLYKTLKANNKEEAQK

MLSQVGEAYQGMPGLTERIDYYDSYATEYVDIDFTQAKISDLCKLPGSSI

DNCSAYYLSMIRSQKLLEESGYHRIN

>STY1479 possible ATP-binding protein {Salmonella
enterica serovar Typhi CT18}
                                   (SEQ ID NO: 7)
MHLRHLFSPRLRGSLLLGSLLVASSFSTLAAEDMLRKAVGKGAYEMAWSQ

QENALWLATSQSRKLDKGGVVYRLDPVTLEITQAIHNDLKPFGATINAAT

QTLWFGNTINSAVTAIDAKTGDVKGRLVLDARKRTEEVRPLQPRELVADA

ATNTIYISGVGKESAIWVVDGETIKLKTTIENTGKMSTGLALDSKAQRLY

TTNADGEFITIDTASNKILSRKKLLDDGKEHFFINLSLDTAGHRAFITDS

KATEVLVVDTRNGNILAKIAAPASLAVLYNPTRNEAYVTHRQAGQVSVID

AKTYNVVKTFDTPTYPNSLALSADGKTLYVSVKQKSTREQEATQPDDVIR

IAL

>STY2454 putative binding-protein-dependent
transporter (yejE) {Salmonella enterica serovar
Typhi CT18}
                                   (SEQ ID NO: 8)
MPRLSPVNQARWARFRHNRRGYWSLWIFLVVFSLSLCAELIANDKPLLVR

YEGQWYFPLVKNYSERDFGGPLATTADYQDPWLQRQLENRGWVLWAPVRF

GANTINFATTQPFPSPPSAKNWLGTDANGGDVFARILYGTRISILFGLML

TICSSVMGVLAGALQGYYGGKVDLWGQRLIEVWSGMPTLFLIILLSSVVQ

PNFWWLLAITVLFGWMSLVGVVRAEFLRTRNFDYIRAAQALGVSDRDIIL

RHMLPNAMVATLTFLPFILCSSITTLTSLDFLGFGLPLGSPSLGELLLQG

KNNLQAPWLGIAAFLSVAILLSLLIFIGEAVRDAFDPAKAV

>STY2248 PduG protein (pduG) {Salmonella enterica
serovar Typhi CT18}
                                   (SEQ ID NO: 9)
MRYIAGIDIGNSSTEVALARQDETGALTITHSALAENTGIKGTLRNVFGI

QEALALVAKRAGINVSDISLIRINEATPVIGDVAMETITETIITESTMIG

HNPKTPGGAGLGVGITITPEELLTRPADSSYILVVSSAFDFADIANVINA

SMRAGYQITGVILQRDDGVLVSNRLEKSLPIVDEVLYIDCIPLGMLAAIE

VAVPGKVIETLSNPYGIATVFNLNADETKNIVPMARALIGNRSAVVVKTP

SGDVKARAIPAGNLELQAQGRTVRVDVAAGAEAIMKAVDGYGKLDNVNGE
```

-continued

AGTNIGGMLEHVRQTMAELTNKPSSEIFIQDLLAVDTSVPVSVTGGLAGE

FSLEQAVGIASMVKSDRLQMAMIAREIEQKLNIDVQIGGAEAEAAILGAL

TTPGTTRPLAILDLGAGSTDASIINPKGEIIATHLAGAGDMVTMIIAREL

GLEDRYLAEEIKKYPLAKVESLFHLRHEDGSVQFFPTPLPPAVFARVCVV

KPDELVPLPGDLALEKVRAIRRSAKERVFVTNALRALRQVSPTGNIRDIP

FVVLVGGSSLDFEVPQLVTDALAHYRLVAGRGNIRGSEGPRNAVATGLIL

SWHKEFAYGQ

>STY3709 phosphoribosylaminoimidazolecarboxamide
formyltransferase and IMP cyclohydrolase
(bifunctional enzyme) (purH) {Salmonella enterica
serovar Typhi CT18}
(SEQ ID NO: 10)
MQQRRPVRRALLSVSDKAGIIEFAQALSARGVELLSTGGTARLLAEKGLP

VTEVSDYTGFPEMMDGRVKTLHPKVHGGILGRRGQDDAIMEQHHIAPIDM

VVVNLYPFAETVAREGCSLADAVENIDIGGPTMVRSAAKNHKDVAIVVKS

SDYDAIIKEMDANEGSLTLDTRFDLAIKAFEHTAAYDSMIANYFGSMVPA

YHGESKEAAGRFPRTLNLNFIKKQDMRYGENSHQQAAFYIEENVKEASVA

TAQQIQGKALSYNNIADTDAALECVKEFNEPACVIVKHANPCGVAVSTSI

LDAYDRAYKTDPTSAFGGIIAFNRELDAETAQAIISRQFVEVLIAPSASE

EALKITSAKQNVRVLTCGQWASRVPGLDFKRVNGGLLVQDRDLGMVSEAE

LRVVSKRQPTEQELRDALFCWKVAKFVKSNAIVYAKENMTIGIGAGQMSR

VYSAKIASIKAADEGLEVKGSAMASDAFFPFRDGIDAAAAVGVSCVIQPG

GSIRDDEVIAAADEHGIAMIFTDMRHFRH

>STY2155 invasion response-regulator (sirA)
{Salmonella enterica serovar Typhi CT18}
(SEQ ID NO: 11)
MINVLLVDDHELVRAGIRRILEDIKGIKVVGEACCGEDAVKWCRTNAVDV

VLMDMNMPGIGGLEATRKIARSTADIKVIMLTVHTENPLPAKVMQAGAAG

YLSKGAAPQEVVSAIRSVYSGQRYIASDIAQQMALSQIEPAKTETPFASL

SERELQIMLMITKGQKVNEISEQLNLSPKTVNSYRYRMFSKLNIHGDVEL

THLAIRHGLCNAETLTSQ

>sty:HCM1.213c transposase (A)
(SEQ ID NO: 12)
MNPFKGRHFQRDIILWAVRWYCKYGISYRELQEMLAERGVNVDHSTIYRW

VQRYAPEMEKRLRWYWRNPSDLCPWHMDETYVKVNGRWAYLYRAVDSRGR

TVDFYLSSRRNSKAAYRFLGKILNNVKKWQIPRFINTDKAPAYGRALALL

KREGRCPSDVEHRQIKYRNNVIECDHGKLKRIIGATLGFKSMKTAYATIK

GIEVMRALRKGQASAFYYGDPLGEMRLVSRVFEM

>STY0712 haemolysin-related protein {Salmonella
enterica serovar Typhi CT18}
(SEQ ID NO: 13)
MSDDNSHSSDTVNSKKGFFSLLLSQLFHGEPKNRDELLALIRDSGQNELI

DEDTRDMLEGVMDIADQRVRDIMIPRSQMITLKRNQTLDECLDVIIESAH

SRFPVISEDKDHIEGILMAKDLLPFMRSDAEAFSMDKVLRTAVVVPESKR

VDRMLKEFRSQRYHMAIVIDEFGGVSGLVTIEDILELIVGEIEDEYDEED

DIDFRQLSRHTWTIRALASIEDFNDAFGTHFSDEEVDTIGGLVMQAFGHL

PARGETIDIDGYQFKVAMADSRRIIQVHVRIPDDSPQPKLDE

The signature profile of a sample comprising S. Typhi compared to a sample not comprising S. Typhi comprises at least one of the following biomarkers: STY1364; STY2657; HCM2.0069c; HCM2.0043; HCM1.137; STY2386; STY1479; STY2454; STY2248; STY3709; STY2155; HCM1.213c; and STY0712. These biomarkers can be also detected by detecting nucleic acids encoding these proteins or by using the nucleic acids to make the proteins for the protein-based assays. Examples of nucleic acid sequences encoding the proteins are listed below. A skilled artisan can make appropriate changes into the sequences based on the known protein sequences and the genetic code, wherein different codons can be exchanged for coding the same amino acid.

>STY1364 hypothetical periplasmic protein
{Salmonella enterica serovar Typhi CT18}
(SEQ ID NO: 14)
ATGAAAAAGAAATTAAAGGTTCTGACTCTTGCTCTTGCGTCAATATCCAG

TGTTTGTTATGCAGCTATGGCTGATTATGATACGTATGTGAGTAATGTTC

AGATTAACAACCTGTCTTATGGTGTGTATACGTCAGGGGGTAAGGAAACT

CAGTTTTTTTGTATCGGACTGAAGCACGGGAGTGAAGCTATTAGTATCAA

TGCCATGTGTAAAGTGGATGTGTACGGGAATCATAAACAGGGGTTTGATA

ACATGCTAAATACAGCAAAGTATTATTATACAACAGGGGGGATGTAAGG

ATATATTATAAAGAGAATGTTTGGCGCGACCCCGATTTCAAAAGTGCATT

CTCTTCCAGGGAATTAATTGCGATAACTACTTGTAGCTCATCAAGTTATT

GTATGGGGCCTACGGTGACAAATTAA

>STY2657 xanthosine permease (xapB) {Salmonella
enterica serovar Typhi CT18}
(SEQ ID NO: 15)
ATGGGTATTACGTCCCGCTTAAAAGTCATGTCGTTCTTGCAATATTTTAT

CTGGGGGAGCTGGCTGGTTACCCTGGGCTCTTACATGATCAACACTCTGG

ATTTTACCGGCGCGAATGTCGGTATGGTCTACAGCTCAAAAGGACTGGCA

GCGATTATCATGCCGGGCATTATGGGGATCATTGCTGATAAATGGCTGCG

CGCTGAGCGAGCCTATATGCTTTGCCATCTGGTTTGCGCGGGGCGTTAT

TGTACGCTACCACCGTTACCGATCCCCAGACGATGTTCTGGGTGATGTTG

GTTAATGCGATGGCGTATATGCCAACGATTGCATTATCCAATAGCGTTTC

GTACTCCTGTCTGGCAAAGCAGGTCAGGATCCGGTAACGTCATTTCCGC

CCGTGCGCGTTTTCGGCACAATAGGTTTTATTGTTGCGATGTGGACGGTG

AGCCTGATGGGGCTGGAACTGAGCAGTGCGCAATTATACATCGCTTCTGG

CGCATCGTTATTGCTGGCCCTGTATGCGCTGACGTTACCGAAAATTCCGG

TAGCCGAGAAGAAGGCGAACACCACGCTTGTCAGTAAGCTCGGACTGGAT

GCTTTTGTTCTGTTTAAAAATCCACGCATGGCAATCTTCTTTTTGTTTGC

GATGATGTTGGGGGCGGTGCTGCAAATTACCAATGTCTTCGGTAATCCGT

TCCTGCATGATTTTGCCCGTAATCCTGAGTTTGCCGATAGTTTTGTGGTG

AAGTATCCCTCTATCTTGCTTTCAGTTTCGCAGATGGCGGAAGTGGGCTT

TATCCTCACCATTCCGTTCTTCCTTAAACGCTTTGGTATTAAAACGGTAA

TGCTGATGAGCATGCTGGCGTGGACGCTGCGTTTCGGCTTCTTTGCCTTT

GGCGATCCATCCCCGTTTGGCTTTGTGCTATTGCTGCTGTCGATGATTGT

```
TTATGGCTGCGCATTTGATTTCTTCAACATCTCAGGGTCAGTATTTGTAG

AGCAGGAGGTGGACTCAAGTATTCGCGCCAGCGCGCAGGGGCTGTTTATG

ACCATGGTTAACGGCGTGGGGGCGTGGATTGGGTCTCTTTTAAGCGGTAT

GGCCGTGGATTATTTTTCTATTGATGCGTAAAAGATTGGCAAACCATCT

GGCTGGTTTTTGCCGCCTACGCTCTGGCATTGGCCGTTATTTTTGCATTG

TTCTTTAAATATCAGCACCATCCAGAAAAACTGTCGACCAAATCATTAGC

ACATTAA
```
>sty:HCM2.0069c hypothetical protein (N)
(SEQ ID NO: 16)
```
ATGGAATTGACTGACAAGCAAATCAAAGACCTTGTGGCACGACGCCACCC

TGAATATGAGAAGAAAAAGAACATTGGGACTTCCTCGCCAGCACCTACG

CTGGCGGGCGTGCCTGGTTCAACGACAATATCTTCCGTTACTTCAAAGAG

GGCGATCAGGAGTTCAAAGAGCGCCTGGAACGCGCTTATCGCTTCAACCA

CACTCGTGAAGTGGTAAACCTCATCAACAAATACCTCTTCAAAGAGGTCA

TTCACCGCAACACTGATGAAGCGCCGGAGCAGATCCGCAATTTCTGGAAG

CGAGCCACGCGCCAGAACACCTCCATCGATGCGTTTATGGCGGCTATCGA

TCTGCAATCATCCATTTATGGCCGTATCTGGGTTGTCGTGGACAGCACCA

TGAACGTCGATGTTGAGTCTATTGCAGACGAGAAGAAAAATGATGCGCGT

GCCTACGCTTACTGGATTTCGCCACAGCAGCTGCTTGATGTTGCCTGGGA

TGAAGACGGCAATATGTTGTGGGCGCTGATTGTTGAAATCGCGCGCGACG

ACGAAGATCCGTTCACGTCAACCGGGCAGGAATACCAGCGTTACCGTCTG

TGGACGCAAAACGAGTGGTATCTGTTCCGTGAAGAAGTGAAGAAAGGTTC

CGGAAATAGCGGTCGTCGTCAGGCCAAAGTCGTTCTGGAGGATAGCGGCG

AGCATAATCTTGGCGTGGTGCCGGTGTTCCCGGTGGATTGCATTGGTGAA

AGCGAGTCTCCGTATTTCAGTCCGTCGTTGATTGACGACATCGCCTATCT

TGACCGCGCTGTGGCCAACTACCTGTCGAACCTTGACGCGATTATTCAGG

ATCAGACATTCAGCCAGCTGGCGATCCCGGTTCAGTCATTGCTGCCGGGC

GATGAAAACCACACCAAAGTGCTCGAAATGGGACAAAACGCGTCTTCAC

CTTCGACTCTGAGAGCGGTAATCAGCCATTCTACCTGTCTCCAGACCCGA

AACAGGCTCAGATGATCATCACCACGATTAAGACGGTGATTAACGAGATC

TACCATTCCGTTGGTGTGGCAGGTGAGCGAACCAAGCAGGATAACGCACA

GGGCATCGATAACTCTTCGGGCGCAGCGAAGATGTACGACTTCCAGCGCG

TTAACAGTCTGCTGGTGACAAAAGCAGAGCGCCTCGAAAGGGCAGAGCGG

CAGATGATGCAACTGGCAGCGAAATGGATGGGTGTCGAACTGGATGAAGA

CCACTCTCTGATTGCGTACCCGGAAAGTTTCGACATTCGCGGTCTGACTG

ACGAATTTGCCGTTGCTGAGAAACTGTCTCTGCTCCAGGCGCCTGATTCT

GTTCGTCGTCATCAGATGGAAATGCTCATCGAGAAGGTCTTCCCGAACAT

TTCCGAGGCGATGCAAAAGGAATTTCAAAAAGATCTCTTGAAATTTCCTC

CAAAAAATGATCTTAATACCCTTGAAAATAAGTCAGTACTTACTTATGAT

CGAGATGCGGCCCAAGAAAGCGGGCAAGATCAACCCCGAGGGAATGGGGA

CTCATCTACTCAAGAGACCGAGTGA
```
>sty:HCM2.0043 hypothetical protein (N)
(SEQ ID NO: 17)
```
ATGCGCTTGAATAAACTTCCCGGATATGGTCTTCCTGAGCTGGCTTTCT

GGCCGCAACCCAAATACGAAAGAAATGAGTGGTCGATTTATTGCCTGAA

GCTTCGCACTGACGGAACTCCGGCCTGGTACAGACATTTCGTCGATAGA

GGTACAGAATACCGCGCATATGGTGACGACTATGAGGATTACCAAACTG

CGAAAGAAAGAGCATTGGAGTTGAACAAGAGCGTAGATTTCAATATTGA

TGAACTTCCTCTCTCCCCAGCAGAAAAGAGTCATTACGCTTAAAAGTG

GAAAAGGCCCTCACCGCGAAAATGCGACTGATGGATGAGGAACATATGA

TGTTCAATGAAGCCGTCAAGAGACACGCCAAATCTCCCCGAGTTTCAAT

AGAAGAGTTAATTCTAAAACCTGATAACGAGAACCTACGTCCACTTCTT

TTTGAAGCACTAAAACAGATGCCATATCTGCATTTTGTTCTTCTTCCTA

CCTTCCGCGTATATCTTCAACTCACAGGGCCTAATACTTGGGAATGGTC

GTATGCCGGAGCAAGAGAAGCAAAAATCGGTTACAAGGAGCGTATTGCC

AGAGGTTTTGGTTTATCAGGAGCGGCCCATTGGGGTAAAACCAAGGCAA

CTATTCGCTCAATGCTGCTGCCGCAAGCCAATAAGCTGCTACAGCATGC

CAGCGTAAAAAGAATGCTGGATGAAGCTCTTCGTAACGGCCAAAGAGTT

CTCGTCTCTGGAAACTTTGTTTTCTGGTTCGAAGATAAGAATCAAATTG

GGTGGAGTGTTAAAGCAGTGAACGAAAGCGAAAACACCTCAAACGGTAA

TACGCTCTGGAAAGAAGGAACAATCATCTCCAAAAATCACGGCCGTATT

GTCGTTCTACCTTATACGAAGGAAAACGGCGAGCACGTTAGAGGGTACA

CCAAGAACGCACCGAATGACGGCAATGCGCTTCCGAGGCATAAGAATGA

ATACGTTGAGCTTCCCTTTGAAGTTTTGGAAGGAGACCTGATGATCGGA

TTGCTCGGTGAGCTTAATTACGAATAA
```
>sty:HCM1.137 rep; replication protein (N)
(SEQ ID NO: 18)
```
ATGGCGGAAATAGCGGTTATAAACCATAAAAAACGTAAAAATAGCCCGCG

GATTGTCCAGTCAAATGAGCTGACTGAGGCGGCATATAGTCTCTCCAGGG

ATCAAAAGCGTCTGCTGTATCTGTTCGTTCACCAGATCAGAAAATCCGAC

GGCTCCCTGCAGGAACATGACGGCATCTGCGAAATTCACGTTGCTAAATA

CGCTGAAACATTCGGGTTGACCTCCGCTGAAGCCAGTAAGGATATACGAC

AGGCTTTAAAAGGTTTTGCGGGTAAGGAAGTGGTTTTCTATCGCCCTGAA

GAGGATGCCGGCGATGAAAAAGGGTATGAATCCTTTCCCTGGTTTATTAA

ACGTGCGCACAGCCCATCAAGAGGGCTTTACAGCGTACATATCAACCCAT

ATCTGATTCCCTTCTTCATCGGGTTACAGAACCGGTTTACGCAGTTCCGG

CTCAGTGAAACAAAAGAGATTACCAATCCGTACGCCATGCGTTTATACGA

ATCTCTGTGCCAGTACCGTAAACCTGATGGCTCAGGTGTCGTGTCCCTGA

AAATCGACTGGATCATGGAACGCTACCAGCTACCTCAAAGTTACCAGCGT

ATGCCGGACTTTCGCCGCCGTTTCCTGAAGGCAAGTGTTGACGAGATCAA

CAGCCGGACACCAATGCGCCTTTCTTACATCGAGAAAAAGAAAGGCCGCC

AGACGACGCATATCGTATTTTCCTTCCGTGATATAACCTCCATGACGATT

GAATAG
```
>STY2386 putative lipoprotein {Salmonella enterica serovar Typhi CT18}

(SEQ ID NO: 19)
ATGCAGGTTCTACGTCTTATGGCACTGCCACTATTCGCGCTCTCTCTATC

GGTTAGCATAACTGGCTGCGATCAGAAAAACGATACTCTCCAGGGAAAGC

AAAATAACATGACAGCGTTTATCAAGAAGATAGCCGCTAGCAAAGAGTCA

GAGGAAACACAACGCTATGTAGGTAATCTCAACGGTATTGAAATCAAGTT

AACCTATTACTACAAAGGGGATATCGTTTTACGTCAAATATCTGAACATA

AACTACTTTATAAGACCCTGAAAGCCAATAATAAAGAAGAAGCACAAAAA

ATGCTGAGTCAAGTCGGCGAAGCTTATCAGGGTATGCCGGGTTTGACTGA

ACGAATCGACTATTATGATAGCTATGCTACGGAATATGTGGATATTGATT

TTACCCAGGCAAAAATAAGCGACCTCTGTAAATTGCCAGGATCATCAATT

GACAACTGTTCCGCGTACTATCTGTCAATGATTCGCTCGCAGAAACTGTT

GGAAGAGAGCGGGTATCATAGAATCAATTAG

>STY1479 possible ATP-binding protein {Salmonella enterica serovar Typhi CT18}
(SEQ ID NO: 20)
ATGCACTTACGTCATCTTTTTTCGCCGCGCCTGCGTGGTTCTTTATTGTT

AGGTTCGCTCCTCGTCGCATCCTCATTTAGCACGCTGGCGGCGGAAGACA

TGCTGCGTAAAGCGGTAGGCAAAGGCGCTTATGAGATGGCCTGGAGTCAG

CAAGAAAACGCGCTCTGGCTGGCTACATCGCAAAGCCGTAAACTGGATAA

AGGCGGCGTAGTTTATCGTCTCGACCCGGTGACGCTGGAAATCACGCAAG

CGATTCATAACGATCTCAAGCCGTTCGGCGCCACCATCAATGCCGCGACC

CAAACGCTGTGGTTTGGCAATACCATTAACAGCGCAGTTACCGCGATTGA

TGCCAAAACGGGTGATGTAAAAGGTCGTCTGGTACTTGATGCGCGCAAAC

GTACTGAAGAGGTTCGTCCGTTACAGCCCCGTGAGCTGGTTGCCGATGCG

GCGACCAACACGATCTACATTAGCGGTGTTGGTAAAGAGAGTGCTATTTG

GGTAGTGGATGGCGAAACCATCAAACTGAAAACGACGATCGAAAATACCG

GCAAAATGAGTACGGGTCTGGCGCTCGACAGTAAAGCACAACGCCTGTAC

ACCACCAATGCGGATGGCGAATTTATCACCATCGATACCGCCAGCAATAA

AATTCTCAGTCGTAAGAAGTTGCTGGATGACGGTAAAGAACACTTCTTTA

TTAATCTGAGTCTCGATACCGCAGGTCATCGCGCGTTTATCACCGACTCG

AAGGCAACTGAGGTTCTGGTTGTCGATACCCGTAATGGCAATATTCTTGC

CAAAATCGCGGCGCCTGCCTCTTTGGCCGTCCTGTATAATCCGACACGTA

ACGAGGCGTATGTGACGCACCGTCAGGCAGGGCAGGTCAGCGTGATCGAT

GCGAAGACCTATAACGTTGTTAAAACGTTCGATACGCCGACGTACCCGAA

TAGCCTGGCGCTATCGGCAGACGGTAAAACGCTCTACGTCAGCGTGAAGC

AGAAATCGACACGTGAACAAGAAGCGACGCAGCCGGATGATGTTATTCGC

ATTGCTCTGTAA

>STY2454 putative binding-protein-dependent transporter (yejE) {Salmonella enterica serovar Typhi CT18}
(SEQ ID NO: 21)
ATGCCGCGATTAAGCCCGGTCAATCAGGCCCGCTGGGCGCGTTTCCGCCA

TAATCGCCGGGGCTACTGGTCACTATGGATTTTCCTGGTAGTGTTCAGCC

TGAGCTTATGCGCGGAACTGATTGCTAACGATAAGCCATTGCTGGTGCGC

TATGAAGGCCAGTGGTATTTTCCGCTGGTAAAAAATTACAGCGAGCGCGA

TTTCGGCGGCCCGCTGGCGACAACGGCAGACTATCAGGACCCCTGGCTAC

AACGGCAGCTTGAGAATCGGGGCTGGGTGTTGTGGGCCCCCGTACGCTTT

GGCGCCAATACCATTAATTTTGCCACCACGCAGCCTTTCCCCTCCCCGCC

TTCGGCGAAAAACTGGCTGGGCACCGATGCGAATGGCGGCGACGTTTTCG

CCCGCATCCTGTACGGCACCCGCATTTCTATTTTATTTGGCCTGATGTTA

ACGATTTGCTCCAGCGTCATGGGTGTACTGGCGGGCGCGCTACAGGGCTA

TTATGGCGGCAAAGTCGATTTATGGGGGCAACGTCTCATCGAAGTCTGGT

CGGGGATGCCGACCCTGTTTCTGATTATTTTACTTTCCAGCGTAGTGCAG

CCTAACTTCTGGTGGCTGCTGGCCATAACCGTGCTGTTTGGCTGGATGAG

TCTGGTGGGCGTGGTGCGCGCCGAGTTTTTACGGACCCGCAATTTTGACT

ATATCCGCGCCGCGCAGGCGCTTGGCGTCAGCGATCGTGACATTATCCTG

CGCCATATGTTGCCTAATGCGATGGTCGCTACCCTGACATTTTTACCGTT

CATTTTATGTAGTTCCATCACCACCCTGACGTCGCTGGATTTTCTGGGAT

TCGGTCTGCCGCTTGGCTCCCCTTCTCTCGGCGAACTTCTTTTACAGGGG

AAAAACAACTTACAGGCTCCCTGGCTGGGGATCGCCGCCTTTCTGTCTGT

CGCCATTCTGCTATCGCTGCTGATTTTTATCGGCGAAGCGGTACGCGACG

CCTTTGATCCTGCTAAGGCGGTATAA

>STY2248 PduG protein (pduG) {Salmonella enterica serovar Typhi CT18}
(SEQ ID NO: 22)
ATGCGATATATAGCTGGCATTGACATCGGTAACTCATCAACGGAAGTCGC

ACTGGCGCGGCAAGATGAGACTGGCGCACTAACGATTACACACAGCGCGC

TGGCGGAAAACACCGGGATCAAAGGCACGTTGCGTAACGTGTTCGGCATT

CAGGAAGCGCTCGCCCTCGTCGCAAAGCGCGCGGGGATCAATGTCAGCGA

TATTTCGCTCATCCGCATTAACGAAGCCACGCCGGTGATTGGCGATGTGG

CGATGGAAACCATTACCGAAACCATCATCACCGAATCGACAATGATCGGC

CATAACCCAAAAACGCCGGGCGGAGCAGGCCTTGGTGTGGGTATCACGAT

TACGCCGGAGGAGCTGTTAACCCGCCCGGCGGACTCGTCCTATATTCTGG

TGGTATCGTCAGCCTTTGATTTTGCTGATATCGCCAATGTTATCAACGCC

TCAATGCGCGCCGGATACCAGATTACCGGCGTCATTTTGCAGCGCGACGA

TGGCGTACTGGTCAGCAACCGGCTGGAAAAATCGCTACCGATTGTCGATG

AAGTTCTGTACATCGACTGCATTCCGCTGGGGATGCTGGCGGCGATTGAA

GTCGCCGTGCCGGGAAAGGTTATCGAAACCCTCTCTAACCCTTACGGCAT

CGCCACCGTATTCAACCTCAACGCCGATGAGACGAAAAACATCGTCCCGA

TGGCGCGCGCGCTGATTGGCAACCGTTCCGCCGTGGTGGTTAAAACGCCA

TCCGGCGACGTCAAAGCGCGCAATACCCGCCGGTAACCTGGAGCTGCA

GGCTCAGGGTCGTACCGTGCGCGTGGATGTTGCCGCCGGTGCCGAAGCTA

TCATGAAAGCGGTGGACGGCTACGGCAAGCTCGACAACGTCAACGGCGAG

GCCGGGACCAATATCGGCGGCATGCTGGAGCATGTGCGCCAGACCATGGC

CGAGCTAACCAATAAGCCGAGCAGCGAGATTTTCATTCAGGATCTTCTGG

CCGTTGACACCTCGGTTCCGGTGAGCGTCACCGGCGGTCTGGCCGGGGAG

TTCTCGCTGGAGCAGGCCGTCGGCATCGCCTCGATGGTGAAATCAGACCG

TCTGCAAATGGCGATGATTGCCCGTGAAATTGAGCAGAAGCTTAATATCG

ACGTGCAGATCGGCGGCGCTGAGGCTGAAGCCGCCATTCTGGGCGCGCTG

ACCACGCCGGGTACCACCCGACCGCTGGCGATCCTCGACCTCGGCGCGGG

CTCCACCGATGCCTCCATCATCAACCCTAAAGGTGAAATCATCGCCACCC

ATCTCGCCGGGGCAGGCGACATGGTCACGATGATTATTGCCCGCGAACTG

GGGCTGGAAGACCGCTATCTGGCGAAGAGATCAAAAAATACCCGCTGGC

TAAGGTCGAAAGCCTGTTCCACTTACGCCACGAGGACGGCAGCGTCCAGT

TCTTCCCGACGCCGCTGCCTCCTGCGGTGTTCGCCCGCGCTCTGCGTGGTG

AAACCGGACGAACTGGTGCCGCTTCCCGGCGACTTAGCGCTGGAAAAAGT

GCGCGCCATTCGCCGCAGCGCTAAAGAACGCGTCTTTGTCACCAACGCCC

TGCGCGCGCTGCGTCAGGTCAGTCCAACCGGCAACATTCGCGATATTCCG

TTCGTGGTGCTGGTCGGCGGCTCGTCGCTGGATTTCGAAGTTCCGCAGTT

GGTCACCGATGCGCTGGCGCACTACCGCTAGTCGCCGGGCGAGGAAATA

TTCGCGGCAGCGAAGGCCCAAGAAACGCGGTGGCCACCGGTCTGATTCTC

TCCTGGCACAAGGAGTTTGCATATGGACAGTAA

>STY3709 phosphoribosylaminoimidazolecarboxamide
formyltransferase and IMP cyclohydrolase
(bifunctional enzyme) (purH) {Salmonella enterica
serovar Typhi CT18}
(SEQ ID NO: 23)

ATGCAACAACGTCGTCCAGTCCGCCGCGCTTTGCTCAGTGTTTCTGACAA

GGCCGGTATCATCGAATTCGCCCAGGCACTTTCCGCACGCGGTGTGGAGC

TGCTGTCTACGGGGGGCACCGCCCGCCTGTTAGCAGAAAAAGGCCTGCCG

GTGACCGAAGTTTCCGATTACACCGGTTTCCCGGAAATGATGGATGGACG

CGTAAAGACCCTGCATCCAAAAGTACACGGTGGCATCCTCGGTCGTCGCG

GTCAGGACGATGCCATTATGAACAGCACCACATCGCCCCTATCGATATG

GTTGTCGTTAACCTATATCCGTTCGCCGAAACCGTGGCACGCGAAGGCTG

CTCGCTGGCAGATGCAGTAGAGAACATTGATATCGGCGGCCCGACCATGG

TGCGCTCTGCTGCTAAGAACCATAAAGACGTCGCCATCGTGGTGAAGAGC

AGCGACTACGACGCCATTATTAAAGAGATGGATGCTAACGAAGGTTCTCT

GACCCTCGACACCCGTTTCGATCTCGCGATTAAAGCCTTCGAACACACCG

CCGCCTACGACAGCATGATCGCCAACTACTTCGGCAGCATGGTTCCGGCC

TACCACGGTGAAAGCAAAGAAGCCGCCGGTCGCTTCCCGCGTACGCTGAA

CCTGAACTTCATTAAGAAGCAGGATATGCGCTACGGCGAGAACAGCCACC

AGCAGGCTGCCTTCTATATAGAAGAGAATGTGAAAGAAGCATCCGTTGCC

ACCGCACAGCAGATTCAGGGCAAAGCGCTCTCTTATAACAATATCGCCGA

TACCGATGCGGCGCTGGAATGCGTGAAAGAGTTCAACGAGCCAGCCTGCG

TGATCGTCAAGCACGCCAACCCGTGCGGCGTGGCGGTAAGTACCTCGATT

CTCGATGCTTATGACCGTGCGTATAAAACAGACCCGACCTCCGCGTTCGG

CGGCATTATCGCCTTCAACCGCGAGCTGGATGCCGAAACCGCGCAGGCCA

TCATCTCCCGTCAGTTCGTGGAAGTGCTCATCGCCCCATCCGCAAGCGAA

GAAGCGCTGAAAATCACCTCAGCCAAGCAGAACGTCCGTGTTCTGACCTG

CGGCCAATGGGCAAGCCGCGTTCCGGGCCTGGATTTCAAACGCGTTAACG

GCGGTCTGCTGGTTCAGGACAGGGATCTGGGTATGGTGAGCGAAGCTGAA

CTGCGCGTGGTGTCCAAACGCCAGCCGACCGAGCAGGAACTGCGCGATGC

GCTGTTCTGCTGGAAGGTAGCCAAGTTCGTGAAATCCAACGCCATTGTGT

ATGCCAAAGAGAACATGACTATCGGCATAGGCGCAGGCCAGATGAGCCGC

GTGTACTCCGCGAAAATCGCTAGCATTAAAGCGGCTGACGAAGGTCTGGA

AGTGAAAGGCTCTGCTATGGCTTCCGACGCGTTCTTCCCGTTCCGTGATG

GCATTGATGCCGCTGCCGCTGTCGGCGTGAGCTGCGTTATCCAGCCTGGC

GGTTCTATCCGTGATGATGAAGTCATTGCCGCCGCCGACGAACACGGCAT

TGCGATGATCTTCACCGACATGCGCCACTTCCGCCATTAA

>STY2155 invasion response-regulator (sirA)
{Salmonella enterica serovar Typhi CT18}
(SEQ ID NO: 24)

TTGATCAACGTTCTTCTTGTTGATGACCACGAACTGGTGCGCGCAGGGAT

ACGACGCATTCTTGAAGATATAAAGGGCATTAAAGTTGTCGGTGAAGCGT

GCTGCGGAGAGGATGCGGTAAAATGGTGCCGTACTAACGCCGTTGACGTC

GTGCTGATGGATATGAACATGCCCGGTATTGCCGGCCTTGAGGCGACGCG

TAAAATTGCCCGATCGACAGCGGATATCAAAGTGATCATGCTGACCGTCC

ATACGGAGAACCCGTTGCCCGCCAAAGTGATGCAGGCTGGCGCAGCTGGC

TATCTCAGCAAAGGCGCTGCGCCTCAGGAGGTGGTGAGCGCTATTCGTTC

GGTGTATTCCGGACAACGTTATATCGCCTCCGATATCGCTCAACAGATGG

CGCTCAGTCAGATTGAGCCTGCAAAAACGGAAACGCCGTTCGCCAGTTTG

TCTGAACGCGAGTTGCAGATTATGCTGATGATCACCAAGGGCCAGAAGGT

CAATGAGATTTCAGAACAGCTGAATCTCAGTCCTAAAACGGTGAACAGCT

ATCGCTATCGTATGTTCAGTAAATTAAACATTCATGGTGATGTTGAGCTG

ACTCACCTGGCAATCCGCCATGGCCTGTGTAATGCGGAGACGTTAACAAG

CCAGTGA

>sty:HCM1.213c transposase (N)
(SEQ ID NO: 25)

ATGAACCCATTCAAAGGCCGGCATTTTCAGCGTGACATCATTCTGTGGGC

CGTACGCTGGTACTGCAAATACGGCATCAGTTACCGTGAGCTGCAGGAGA

TGCTGGCTGAACGCGGAGTGAATGTCGATCACTCCACGATTTACCGCTGG

GTTCAGCGTTATGCGCCTGAAATGGAAAAACGGCTGCGCTGGTACTGGCG

TAACCCTTCCGATCTTTGCCCGTGGCACATGGATGAAACCTACGTGAAGG

TCAATGGCCGCTGGGCGTATCTGTACCGGGCCGTTGACAGCGGGGCCGC

ACTGTCGATTTTTATCTCTCCTCCCGTCGTAACAGCAAAGCTGCATACCG

GTTTCTGGGTAAAATCCTCAACAACGTGAAGAAGTGGCAGATCCCGCGAT

TCATCAACACGGATAAAGCGCCCGCCTATGGTCGCGCGCTTGCTCTGCTC

AAACGCGAAGGCCGGTGCCCGTCTGACGTTGAACACCGACAGATTAAGTA

CCGGAACAACGTGATTGAATGCGATCATGGCAAACTGAAACGGATAATCG

GCGCCACGCTGGGATTTAAATCCATGAAGACGGCTTACGCCACCATCAAA

GGTATTGAGGTGATGCGTGCACTACGCAAAGGCCAGGCCTCAGCATTTTA

TTATGGTGATCCCCTGGGCGAAATGCGCCTGGTAAGCAGAGTTTTTGAAA

TGTAA

-continued

>STY0712 haemolysin-related protein {Salmonella enterica serovar Typhi CT18}
(SEQ ID NO: 26)
ATGAGCGACGACAATTCACACAGTAGTGACACAGTAAACAGTAAAAAGGG

ATTTTTTTCCCTGCTACTCAGCCAGCTTTTCCACGGTGAACCTAAAAACC

GTGATGAGTTGCTGGCGCTGATCCGTGATTCCGGGCAGAACGAGCTTATC

GATGAAGATACGCGCGATATGCTCGAAGGCGTAATGGACATCGCCGACCA

GCGCGTTCGCGATATTATGATCCCGCGCTCCCAGATGATTACCCTGAAAC

GCAACCAGACGCTGGACGAATGTCTCGATGTTATCATCGAGTCCGCCCAC

TCGCGTTTTCCGGTGATCAGCGAAGATAAAGATCACATTGAAGGGATTCT

GATGGCCAAAGATTTGCTGCCGTTTATGCGCAGCGATGCCGAAGCCTTCA

GCATGGACAAAGTGTTACGTACCGCGGTTGTCGTACCGGAAAGCAAACGG

GTTGACCGTATGCTCAAGGAATTCCGCTCCCAGCGCTACCATATGGCCAT

CGTTATCGATGAGTTTGGCGGCGTTTCCGCCTTGTGACTATCGAAGACA

TCCTCGAACTGATTGTCGGTGAAATTGAAGATGAGTATGACGAAGAAGAC

GATATCGACTTCCGTCAGCTTAGCCGCCATACCTGGACGATTCGCGCGCT

GGCGTCGATTGAAGACTTCAATGACGCTTTCGGCACCCACTTCAGCGATG

AAGAAGTCGATACCATCGGCGGGCTGGTGATGCAGGCGTTCGGCCATTTA

CCGGCCCGCGGCGAAACCATTGACATTGATGGTTACCAGTTCAAAGTGGC

AATGGCCGATAGTCGTCGTATTATTCAGGTGCATGTCAGGATCCCGGATG

ACTCGCCCCAGCCAAAACTGGACGAATAA

The above-identified nucleic acids can be used to produce the biomarker antigens for detection or production of proteins to produce biomarker-specific antibodies, or design primers that specifically amplify each nucleic acid. Also, the nucleic acids can be used to design probes that specifically hybridize to the nucleic acids.

Nucleic acids can be detected using well known assays, which most of the time include the step of amplifying the biomarker encoding nucleic acid or fragments thereof to facilitate detection.

As used herein, a probe is defined as a compound that specifically binds to a particular molecule or class of molecules, i.e., in the present application, a probe is a compound or a molecule that specifically binds any one of the biomarker-specific immunoglobulins or that binds directly to the identified biomarker. Probes can include proteins, such as antigens derived from the biomarkers, antibodies, nucleic acid molecules, carbohydrates, lipids, ligands, drugs, ions and any other compound that can specifically bind to the biomarkers or immunoglobulins that are specific for the biomarkers, namely, STY1364; STY2657; HCM2.0069c; HCM2.0043; HCM1.137; STY2386; STY1479; STY2454; STY2248; STY3709; STY2155; HCM1.213c; and STY0712. Thus, a biomarker binding probe specifically binds to any immunoglobulin that the body has produced against the biomarker or directly to the biomarker, including STY1364; STY2657; HCM2.0069c; HCM2.0043; HCM1.137; STY2386; STY1479; STY2454; STY2248; STY3709; STY2155; HCM1.213c; and STY0712 proteins, and unique fragments of any of these. In some aspects of all the embodiments of the invention, the biomarker is a nucleic acid encoding any of the proteins, i.e., S. *Typhi*-specific antigens selected from STY1364; STY2657; HCM2.0069c;

HCM2.0043; HCM1.137; STY2386; STY1479; STY2454; STY2248; STY3709; STY2155; HCM1.213c; and STY0712.

A "probe set" is used herein to describe a set of identical or different probes that detect one biomarker. For example, one can use several copies of the complete proteins of STY1479 as a "probe set" to detect the STY1479-specific antibodies in the sample. One can also use several different fragments of STY1479 as a probe set to capture the STY1479-specific antibodies in the biological sample. Similarly, the probe set can also comprise several copies of the same fragment of STY1479. One of ordinary skill in the art understands that immunoassays typically include a certain density of the specific probes as a probe set to allow sufficient amount of the antibodies to bind to the target to allow meaningful detection. Accordingly, the terms "probe" and "probe set" are used herein interchangeably.

The probe can be labeled with any detectable labels well-known to one of ordinary skill in the art, e.g., a reactive enzyme, a fluorescent label, or a radioactive label can be used.

A probe can be an antigen selected from the biomarkers or fragments thereof or it can be a biomarker-specific antibody. In some aspects of the invention the S. *Typhi*-specific antigen binds to an immunoglobulin in a biological sample taken from an asymptomatic individual infected with S. *Typhi*, and the complex of immunoglobulin-antigen is detected, or a biomarker-specific antibody binds to the biomarker in the biological sample and the specific antibody-biomarker complex is detected. Thus, detection of the immunoglobulin-antigen complex or the biomarker-antibody complex is indicative of asymptomatic *S. Typhi* infection being present in the sample. The method of detection depends on the method of forming the biomarker antigen-immunoglobulin complex or the biomarker-specific antibody complex and the kinds of labels used to allow detection of the bound complexes.

The probes are either directly labeled or the complexes can be labeled in a sandwich-type assay indirectly.

Antibodies, whether antibodies against the immunoglobulins or the biomarker-specific antibodies, can be polyclonal or monoclonal, and they can be labeled. One can use a secondary antibody in a sandwich-type assay to detect the first bound antibody-antigen complex, wherein the antigen is any one or a combination of STY1364; STY2657; HCM2.0069c; HCM2.0043; HCM1.137; STY2386; STY1479; STY2454; STY2248; STY3709; STY2155; HCM1.213c; and STY0712.

Thus, the invention includes kits that comprise an antibody that is specific for the biomarker selected from STY1364; STY2657; HCM2.0069c; HCM2.0043; HCM1.137; STY2386; STY1479; STY2454; STY2248; STY3709; STY2155; HCM1.213c; and STY0712. The kit may include just one antibody or a combination of two or more, up to 13 antibodies that are each specific for a different biomarker selected from STY1364; STY2657; HCM2.0069c; HCM2.0043; HCM1.137; STY2386; STY1479; STY2454; STY2248; STY3709; STY2155; HCM1.213c; and STY0712.

Both polyclonal and monoclonal antibodies can be prepared using the entire proteins as antigens or fragments thereof.

The term "fragment" refers to any subject polypeptide having an amino acid residue sequence shorter than that of a polypeptide whose amino acid residue sequence is described herein. Typically, the antigenic fragments are at least 5 consecutive amino acids long, and can be longer. The fragments can be modified to be more antigenic using well known methods in the art.

The fragment preferably comprises at least one epitope. An "epitope" is the collective features of a molecule, such as primary, secondary and tertiary peptide structure, and charge, that together form a site recognized by an immunoglobulin, T cell receptor or HLA molecule. Alternatively, an epitope can be defined as a set of amino acid residues which is involved in recognition by a particular immunoglobulin, or in the context of T cells, those residues necessary for recognition by T cell receptor proteins and/or Major Histocompatibility Complex (MHC) receptors. Epitopes make antigens antigenic.

Epitopes are present in nature, and can be isolated, purified or otherwise prepared/derived by human or non-human means. For example, epitopes can be prepared by isolating the S. Typhi peptides from a natural source, such as a bacterial culture, or they can be synthesized in accordance with standard protocols in the art.

Synthetic epitopes can comprise artificial amino acids "amino acid mimetics," such as D isomers of natural occurring L amino acids or non-natural amino acids such as cyclohexylalanine. Throughout this disclosure, the terms epitope and peptide are often used interchangeably. In some embodiments, one can use analogs of said epitopes to produce additional antibodies against the S. Typhi proteins described herein.

Protein or polypeptide molecules that comprise one or more S. Typhi peptide epitopes on the biomarkers of the invention as well as additional amino acid(s) are still within the bounds of the invention. In certain embodiments, there is a limitation on the length of a polypeptide of the invention of, for example, not more than 120 amino acids, not more than 110 amino acids, not more than 100 amino acids, not more than 95 amino acids, not more than 90 amino acids, not more than 85 amino acids, not more than 80 amino acids, not more than 75 amino acids, not more than 70 amino acids, not more than 65 amino acids, not more than 60 amino acids, not more than 55 amino acids, not more than 50 amino acids, not more than 45 amino acids, not more than 40 amino acids, not more than 35 amino acids, not more than 30 amino acids, not more than 25 amino acids, 20 amino acids, 15 amino acids, or 14, 13, 12, 11, 10, 9 or 8 amino acids. In some instances, the embodiment that is length-limited occurs when the protein/polypeptide comprising an epitope of the invention comprises a region (i.e., a contiguous series of amino acids) having 100% identity with a native sequence.

The term "derived" when used to discuss a peptide epitope is a synonym for "prepared." A derived epitope can be isolated from a natural source, or it can be synthesized in accordance with standard protocols in the art.

Protein or polypeptide molecules that comprise one or more S. Typhi biomarker peptide epitopes of the invention as well as additional amino acid(s) are still within the bounds of the invention.

In certain embodiments, there is a limitation on the length of a polypeptide used for producing the antibody. For example, if one uses STY1479 as a source for antigens, one can use a protein which is between about 8 and about 353 amino acids, or not more than 350 amino acids, not more than 300 amino acids, not more than 250 amino acids, not more than 200 amino acids, not more than 150 amino acids, not more than 125 amino acids, not more than 110 amino acids, not more than 100 amino acids, not more than 95 amino acids, not more than 90 amino acids, not more than 85 amino acids, not more than 80 amino acids, not more than 75 amino acids, not more than 70 amino acids, not more than 65 amino acids, not more than 60 amino acids, not more than 55 amino acids, not more than 50 amino acids, not more than 45 amino acids, not more than 40 amino acids, not more than 35 amino acids, not more than 30 amino acids, not more than 25 amino acids, or a protein that is about 20-8 amino acids, such as about 20, amino acids, 15 amino acids, or 14, 13, 12, 11, 10, 9 or 8 amino acids. In some instances, the embodiment that is length-limited occurs when the protein/polypeptide comprising an epitope of the invention comprises a region (i.e., a contiguous series of amino acids) having 100% identity with a native sequence.

For a polypeptide comprising an epitope of the invention and a region with 100% identity with the native S. Typhi polypeptide sequence, the region with 100% identity to the native sequence generally has a length of: less than or equal to 120 amino acids, more often less than or equal to 100 amino acids, often less than or equal to 85 amino acids, often less than or equal to 75 amino acids, often less than or equal to 65 amino acids, and often less than or equal to 50 amino acids. In certain embodiments, the S. Typhi polypeptide comprises a peptide having a region with less than 50 amino acids that has 100% identity to a native peptide sequence, in any increment of amino acids down to 5 amino acids (i.e., 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, or 50-5 amino acids). Preferably, such S. Typhi polypeptide comprises one or more S. Typhi peptide epitopes that are capable of eliciting an immune reaction and thus production of suitable antibodies.

In some embodiments embodiment, the polyclonal antibodies are generated using the whole proteins.

In some embodiments, monoclonal antibodies are produced using fragments of the identified biomarkers of the invention. The fragments typically include an immunogenic peptide or at least one peptide epitope.

An "immunogenic peptide" or "peptide epitope" is a peptide that will bind an HLA molecule and induce a cytotoxic T lymphocyte (CTL) response and/or a helper T lymphocyte (HTL) response. Thus, immunogenic peptides of the invention are capable of binding to an appropriate HLA molecule and thereafter inducing a cytotoxic T lymphocyte (CTL) response, or a helper T lymphocyte (HTL) response, to the peptide.

The term "motif" refers to a pattern of residues in an amino acid sequence of defined length, usually a peptide of from about 8 to about 13 amino acids for a class I HLA motif and from about 16 to about 25 amino acids for a class II HLA motif, which is recognized by a particular HLA molecule. Motifs are typically different for each HLA protein encoded by a given human HLA allele. These motifs often differ in their pattern of the primary and secondary anchor residues.

The term "residue" refers to an amino acid or amino acid mimetic incorporated into a peptide or protein by an amide bond or amide bond mimetic.

"Synthetic peptide" refers to a peptide that is not naturally occurring, but is man-made using such methods as chemical synthesis or recombinant DNA technology.

Antibodies, both polyclonal and monoclonal, can be produced by a skilled artisan either by themselves using well known methods or they can be manufactured by service providers who specialize making antibodies based on known protein sequences. In the present invention, the protein sequence s are known and thus production of antibodies against them is a matter of routine.

For example, production of monoclonal antibodies can be performed using the traditional hybridoma method by first immunizing mice with an isolated S. Typhi protein or fragment thereof of choice or even with a crude extract of S. Typhi and making hybridoma cell lines that each produce a specific monoclonal antibody. The antibodies secreted by the different clones are then assayed for their ability to bind to the antigen using, e.g., ELISA or Antigen Microarray Assay, or immuno-dot blot technique. To detect the antibodies that are most specific for the detection of the protein of interest can be selected using routine methods and using the antigen and other antigens as well as S. Typhi crude extract as controls. The antibody that most specifically detects the desired antigen and protein and not other antigens or proteins will be selected for the detection assays.

The best clones can then be grown indefinitely in a suitable cell culture medium. They can also be injected into mice (in the peritoneal cavity, surrounding the gut) where they produce tumors secreting an antibody-rich ascites fluid from which the antibodies can be isolated and purified.

The antibodies can be purified using techniques that are well known to one of ordinary skill in the art.

The probe can also be a nucleic acid probe, which can be labeled. The biomarker can be detected using, e.g., amplification of the nucleic acids encoding the biomarker proteins, and detection of the amplification products by any known means.

We provide immunoassays in which any one of the antigens, or any combination thereof, is used to detect immunglobulins against the antigens selected from the newly-identified proteomic profile comprising STY1364; STY2657; HCM2.0069c; HCM2.0043; HCM1.137; STY2386; STY1479; STY2454; STY2248; STY3709; STY2155; HCM1.213c; and STY0712.

In the assays, the antigen, which can be the entire protein or one or more fragment thereof, or a combination of proteins or fragments thereof, are contacted with the biological sample, and the presence or amount of the immunoglobulin bound to the antigen is detected, typically by detecting the presence of the label which can be affixed either to the antigen, and more typically to the anti-immunoglobulin antibody that is used to detect any antibodies from the sample that have formed a complex with the test antigen.

Antibodies against the immunoglobulins are well known and widely available in the industry. For example, human IgG can be detected using Human IgG Monoclonal Antibody (F37-5) from Thermo Scientific Pierce. This antibody works, e.g., in ELISA, RIA (radioimmuno assay) or IP (Immuniprecipitation) assay. Antibodies against a combination of immunoglobulins can also be used, such as R1343AP, R1343B, R1343F, R1343HRP, R1343P, R1343T and R1343TR from e.g., *Acris* Antibodies, all of which can be used to detect human IgG, IgA, and IgM. In our example, we detected the immunoglobulins with anti-human IgG and IgA conjugated with horseradish peroxidase.

The antibodies are typically labeled. The labels include, e.g., biotin, alkaline phosphatase, horse radish peroxidase, fluorescent label, such as FITC, TRITC, or TEXAS RED®.

Detection of the immunoglobulin-antigen complex indicates asymptomatic *S. Typhi* infection in the biological sample. Detection can be performed using a non-human machine, such as an ELISA reader, or a gamma counter or any other detection system that can detect the label included into the assay.

We also provide immune assays in which each antibody is designed to directly detect the specific biomarker of the assay. The immune assay can use two or more antibodies so that two or more markers can be analyzed in the same assay. The novel aspect of the immunoassay is the selection of the specific markers we have identified, namely, proteins STY1364; STY2657; HCM2.0069c; HCM2.0043; HCM1.137; STY2386; STY1479; STY2454; STY2248; STY3709; STY2155; HCM1.213c; and STY0712, any one of which or any combination of which can be used to detect a chronic, asymptomatic *T. Typhi* carrier who poses a risk of spreading *S. Typhi* bacteria and infection in his/her surroundings.

Typically, in an assay, the biological sample is either treated first to remove background and then contacted, in vitro, with at least one probe specific to the biomarker or the biological sample may be directly contacted, in vitro, with the at least one probe specific to the biomarker. The formed complex between the biomarker and the probe is then detected. The detection can be made automatically, e.g., using a reader, such as an ELISA-reader, and the result can be sent to a display, such as a computer display or the result may be a print out or the result may be detected as a signal on the assay, such as a plus or a minus sign depending whether the complex is present or absent in the sample.

In some aspects and all aspects of this embodiment, the step of detecting asymptomatic *S. Typhi* infection is performed using a stereomicroscope, an ELISA, an ELISPOT, a FLUOROSPOT, a FACS, an FP, an FLT or a FRET, or mass spectrometry.

In the methods and assays of the invention, the presence of immunoglobulins against the 13 identified *S. Typhi* biomarkers or any one or any combination of the 13 identified *S. Typhi* biomarker proteins is determined using antibodies specific for the immunoglobulins or *S. Typhi* proteins and detecting immunospecific binding of each antibody to its respective cognate marker.

Any suitable immunoassay method may be utilized, including those which are commercially available, to determine the level of an immunoglobulin against each at least one of the 13 identified S. Typhi biomarkers or of each at least one of the specific *S. Typhi* proteins measured according to the invention. Extensive discussion of the known immunoassay techniques is not required here since these are known to those of skill in the art. Typical suitable immunoassay techniques include sandwich enzyme-linked immunoassays (ELISA), radioimmunoassays (RIA), competitive binding assays, homogeneous assays, heterogeneous assays, etc. Various of the known immunoassay methods are reviewed, e.g., in Methods in Enzymology, 70, pp. 30-70 and 166-198 (1980).

In the assays of the invention, "sandwich-type" assay formats can be used. These typically involve mixing the test sample with detection probes conjugated with a specific binding member (e.g., antibody) for the analyte (e.g., the urine sample) to form complexes between the analyte and the conjugated probes. These complexes are then allowed to contact a receptive material (e.g., antibodies) immobilized within the detection zone. Binding occurs between the analyte/probe conjugate complexes and the immobilized receptive material, thereby localizing "sandwich" complexes that are detectable to indicate the presence of the analyte. This technique may be used to obtain quantitative or semiquantitative results. Some examples of such sandwich-type assays are described in by U.S. Pat. No. 4,168,146 to Grubb, et al. and U.S. Pat. No. 4,366,241 to Tom, et al. An alternative technique is the "competitive-type" assay. In a competitive assay, the labeled probe is generally conjugated with a molecule that is identical to, or an analog of, the analyte. Thus, the labeled probe competes with the analyte of interest for the available receptive material. Competitive assays are typically used for detection of analytes such as haptens, each hapten being monovalent and capable of binding only one antibody molecule. Examples of competitive immunoassay devices are described in U.S. Pat. No. 4,235,601 to Deutsch, et al., U.S. Pat. No. 4,442,204 to Liotta, and U.S. Pat. No. 5,208,535 to Buechler, et al.

The antibodies can be labeled. In some embodiments, the detection antibody is labeled by covalently linking to an enzyme, label with a fluorescent compound or metal, label with a chemiluminescent compound. For example, the detection antibody can be labeled with catalase and the conversion uses a colorimetric substrate composition comprises potassium iodide, hydrogen peroxide and sodium thiosulphate; the enzyme can be alcohol dehydrogenase and the conversion uses a colorimetric substrate composition comprises an alcohol, a pH indicator and a pH buffer, wherein the pH indicator is neutral red and the pH buffer is glycine-sodium hydroxide; the enzyme can also be hypoxanthine oxidase and the conversion uses a colorimetric substrate composition comprises xanthine, a tetrazolium salt and 4,5-dihydroxy-1,3-benzene disulphonic acid. In one embodiment, the detection antibody is labeled by covalently linking to an enzyme, label with a fluorescent compound or metal, or label with a chemiluminescent compound.

Direct and indirect labels can be used in all immunoassays. A direct label can be defined as an entity, which in its natural state, is visible either to the naked eye or with the aid of an optical filter and/or applied stimulation, e.g., ultraviolet light, to promote fluorescence. Examples of colored labels which can be used include metallic sol particles, gold sol particles, dye sol particles, dyed latex particles or dyes encapsulated in liposomes. Other direct labels include radionuclides and fluorescent or luminescent moieties. Indirect labels such as enzymes can also be used according to the invention. Various enzymes are known for use as labels such as, for example, alkaline phosphatase, horseradish peroxidase, lysozyme, glucose-6-phosphate dehydrogenase, lactate dehydrogenase and urease. For a detailed discussion of enzymes in immunoassays see Engvall, Enzyme Immunoassay ELISA and EMIT, Methods of Enzymology, 70, 419-439 (1980).

In some embodiments, the immunoassay method or assay comprises a sandwitch technique for measuring the level of the *S. Typhi* antigen specific immunoglobulins or *S. Typhi* proteins in the biological sample taken from the patient. According to this method one of the probes is a "capture antigen" or a "capture antibody" and the other is a "detector" antibody. The capture antibody or antigen is immobilized on a solid support which may be any of various types which are known in the art such as, for example, microtiter plate wells, beads, tubes and porous materials such as nylon, glass fibers and other polymeric materials. The capture material may be present in a diagnostic dip-stick or a microfluidic device. In this method, a solid support constitutes the solid phase, e.g., microtiter plate wells, coated with a capture antibody, preferably monoclonal, raised against the particular *S. Typhi* protein of interest or a capture antigen, which is the *S. Typhi* protein or a peptide fragment thereof. One or more of the antibodies or antigens may be present in any solid phase, and they may be organized in such way, that a positive signal in any x/y coordinates of e.g., a planar strip or positive signal along a microfluidic device's detection area, will directly indicate which *S. Typhi* protein the positive signal corresponds to.

Patient body fluid, e.g., urine, blood, serum, stool, sputum, tears or saliva, which may be diluted or not, and typically at least 1, 2, 3, 4, 5, 10, or more standards and controls are added to separate or the same solid support and incubated. When the *S. Typhi* protein is present in the body fluid it is captured by the immobilized antigen or antibody which is specific for the *S. Typhi* protein in question. After incubation and washing, an anti-marker protein detector antibody, e.g., an immunoglobulin-specific antibody or a polyclonal rabbit anti-marker protein antibody, is added to the solid support. The detector antibody binds to marker protein bound to the capture antibody to form a sandwich structure. After incubation and washing an anti-IgG antibody, e.g., a polyclonal goat anti-rabbit IgG antibody, labeled with an enzyme such as horseradish peroxidase (HRP) is added to the solid support. After incubation and washing a substrate for the enzyme is added to the solid support followed by incubation and the addition of an acid solution to stop the enzymatic reaction.

For example, the degree of enzymatic activity of immobilized enzyme is determined by measuring the optical density of the oxidized enzymatic product on the solid support at the appropriate wavelength, e.g., 450 nm for HRP. The absorbance at the wavelength is proportional to the amount of S. Typhi protein in the fluid sample. A set of marker protein standards is used to prepare a standard curve of absorbance vs. S. Typhi protein concentration. This method is useful because test results can be provided in 45 to 50 minutes and the method is both sensitive over the concentration range of interest for each S. Typhi protein and is highly specific.

The antigen or antibody can be attached to a surface. Examples of useful surfaces on which the antibody can be attached for the purposes of detecting the desired antigen include nitrocellulose, PVDF, polystyrene, and nylon. The surface or support may also be a porous support (see., e.g., U.S. Pat. No. 7,939,342).

The standards may be positive samples comprising various concentrations of the at least one S. Typhi protein to be detected to ensure that the reagents and conditions work properly for each assay. The standards also typically include a negative control, e.g., for detection of contaminants. In some aspects of the embodiments of the invention, the positive *S. Typhi* controls may be titrated to different concentrations, including non-detectable amounts and clearly detectable amounts, and in some aspects, also including a sample that shows a signal at the threshold level of detection in the biological sample.

The assays can be carried out in various assay device formats including those described in U.S. Pat. Nos. 4,906,439; 5,051,237 and 5,147,609 to PB Diagnostic Systems, Inc.

The diagnosis of a sample from an S Typhi carrier can be made if the presence of immunoglobulins against any one of the 13 identified *S. Typhi* biomarkers or any one of the 13 identified *S. Typhi* proteins is detected, in vitro, in the patient's biological sample.

In addition to presence of the *S. Typhi* protein in the sample, one can also measure the quantity of the *S. Typhi* protein in the sample using routine methods known to one skilled in the art.

The assay devices used according to the invention can be arranged to provide a quantitative (how much) or a qualitative (present or not present) result.

The assays may be carried out in various formats including, as discussed previously, a microtiter plate or a microfluidic device format are particularly useful for carrying out the assays in a batch mode. The assays may also be carried out in automated immunoassay analyzers which are well known in the art and which can carry out assays on a number of different samples. These automated analyzers include continuous/random access types. Examples of such systems are described in U.S. Pat. Nos. 5,207,987 and 5,518,688 to PB Diagnostic Systems, Inc. Various automated analyzers that are commercially available include the OPUS® and OPUS MAGNUM® analyzers.

Another assay format which can be used according to the invention is a rapid manual test which can be administered at the point-of-care at any location. Typically, such point-of-care assay devices will provide a result which is either "positive" i.e. showing the protein is present, or "negative" showing that the protein is absent. Typically, a control showing that the reagents worked in general is included with such point-of-care system. Point-of-care systems, assays and devices have been well described for other purposes, such as pregnancy detection (see, e.g., U.S. Pat. Nos. 7,569,397; 7,959,875; and 8,287,817, which are all incorporated herein by reference with respect to description regarding rapid diagnostic devices, assay, buffers, and methods in general).

Accordingly, the invention also provides devices, such as point-of-care test strips and microfluidic devices to perform the in vitro assays of the present invention.

It should be recognized also that the assay devices used according to the invention can be provided to carry out one single assay for a particular marker protein or to carry out a plurality of assays, or a "multiplex assay", from a single volume of body fluid, for a corresponding number of different immunoglobulins against any one of the 13 identified S. Typhi biomarkers or S. Typhi proteins or biomarkers. In some embodiments, an assay device of the latter type is one which can provide a semiquantitative result for the immunoglobulins against any one of the 13 identified S. Typhi biomarkers or S. Typhi proteins measured according to the invention, namely, STY1364; STY2657; HCM2.0069c; HCM2.0043; HCM1.137; STY2386; STY1479; STY2454; STY2248; STY3709; STY2155; HCM1.213c; and STY0712. These devices typically are adapted to provide a distinct visually detectable colored band at the location where the capture antibody for the particular marker protein is located when the concentration of the marker protein is above the threshold level. For additional detailed discussion of assay types which can be utilized according to the invention as well as various assay formats and automated analyzer apparatus see e.g., U.S. Pat. No. 5,747,274, incorporated by reference in its entirety.

In other embodiments, the assays or immunoassays of the invention comprise beads coated with an antigen comprising one or more of the S. Typhi proteins or one or more fragments of the same protein or a specific antibody against an isolated S. Typhi protein or a fragment thereof, as described e.g., in Binder S R., Lupus. 2006, 15:412-21, incorporated herein by reference with respect to the assay format described therein. Commonly used are polystyrene beads that can be labeled to establish a unique identity. Detection is performed by flow cytometry.

Detection of the immunoglobulins against any one of the 13 identified S. Typhi biomarkers or the 13 identified S. Typhi biomarkers can further be performed using multiplex technologies, wherein several antigens and/or antibodies are used in the same assay. Other types of bead-based immunoassays are well known in the art, e.g., laser bead immunoassays and related magnetic bead assays (Fritzler, Marvin J; Fritzler, Mark L, Expert Opinion on Medical Diagnostics, 2009, pp. 3: 81-89, incorporated by references with respect to the description of the laser bead immunoassays and related magnetic bead assays).

In one embodiment, the invention further provides a system to facilitate detection of S. Typhi in an asymptomatic human subject, comprising: a determination module configured to receive and output the amount of immunoglobulins against any one of the 13 identified S. Typhi biomarkers or the 13 identified S. Typhi biomarkers detected in a biological sample extracted from a human; a storage module configured to store output information from the determination module; a comparison module adapted to compare the data stored on the storage module with reference data and/or control data, and to provide a comparison content, and an output module for displaying the comparison content for the user, wherein if there is no detectable amount of S. Typhi antigens or antibodies in the sample, then the subject is not a carrier for S. Typhi and if the peptide or antibody is detected that the subject is a S. Typhi carrier. If the subject is S. Typhi carrier then the subject is or can be administered an antibiotic. Other measures can also be taken to, e.g., isolate the subject from vulnerable subjects until the treatment has resulted in eliminating the silent infection. The automated system is specifically designed to detect the positive or alternatively or additionally, negative signals from the assay with respect to the biomarkers selected from STY1364; STY2657; HCM2.0069c; HCM2.0043; HCM1.137; STY2386; STY1479; STY2454; STY2248; STY3709; STY2155; HCM1.213c; and STY0712. The software that typically runs the automated systems, can either call the specific markers if they are positive and optionally print out, e-mail or otherwise indicate the determination of a S. Typhi positive sample and/or S. Typhi negative sample.

The collected biological sample is in some embodiments undiluted. In some embodiments the sample can be diluted or concentrated depending on the detection application.

In some embodiments, one can essentially concentrate the proteins in the biological sample by using a solid surface coated with either an antigen to capture the immunoglobulins or a monoclonal antibody to capture the antigen. The recovered captured antibodies or antigens can then be analyzed using any suitable methods well known to one skilled in the art. The solid surface can be e.g., beads, such as magnetic beads, polystyrene beads, or gold beads, or in an array or a microarray format using a glass, a plastic or a silicon chip. Such antigen capture can be also a part of a channel in a microfluidic device.

In one embodiment, the invention provides a computer readable storage medium comprising: a storing data module containing data from a sample obtained from a subject that represents a signal level from an immunoassay for the S. Typhi antigens present in the urine sample taken from the human patient; a comparison module that compares the data stored on the storing data module with a reference data and/or control data, and to provide a comparison content, and an output module displaying the comparison content for the user, wherein the presence of a detectable amount of S. Typhi antibodies or antigens relative to the reference value and/or control value indicates that the subject is a carrier of S. Typhi.

Kits provided according to the present invention include kits comprising the compositions, i.e., the antibodies, and optionally comprising a device with a solid surface, such as a lateral flow assay device, to which the antibodies are bound. Kits, such as those described in U.S. Pat. No. 7,932,099, comprising the component of at least one of the 13 S. Typhi specific antigen described, e.g., in Table 1 are provided.

The kit can comprise one or more of the antigens, e.g., immobilized on a solid support, in combination with an antibody against one or more immunoglobulin, positive and negative controls, and optionally also sample taking vessels and a chart indicating the location of the positive and negative controls and the test areas.

The invention also provides simple-to-use point-of-care diagnostic test strips akin to pregnancy detection strips, wherein the strip comprises at least one S. Typhi antigen selected from the proteins of the invention or a fragment thereof, or an antibody against at least one of the listed S. Typhi proteins. The test strip may comprise a positive and negative control to show the user that the reagents work properly and/or that the sample has been added to the strip properly. The strips may be provided with or without a casing and with or without additional reagents.

In its most simple form, the strip comprises at least one S. Typhi antigen or antibody against at least one of the S. Typhi proteins provided herewith, wherein the at least one antigen/antibody is immobilized on the solid or porous surface of the test strip surface.

"Antigen" can be the entire protein or can comprise one or more separate fragments of the proteins specific for the S. Typhi proteome of the invention, namely, STY1364; STY2657; HCM2.0069c; HCM2.0043; HCM1.137; STY2386; STY1479; STY2454; STY2248; STY3709; STY2155; HCM1.213c;
and STY0712.

"S. Typhi specific antibody" is an immunoglobulin, or derivative or fragment or active portion thereof, having an area on the surface or in a cavity which specifically binds to and is thereby defined as complementary with a particular spatial and polar organization of another molecule. The antibody can be monoclonal or polyclonal and can be prepared by techniques that are well known in the art such as, for example, immunization of a host and collection of sera or hybrid cell line technology using the S. Typhi proteins of the invention STY1364; STY2657; HCM2.0069c; HCM2.0043; HCM1.137; STY2386; STY1479; STY2454; STY2248; STY3709; STY2155; HCM1.213c; and STY0712.

The test strip may include a simple indication of positive result upon detection of one or more of the proteins set forth in the specification.

Diagnostic test strips for lateral flow assays, such as the test strip assay described herein, may be constructed as described in the art, see, e.g., U.S. Patent application publication No. 20100196200; 20100129935; 20090253119; 20090111171.

A "test strip" can include one or more bibulous or non-bibulous materials. If a test strip comprises more than one material, the one or more materials are preferably in fluid communication. One material of a test strip may be overlaid on another material of the test strip, such as for example, filter paper overlaid on nitrocellulose. Alternatively or in addition, a test strip may include a region comprising one or more materials followed by a region comprising one or more different materials. In this case, the regions are in fluid communication and may or may not partially overlap one another. Suitable materials for test strips include, but are not limited to, materials derived from cellulose, such as filter paper, chromatographic paper, nitrocellulose, and cellulose acetate, as well as materials made of glass fibers, nylon, dacron, PVC, polyacrylamide, cross-linked dextran, agarose, polyacrylate, ceramic materials, and the like. The material or materials of the test strip may optionally be treated to modify their capillary flow characteristics or the characteristics of the applied sample. For example, the sample application region of the test strip may be treated with buffers to correct the pH or specific gravity of an applied urine sample, to ensure optimal test conditions.

The material or materials can be a single structure such as a sheet cut into strips or it can be several strips or particulate material bound to a support or solid surface such as found, for example, in thin-layer chromatography and may have an absorbent pad either as an integral part or in liquid contact. The material can also be a sheet having lanes thereon, capable of spotting to induce lane formation, wherein a separate assay can be conducted in each lane. The material can have a rectangular, circular, oval, triagonal or other shape provided that there is at least one direction of traversal of a test solution by capillary migration. Other directions of traversal may occur such as in an oval or circular piece contacted in the center with the test solution. However, the main consideration is that there be at least one direction of flow to a predetermined site. In the following discussion strips will be described by way of illustration and not limitation.

The support for the test strip, where a support is desired or necessary, will normally be water insoluble, frequently non-porous and rigid but may be elastic, usually hydrophobic, and porous and usually will be of the same length and width as the strip but may be larger or smaller. The support material can be transparent, and, when a test device of the present invention is assembled, a transparent support material can be on the side of the test strip that can be viewed by the user, such that the transparent support material forms a protective layer over the test strip where it may be exposed to the external environment, such as by an aperture in the front of a test device. A wide variety of non-mobilizable and non-mobilizable materials, both natural and synthetic, and combinations thereof, may be employed provided only that the support does not interfere with the capillary action of the material or materials, or non-specifically bind assay components, or interfere with the signal producing system. Illustrative polymers include polyethylene, polypropylene, poly(4-methylbutene), polystyrene, polymethacrylate, poly (ethylene terephthalate), nylon, poly(vinyl butyrate), glass, ceramics, metals, and the like. Elastic supports may be made of polyurethane, neoprene, latex, silicone rubber and the like.

A "control zone" is a region of a test strip in which a dye as described supra can be observed to shift location, appear, change color, or optionally to disappear. Detection or observation of the control zone may be done by any convenient means, depending upon the particular choice of dye, especially, for example but not limited to, visually, fluorescently, by reflectance, radiographically, and the like. As will be described, the dye may or may not be applied directly to the control zone, depending upon the design of the control being used.

A "label" may be any molecule bound to a specific binding member that can produce a detectable signal. In the present invention, the label may be inert and provide a signal by concentrating in the detection zone, or it may serve solely as a binding site for a member of the signal producing system, or it may spontaneously produce a detectable signal or may produce a detectable signal in conjunction with a signal producing system. The label may be isotopic or nonisotopic.

"Proximal end" of a test strip refers to the end of a test device or test strip that includes the sample application aperture of the test device and sample application zone of the test strip.

"Reagent zone" refers to a region of a test strip where reagent is provided. The reagent zone can be on a reagent pad, a separate segment of bibulous or non-bibulous material included on the test strip, or it can be a region of a bibulous or non-bibulous material of a test strip that also includes other zones, such as an analyte detection zone. The reagent zone can carry a detectable label, which may be a direct or indirect label. Preferably the reagent is provided in a form that is immobile in the dry state and mobile in the moist state. A reagent can be a specific binding member, an analyte or analyte analog, an enzyme, a substrate, indicators, components of a signal producing system, chemicals or compounds such as buffering agents, reducing agents, chelators, surfactants, etc., that contribute to the function of the test strip assay.

"Sample" is any material to be tested for the presence or amount of an analyte. The sample can be a fluid sample, preferably a liquid sample, such as a urine sample. Examples of liquid samples that may be tested using a test device of the present invention include bodily fluids including blood, serum, plasma, saliva, urine, ocular fluid, semen, and spinal fluid. Viscous liquid, semi-solid, or solid specimens may be used to create liquid solutions, eluates, suspensions, or extracts that can be samples.

The test strip may be accessed through a sample application aperture. "Sample application aperture" refers to the portion of a test device where an opening in the test device provides access to the sample application zone of the test strip. In one embodiment of the present invention, a sample application aperture is created by an open-ended channel at the proximal end of the test device. Preferably, a test strip in engaged in the open-ended channel such that sample contacted with the sample application aperture is thereby applied to the test strip. In an alternate embodiment, a sample application aperture is formed by an opening in the front of a test device, such that the sample application zone of the test strip is in fluid communication with the exterior of the test device.

"Sample application zone" is the portion of a test strip where sample can be applied. The sample application zone of a test strip of the present invention preferably occurs at the sample application aperture of a test device of the present invention, and is in fluid communication with the sample application aperture.

"Specific binding member" is one of two different molecules having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody. In the case of binding pairs such as avidin-biotin, reagent can be labeled with one member of this pair and a detection zone can include the other member of this pair in a capture type assay. Other general types of assays using avidin-biotin pairs or binding pairs of this type are known in the art. In addition, an antigen or epitope can be labeled for use as a reagent for the detection of antibodies that bind with or specifically bind with such an antigen or epitope. In one aspect of this type of assay, an antigen or epitope can be detectably labeled and present in the reagent zone and the antigen or epitope can be present in a detection zone. This type of assay can be used, for example, to detect antibodies such as antibodies that bind with or specifically bind with an etiological agent in a sample. Other general types of assays using labeled antigen or labeled epitopes are known in the art.

The test strip may also include a test result zone. "Test results zone" is a region of a test strip that provides a detectable signal indicating the presence of the analyte. The test results zone can include an immobilized binding reagent specific for an analyte ("specific binding member"), and/or an enzyme that reacts with the analyte. A test results determination zone can include one or more analyte detection zones. Other substances that may allow or enhance detection of the analyte, such as substrates, buffers, salts, may also be provided in the test results determination zone. One or more members of a signal producing system may be bound directly or indirectly to the detection zone. A test results determination zone can optionally include one or more control zones that provide indication that the test has been performed properly.

The invention further provides microfluidic devices for the detection of *S. Typhi* from asymptomatic individuals, specifically from a stool or urine. The components of the assays, namely, the antibody and the reagents needed for detection of the immunoglobulins against any one of the 13 identified *S. Typhi* biomarkers or the 13 identified *S. Typhi* biomarkers in a biological sample described herein can be used in the format of a microfluidic device. Such devices have been well described in the art, see, e.g., U.S. Pat. Nos. 6,444,461; 6,479,299; 7,041,509, incorporated herein by reference in their entirety.

The microfluidic devices can be designed to comprise a channel or chamber that contains one or more of the 13 identified *S. Typhi* biomarkers, or one or more fragments thereof, or antibodies against the 13 identified *S. Typhi* proteins preferably immobilized on the channel surface. The device can be supplied with appropriate buffers for binding the proteins from a sample, such as a stool or urine sample to the antibodies and detecting the bound proteins either inside the device or eluting them out and detecting them in the eluted sample.

The methods of the invention can be automated using robotics and computer directed systems. The biological sample, such as the urine sample, can be injected into a system, such as a microfluidic devise entirely run by a robotic station from sample input to output of the result.

The step of displaying the result can also be automated and connected to the same system or in a remote system. Thus, the sample analysis can be performed in one location and the comparison and the result analysis in another location, the only connection being, e.g., an internet connection in such way that the analysis result can be fed from the analysis module to the comparison module which can then either in the same location or by sending the result to a third location, which may or may not be the same location as the first location wherein the analysis was performed, to be displayed in a format suitable for either reading by a health professional or by a patient.

In one embodiment, the analysis, comparison and the result is performed in one location, such as in aspects including a point-of-care test strip.

We provide kits that comprise a positive control for at least one or more of the immunoglobulins against any one of the 13 identified *S. Typhi* biomarkers or the 13 identified biomarkers selected from STY1364; STY2657; HCM2.0069c; HCM2.0043; HCM1.137; STY2386; STY1479; STY2454; STY2248; STY3709; STY2155; HCM1.213c; and STY0712 or any combination thereof, wherein the positive control can be the antigen or the antigen-specific immunoglobulin. The kit can optionally comprise instructions, tools, buffers and other reagents for sample collection and preparation, and interpretation of the results, i.e., that if the biomarker is present, then the individual is selected as a carrier of S. Typhi.

The kits can also comprise a solid support carriers, such as arrays or beads for the probes.

We also provide methods for treatment of asymptomatic S. Typhi carriers to reduce their risk of spreading S. Typhi while shedding. The method comprises detecting S. Typhi in a biological sample taken from the asymptomatic human subject using one or more of the biomarkers selected from STY1364; STY2657; HCM2.0069c; HCM2.0043; HCM1.137; STY2386; STY1479; STY2454; STY2248; STY3709; STY2155; HCM1.213c; and STY0712; and if the biomarker is detected to be present in the biological sample, then administering an antibiotic, such as Ampicillin, effective to treat S. Typhi infection into the subject. If no biomarker is detected, then no antibiotic is necessary and the antibiotic treatment can be avoided.

Unless defined otherwise, all technical and scientific terms used herein have the same meaning as is commonly understood by one of skill in the art to which the invention(s) belong. All patents, patent applications, published applications and publications, Genbank sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, the term "comprising" is an open term meaning that other elements can also be present in addition to the defined elements presented. The use of "comprising" indicates inclusion rather than limitation.

As used herein, the term consisting essentially of, is intended to refer to a kit, assay or method, which consists of the specifically indicated biomarkers or antibodies against them but can also include components that are non-essential for assaying S. Typhi, such as controls, buffers, solid supports and the like.

The term "consisting of" is intended to be a closed term indicating the presence of just the components listed in the claim.

The references cited throughout the specification and examples are herein incorporated by reference in their entireties or to the extent that is consistent with the description in the specification and examples.

Accordingly, we provide an in vitro assay for identifying Salmonella enterica serotype Typhi (S. Typhi) in a biological sample taken from an asymptomatic human subject comprising: contacting at least one antigen selected from: STY1479; STY1364; STY2657; HCM2.0069c; HCM2.0043; HCM1.137; STY2386; STY2454; STY2248; STY3709; STY2155; HCM1.213c; and STY0712 or one or more fragments thereof or a combination thereof with the biological sample to form an antigen-sample mixture; contacting the antigen-sample mixture with a labeled human immunoglobulin-specific antibody to form a labeled antigen-immunoglobulin complex; detecting presence of the labeled antigen-immunoglobulin complex, and if the labeled antigen-immunoglobulin complex is present then identifying Salmonella enterica serotype Typhi in the biological sample.

In some or all aspects of the method, the method can further comprise detecting the amount of the immunoglobulin-antigen complex and comparing the amount of the immunoglobulin-antigen complex to a reference value and if the amount of the immunoglobulin-antigen complex is higher than the reference value, then identifying the biological sample as comprising Salmonella enterica serotype Typhi.

In some or all aspects of the method, the step of detecting is performed by a non-human machine.

In some or all aspects of the method, the step of comparing is performed by a non-human medium.

In some or all aspects of the method, the at least one biomarker comprises biomarker STY 1479.

In some or all aspects of the method, the at least one biomarker is STY 1479.

We also provide an in vitro assay comprising a solid surface comprising no more than 20 probe sets for a biomarker wherein the no more than 20 probe sets comprise at least one of the proteins selected from: STY1364; STY2657; HCM2.0069c; HCM2.0043; HCM1.137; STY2386; STY1479; STY2454; STY2248; STY3709; STY2155; HCM1.213c; STY0712 and one or more fragments thereof.

In some or all aspects of the assay, the assay further comprises a positive and/or a negative control.

In some or all aspects of the assay, the solid surface comprises no more than 15 probe sets.

In some or all aspects of the assay, the probe sets comprise at least STY1479.

In some or all aspects of the assay, the solid surface consists essentially of a probe set for STY1479 and a positive and a negative assay control comprising a human immunoglobulin.

We further provide an in vitro assay for identifying Salmonella enterica serotype Typhi in a biological sample taken from an asymptomatic human subject comprising: contacting the biological sample with a labeled antibody against at least one or any combination of the biomarkers selected from: STY1364; STY2657; HCM2.0069c; HCM2.0043; HCM1.137; STY2386; STY1479; STY2454; STY2248; STY3709; STY2155; HCM1.213c; and STY0712 to form an antibody-biomarker complex; detecting the antibody-biomarker complex and if the antibody-biomarker complex is detected, then identifying Salmonella enterica serotype Typhi in the biological sample.

In some or all aspects of the assay, it further comprises detecting the amount of the antibody-biomarker complex and comparing the amount of the antibody-biomarker complex to a reference value and if the amount of the antibody-biomarker complex is higher than the reference value, then identifying the biological sample as comprising Salmonella enterica serotype Typhi.

In some or all aspects of the assay, the step of detecting is performed by a non-human machine.

In some or all aspects of the assay, the step of comparing is performed by a non-human medium.

The in vitro assay of the four preceding paragraphs, wherein the at least one biomarker comprises biomarker STY 1479.

In some or all aspects of the assay, the at least one biomarker is STY 1479.

We also provide an in vitro assay comprising a solid surface comprising no more than 20 probes for a biomarker wherein the no more than 20 probes comprise at least one of the biomarkers selected from: STY1364; STY2657;

HCM2.0069c; HCM2.0043; HCM1.137; STY2386; STY1479; STY2454; STY2248; STY3709; STY2155; HCM1.213c; and STY0712.

In some or all aspects of the assay, the assay further comprises a positive and/or a negative control probe.

In some or all aspects of the assay, the solid surface comprises no more than 15 probes.

In some or all aspects of the assay, the solid surface comprises a probe for detecting at least biomarker STY1479.

In some or all aspects of the assay, the solid surface consists essentially a probe for detecting biomarker STY1479 and a positive and a negative assay control.

We further provide a test strip for detecting the presence of a *Salmonella enterica* serotype *Typhi* indicating molecule in a sample, comprising: a non-specific binding region; and an analyte binding region comprising at least one first binding partner immobilized thereon, wherein the at least one first binding partner is selected from an antigen selected from proteins STY1364; STY2657; HCM2.0069c; HCM2.0043; HCM1.137; STY2386; STY1479; STY2454; STY2248; STY3709; STY2155; HCM1.213c; and STY0712 or one or more fragments thereof; wherein the analyte binding region is downstream of the sample fluid flow pathway relative to the non-specific binding region.

In some or all aspects of the test strip further comprises: a conjugate pad, which serves as a sample application component; an absorbent pad, which serves to draw the sample continuously through the device, wherein the materials of the membrane system form a single fluid flow pathway; and a porous or bibulous member in fluid communication with the absorbent pad and conjugate pad, which porous or bibulous member accommodates a liquid sample and contains the analyte binding region.

In some or all aspects of the test strip, it further comprises: a mobilization region containing a second binding partner, wherein: the second binding partner is mobilized upon contact with the sample; and the mobilization region is upstream of the analyte binding region.

In some or all aspects of the test strip, it further comprises: a control region containing a biomolecule that specifically binds the second biomarker binding partner, wherein: the control region is downstream of the analyte binding region.

In some or all aspects of the test strip the non-specific binding region contains a non-specific binding protein immobilized thereon; and the non-specific binding protein is selected from among BSA, methylated BSA, W632 and mouse IgG.

We also provide a kit comprising at least one antigen selected from STY1364; STY2657; HCM2.0069c; HCM2.0043; HCM1.137; STY2386; STY1479; STY2454; STY2248; STY3709; STY2155; HCM1.213c; STY0712 and any fragment or combination thereof optionally bound to a solid surface; a positive control corresponding to at least one human immunoglobulin; and at least one antibody against at least one human immunoglobulin.

In some or all aspects of the kit, the antigen is STY 1479.

In some or all aspects of the kit, it comprises no more than 20 antigen sets.

In some or all aspects of the kit, the kit comprises no more than 10 antigen sets.

In some or all aspects of the kit, the at least one human immunoglobulin comprises IgG.

We also provide a kit comprising at least one probe that is specific for a biomarker selected from or selected from the group consisting of STY1364; STY2657; HCM2.0069c; HCM2.0043; HCM1.137; STY2386; STY1479; STY2454; STY2248; STY3709; STY2155; HCM1.213c; and STY0712; a positive control corresponding to the biomarker selected from STY1364; STY2657; HCM2.0069c; HCM2.0043; HCM1.137; STY2386; STY1479; STY2454; STY2248; STY3709; STY2155; HCM1.213c; and STY0712; and a negative biological sample that does not comprise any one of the biomarkers STY1364; STY2657; HCM2.0069c; HCM2.0043; HCM1.137; STY2386; STY1479; STY2454; STY2248; STY3709; STY2155; HCM1.213c; or STY0712.

In some or all aspects of the kit, the kit consists essentially of a probe that is specific for biomarker STY1479, and a positive control comprising STY1479.

We provide a method for treatment of *S. Typhi* infection in an asymptomatic human subject comprising the steps of detecting *S. Typhi* infection from a biological sample taken from the asymptomatic human subject by detecting the presence of at least one immunoglobulin specific for a biomarker selected from STY1364; STY2657; HCM2.0069c; HCM2.0043; HCM1.137; STY2386; STY1479; STY2454; STY2248; STY3709; STY2155; HCM1.213c; or STY0712; and if/when the at least one immunoglobulin specific for the biomarker is detected then administering to the subject an antibiotic effective against S. Typhi; if/when the at least one biomarker is not detected then not administering the antibiotic to the human subject.

We provide a microfluidic device comprising at least one *S. Typhi* specific antigen selected from the group consisting of STY1364; STY2657; HCM2.0069c; HCM2.0043; HCM1.137; STY2386; STY1479; STY2454; STY2248; STY3709; STY2155; HCM1.213c; or STY0712 and any combination or fragment thereof.

We provide a composition comprising no more than 20 different antigen sets selected from or selected from the group consisting of STY1364; STY2657; HCM2.0069c; HCM2.0043; HCM1.137; STY2386; STY1479; STY2454; STY2248; STY3709; STY2155; HCM1.213c; STY0712 and fragments thereof and a solid support.

In some or all aspects of the composition, the composition comprises no more than 10 different antigen sets.

We provide a composition comprising at least one antibody against an isolated *S. Typhi* antigen selected from the group consisting of STY1364; STY2657; HCM2.0069c; HCM2.0043; HCM1.137; STY2386; STY1479; STY2454; STY2248; STY3709; STY2155; HCM1.213c; or STY0712 and any combination thereof.

Table 1 lists the proteins with IgG immunoreactivity in *S. Typhi* carriers compared to healthy typhoid-endemic zone controls who are not carriers in an immunoblot assay.

| STY Locus | Gene Name | Function | Seq ID No. |
|---|---|---|---|
| STY1364 | | Hypothetical periplasmic protein | 1 |
| STY2657 | xapB | Xanthosinepermease | 2 |
| HCM2.0069c | | Hypothetical protein | 3 |

-continued

| STY Locus | Gene Name | Function | Seq ID No. |
|---|---|---|---|
| HCM2.0043 | | Hypothetical protein | 4 |
| HCM1.137 | | Replication initiation protein | 5 |
| STY2386 | | Putative lipoprotein | 6 |
| STY1479 | | Possible ATP-binding protein | 7 |
| STY2454 | yejE | Putative binding-protein-dependent transporter | 8 |
| STY2248 | pduG | PduG protein | 9 |
| STY3709 | purH | Phosphoribosylaminoimidazolecarboxamideformyltransferase and IMP cyclohydrolase (bifunctional enzyme) | 10 |
| STY2155 | sirA | Invasion response-regulator | 11 |
| HCM1.213c | | Putative transposase | 12 |
| STY0712 | | Haemolysin-related protein | 13 |

EXAMPLES

Example 1

We applied an immunoscreening technique, in vivo-induced antigen technology (IVIAT), to identify potential biomarkers unique to *S. Typhi* chronic carriers. IVIAT identifies humorally immunogenic bacterial antigens expressed uniquely in vivo, and we hypothesized that *S. Typhi* surviving in the biliary tract of humans may express a distinct proteomic profile. In brief, we generated a 120,000 clone genomic inducible expression library of *S. Typhi* CT18 (500-1500 bp fragments) in *E. coli* BL21DE3, and screened the library against pooled sera of patients (pre-adsorbed with in vitro grown S. Typhi and *E. coli* BL21DE3) who had bile cultures positive for *S. Typhi* at the time of elective cholecystectomy in Kathmandu, Nepal. We identified and sub-cloned 268 genes of interest from our primary screen. Thus far, we have identified 50 proteins that are immunoreactive in *S. Typhi* carriers. Of these, 13 are not immunoreactive in healthy individuals from a typhoid endemic area (Dhaka, Bangladesh). Identified proteins included a number of putative membrane proteins, lipoproteins, and hemolysin-related proteins. We compared immunoreactivity to these proteins in patients whose biliary tract contained *S. Typhi* to responses in patients whose biliary tract did not contain S. Typhi, as well as to patients with acute typhoid fever and healthy controls residing in a typhoid endemic area. We identified a immunoreactive antigen in *Typhi* carriers: STY1479, a uncharacterized protein with an ATP-binding motif. A total of 7 of 10 (70%) chronic carriers, 0 of 8 bile culture negative controls (0%), 0 of 8 healthy Bangladeshis (0%), and 1 of 8 (12.5%) Bangladeshis with acute typhoid fever had an anti-STY1479 response.

Any of the 13 markers can be used in a diagnostic assay to detect asymptomatic *S. Typhi* carriers. One example of the useful markers is STY1479.

Patient and control sera: We enrolled individuals undergoing elective cholecystectomy in Kathmandu, Nepal. At the time of cholecystectomy, a venous sample was stored and a bile sample was taken for microbiologic analysis. Patients were categorized as *S. Typhi* carriers, *S. Paratyphi* A carriers, or cholecystectomy-controls based on bile culture results. Two additional groups of sera were obtained: (1) from 8 healthy Bangladeshi residents of Dhaka (a typhoid endemic area) enrolled at the International Centre for Diarrhoeal Disease Research, Bangladesh (icddr,b), and (2) convalescent sera of 8 Bangladeshi patients who presented to icddr,b with *S. Typhi* bacteremia.

IVIAT screening: We generated a 120,000 clone genomic inducible expression library of S. Typhi CT18 (500-1500 bp fragments) in *E. coli* BL21DE3, and screened the library against pooled sera of 5 cholecystectomy patients (pre-adsorbed with in vitro grown S. Typhi and *E. coli* BL21DE3) who had bile cultures positive for *S. Typhi*. We sequenced clones with higher IgG immunoreactivity compared to a control strain (*E. coli* BL21DE3 with empty vector), and we evaluated immunoreactivity of identified ORFs by cloning the entire predicted ORF into an inducible expression clone. To assess the degree of immunoreactivity of antigens identified by IVIAT within the pertinent general population, we screened immunoreactive clones against pooled sera of healthy Bangladeshis (pre-adsorbed with in vitro *E. coli* BL21DE3)

Detection of STY1479 and Vi-specific antibodies by ELISA: We further evaluated identified antigens using a modified ELISA assay. We coated plates with identified antigens that had been expressed using an *E. coli* in vitro transcription translation system (S30 T7 High-Yield Protein Expression system, Promega). Following identification of STY1479, we further assessed anti-IgG and IgA responses in 10 *S. Typhi* carriers, 3 *S. Paratyphi* carriers, 8 patients convalescing from acute typhoid infection (day 21 blood), and 8 healthy Bangladeshis (using 1:600 dilution of sera that had been pre-adsorbed with *E. coli* lysate). We detected bound antibody with anti-human IgG and IgA conjugated with horseradish peroxidase at a 1:1000 dilution, and measured peroxidase activity with Supersignal West Femto Chemiluminescent substrate (Pierce).

For evaluation of anti-Vi IgG and IgA responses, we coated ELISA plates with 200 ng/well of Vi antigen. We applied above sera at a 1:100 dilution, detected with anti-human IgG and IgA conjugated with horseradish peroxidase at a 1:1000 dilution, and measured peroxidase activity with the substrate 2,2-azinobis(ethylbenzthiazolinesulfonic acid).

Results: We identified 268 genes of interest from our primary screen, and subsequently sub-cloned each identified gene. In our initial immunoblot assay, we detected higher IgG immunoreactivity to 56 proteins in *S. Typhi* carriers compared to empty vector. Of these, 13 were more immunoreactive using blood of carriers versus healthy Bangladeshis, and these included a number of putative membrane proteins, lipoproteins, and hemolysin-related proteins (Table 1). STY1479, a possible ATP-binding protein, had the overall highest immunoreactivity compared to healthy endemic-zone control sera. In an ELISA format, we found significantly higher IgG immunoreactivity to STY1479 in *S. Typhi* carriers compared to bile culture-negative patients (p<0.0065) and Healthy Bangladeshis (p<0.0063); there was a trend towards statistical significance when compared to patients convalescing from acute typhoid infection (p=0.17). *S. Typhi* carriers had higher IgA immunoreactivity to STY1479 when compared to our two control groups. In our small subset of patients, an anti-STY1479 IgG response of >20 ELISA units had a sensitivity of 70% and a specificity of 100% compared to endemic zone healthy controls and cholecystectomy patients without detectable *S. Typhi*.

Since immune responses of Vi have been the best characterized diagnostic method for identifying *S. Typhi* carriers to date, we assessed the anti-Vi IgG and IgA responses in our patient panel. The sensitivity for anti-Vi IgG and IgA, were 50% and 70%, respectively. The background values for Vi in the controls were higher than those associated with STY1479.

Conclusion: We have identified an immunoreactive antigen in *S. Typhi* carriers, STY1479. In our small sample sized study, STY 1479 was more specific and as sensitive as the Vi antigen assay for the identification of *S. Typhi* carriers in typhoid endemic areas. Further evaluation of STY1479 could lead to the development of an improved diagnostic assay to detect asymptomatic *S. Typhi* carriers in typhoid endemic zones, and analysis of STY1479 could lead to improved understanding of *S. Typhi*'s survival within the biliary tracts of carriers.

Example 2

*Salmonella enterica* serotype *Typhi* can colonize and persist in the biliary tract of infected individual, resulting in an apparent state of asymptomatic chronic carriage. These chronic carriers act as persistent reservoirs of infection within a community and may introduce infection to susceptible individuals and new communities. Little is known about the interaction between the host and the pathogen in the biliary tract of chronic carriers, and there is currently no reliable diagnostic assay to identify asymptomatic *S. Typhi* carriage.

Methodology and Principal Findings

To study host-pathogen interactions in the biliary tract, we applied an immunoscreening technique called in vivo-induced antigen technology (IVIAT), to identify potential biomarkers unique to *S. Typhi* chronic carriers. IVIAT identifies humorally immunogenic bacterial antigens expressed uniquely in the in vivo environment, and we hypothesized that *S. Typhi* surviving in the biliary tract of humans may express a distinct proteomic profile. Thirteen *S. Typhi* antigens that were immunoreactive in carriers, but not in healthy individuals from a typhoid endemic area were identified. The identified antigens included a number of putative membrane proteins, lipoproteins, and hemolysin-related proteins. YncE (STY1479), an uncharacterized protein with an ATP-binding motif, gave prominent responses in our screen. The response to YncE in patients whose biliary tract contained *S. Typhi* was compared to responses in patients whose biliary tract did not contain *S. Typhi*, patients with acute typhoid fever, and healthy controls residingin a typhoid endemic area. Seven of 10 (70%) chronic carriers, 0 of 8 bile culture-negative controls (0%), 0 of 8 healthy Bangladeshis (0%), and 1 of 8 (12.5%) Bangladeshis with acute typhoid fever had detectable anti-YncE IgG in blood. IgA responses were also present.

*Salmonella enterica* serotype *Typhi* is the cause of typhoid fever and infects over 21 million individuals and causes 200,000 deaths each year. With adequate treatment, most patients recover from their acute stage of illness and clear infection. However, a small percentage of *S. Typhi* infected individuals develop a chronic but asymptomatic infection in the biliary tract that can persist for decades. Since *S. Typhi* is a human-restricted pathogen, chronic carriers may act as reservoirs of infection. Correctly identifying and treating asymptomatic chronic carriers could be critical for ultimate control of typhoid fever. Using an immunoscreening technique called in vivo-induced antigen technology (IVIAT), we have identified potential biomarkers unique to *S. Typhi* chronic carriers.

Use of these antigens provides a novel and improved diagnostic assays to detect asymptomatic *S. Typhi* carriers in typhoid endemic zones, and also provides an improved understanding of the pathogenesis of *S. Typhi* in the chronic carrier state.

*Salmonella enterica* serovars *Typhi* (*S. Typhi*) and Paratyphi A (*S. Paratyphi* A) are human-specific pathogens, and the predominant cause of enteric (typhoid) fever globally. Enteric fever affects over 21 million people each year, resulting in 200,000 deaths [Crump J A, Luby S P, Mintz E D (2004) The global burden of typhoid fever. Bull World Health Organ 82: 346-353]. Infection with *S. Typhi* and *S. Paratyphi* A usually begins with ingestion of contaminated water or food. The pathogens invade the gastrointestinal mucosa, translocate to the lymphoid follicles where they survive and replicate within macrophages, and then disseminate via the bloodstream to the liver, spleen, intestinal lymph nodes, bone marrow, and gallbladder [Monack D M, Mueller A, Falkow S (2004) Persistent bacterial infections: the interface of the pathogen and the host immune system. Nat Rev Microbiol 2: 747]. With adequate treatment, most patients recover from their acute stage of illness and clear infection. However, a small percentage of *S. Typhi* (and *S. Paratyphi* A) infected individuals develop a chronic, but apparently asymptomatic, infection in the biliary tract that can persist for decades [Gonzalez-Escobedo G, Marshall J M, Gunn J S (2011) Chronic and acute infection of the gall bladder by *Salmonella Typhi*: understanding the carrier state. Nat Rev Microbiol 9: 9-14; Levine M M, Black R E, *Lanata* C (1982) Precise estimation of the numbers of chronic carriers of *Salmonella typhi* in Santiago, Chile, an endemic area. J Infect Dis 146: 724-726; Crawford R W, Rosales-Reyes R, Ramirez-Aguilar Mde L, Chapa-Azuela O, Alpuche-Aranda C, et al (2010) Gallstones play a significant role in *Salmonella* spp. gallbladder colonization and carriage. Proc Natl Acad Sci USA 107: 4353-4358; Dongol S, Thompson C N, Clare S, Nga T V, Duy P T, et al (2012) The microbiological and clinical characteristics of invasive *Salmonella* in gallbladders from cholecystectomy patients in Kathmandu, Nepal. PLoS One 7: e47342]. The likelihood of this is not known, but it is estimated that chronic carriage can complicate perhaps 1-3% of acute infections [Parry C M, Wijedoru L, Arjyal A, Baker S (2011) The utility of diagnostic tests for enteric fever in endemic locations. Expert Rev Anti Infect Ther 9: 711-725].

Since *S. Typhi* and *S. Paratyphi* A are human-restricted pathogens, chronic carriers may act as reservoirs of infection within a community. They contribute to the transmission cycle through the intermittent shedding of bacteria in feces (especially in areas of low transmission [Lynch M F, Blanton E M, Bulens S, Polyak C, Vojdani J, et al (2009) Typhoid fever in the United States, 1999-2006. JAMA 302: 859-865] and may act as vehicles for introducing *S. Typhi* and *S. Paratyphi* A into previously uninfected communities. Therefore, correctly identifying and treating asymptomatic chronic carriers is critical for the long-term control of enteric fever. Currently, there is no reliable diagnostic assay to identify asymptomatic *S. Typhi* and *S. Paratyphi* A carriage. Bacterial stool culture has been used, yet is challenging due to the expense and logistics of obtaining multiple samples from patients, since shedding is typically low level and intermittent [Crawford R W, Rosales-Reyes R, Ramirez-Aguilar Mde L, Chapa-Azuela O, Alpuche-Aranda C, et al (2010) Gallstones play a significant role in *Salmonella* spp. gallbladder colonization and carriage. Proc Natl Acad Sci USA 107: 4353-4358]. Measurement of antibody responses to the *S. Typhi* capsular Vi antigen has been previously described as a potential method to detect chronic *S. Typhi* carriers [Parry C M, Wijedoru L, Arjyal A, Baker S (2011) The utility of diagnostic tests for enteric fever in endemic locations. Expert Rev Anti Infect Ther 9: 711-725]. In laboratory settings, IgG to the Vi antigen has been shown to have a sensitivity of 75% and specificity of >95% and has proven to complement other strategies in outbreak investigations [Parry C M, Wijedoru L, Arjyal A, Baker S (2011) The utility of diagnostic tests for enteric fever in endemic locations. Expert Rev Anti Infect Ther 9: 711-725; Nolan C M, Feeley J C, White P C, Jr, Hambie E A, Brown S L, et al (1980) Evaluation of a new assay for Vi antibody in chronic carriers of *Salmonella typhi*. J Clin Microbiol 12: 22-26; Losonsky G A, Ferreccio C, Kotloff K L, Kaintuck S, Robbins J B, et al (1987) Development and evaluation of an enzyme-linked immunosorbent assay for serum Vi antibodies for detection of chronic *Salmonella typhi* carriers. J Clin Microbiol 25:2266-2269; Nath G, Mauryal P, Gulati A K, Singh T B, Srivastava R, et al (2010) Comparison of Vi serology and nested PCR in diagnosis of chronic typhoid carriers in two different study populations in typhoid endemic area of India. Southeast Asian J Trop Med Public Health 41: 636-640]. However, its role in detecting asymptomatic carriers in a general endemic-zone population is unclear. In Chile, anti-Vi antibody responses had a sensitivity of 75% and specificity of 92%-97% for *S. Typhi* carriage; however, due to a low prevalence rate of carriage in the general population, its positive predictive value was only 8-17% [Lanata C F, Levine M M, Ristori C, Black R E, Jimenez L, et al (1983) Vi serology in detection of chronic *Salmonella typhi* carriers in an endemic area. Lancet 2: 441-443]. In Vietnam, a large community-based survey for anti-Vi antibodies demonstrated a 3% positivity rate in the population; however, *S. Typhi* was never detected in the stool of individuals identified by such anti-Vi screening [Gupta A, My Thanh N T, Olsen S J, Sivapalasingam S, My Trinh T T, et al (2006) Evaluation of community-based serologic screening for identification of chronic *Salmonella typhi* carriers in Vietnam. Int J Infect Dis 10: 309-314].

Understanding the mechanisms involved in development and persistence of the carrier state facilitates the development of improved diagnostic assays and therapeutic approaches for *S. Typhi* carriage. Currently, little is known about host-pathogen interactions in the biliary tract of chronic human carriers. Much of what is known about biliary carriage has been extrapolated from in vitro and murine studies with S. *Typhimurium*, which causes an enteric fever-like illness in mice [Crawford R W, et al (2010) Proc Natl Acad Sci USA 107: 4353-4358]. From these animal studies and a complimentary study in humans, we know that gallstones facilitate *S. Typhi* carriage [Crawford R W, et al (2010) Proc Natl Acad Sci USA 107: 4353-4358]. In the presence of bile, the bacterium regulates the expression of genes that allow it to colonize and persist in the gallbladder through formation of biofilms that mediate resistance against host defenses [Crawford R W, Gibson D L, Kay W W, Gunn J S (2008) Identification of a bile-induced exopolysaccharide required for *Salmonella* biofilm formation on gallstone surfaces. Infect Immun 76: 5341-5349; Prouty A M, Brodsky I E, Manos J, Belas R, Falkow S, et al (2004) Transcriptional regulation of *Salmonella enterica* serovar *Typhimurium* genes by bile. FEMS Immunol Med Microbiol 41: 177-185]. There are likely other niches of persistent infection outside of the gallbladder, including the biliary tree, liver, and mesenteric lymph nodes. This is suggested by the observation that although cholecystectomy increases cure rates, it does not always result in clearance of the pathogen in humans [Ristori C, Rodriguez H, Vicent P, Ferreccio C, Garcia J, et al (1982) Persistence of the *Salmonella typhi*-paratyphi carrier state after gallbladder removal. Bull Pan Am Health Organ 16: 361-366]. In a murine model of *Salmonella* chronic infection, S. *Typhimurium* infection in Slc11a1 (Nramp1) wild-type mice demonstrated that the most common site of persistent infection was in hemophagocytic macrophages within mesenteric lymph nodes [Monack D M, Mueller A, Falkow S (2004) Nat Rev Microbiol 2: 747; Monack D M, Bouley D M, Falkow S (2004) *Salmonella typhimurium* persists within macrophages in the mesenteric lymph nodes of chronically infected Nramp 1+/+mice and can be reactivated by IFNgamma neutralization. J Exp Med 199: 231-241; Nix R N, Altschuler S E, Henson P M, Detweiler C S (2007) Hemophagocytic macrophages harbor *Salmonella enterica* during persistent infection. PLoS Pathog 3: e193.]. To advance our understanding of *Salmonella* pathogenesis of the chronic carrier state, and identify potential biomarkers unique to *S. Typhi* chronic carriers, we applied an immunoscreening technique called in vivo-induced antigen technology (IVIAT) [Harris J B, Baresch-Bernal A, Rollins S M, Alam A, LaRocque R C, et al (2006) Identification of in vivo-induced bacterial protein antigens during human infection with *Salmonella enterica* serovar *Typhi*. Infect Immun 74: 5161-5168; Rollins S M, Peppercorn A, Young J S, Drysdale M, Baresch A, et al (2008) Application of in vivo induced antigen technology (IVIAT) to *Bacillus anthracis*. PLoS One 3: e1824; Hang L, John M, Asaduzzaman M, Bridges E A, Vanderspurt C, et al (2003) Use of in vivo-induced antigen technology (IVIAT) to identify genes uniquely expressed during human infection with *Vibrio cholera*. Proc Natl Acad Sci USA 100: 8508-8513]. IVIAT identifies humorally immunogenic bacterial antigens expressed in vivo and not in bacteria grown in standard laboratory conditions. We hypothesized that *S. Typhi* surviving in the biliary tract of humans may express a proteomic profile distinct from that expressed in bacteria grown using standard in vitro conditions or during acute infection.

This study was approved by the human studies committees of the involved research institutions: Massachusetts General Hospital, International Centre of Diarrheal Disease Research, Bangladesh (icddr,b), Patan Hospital, The Nepal Health Research Council, and the Oxford Tropical Research Ethics Committee. The study was conducted according to the principles expressed in the Declaration of Helsinki/Belmont Report, and informed written consent was obtained from adult participants and from guardians of children prior to study participation.

Bacterial strains, plasmids, and media. *Salmonella enterica* serotype *Typhi* strain CT18 [Parkhill J, Dougan G, James K D, Thomson N R, Pickard D, et al (2001) Complete genome sequence of a multiple drug resistant *Salmonella enterica* serovar *Typhi* CT18. Nature 413: 848-852] was obtained from the *Salmonella* Genetic Stock Centre (Calgary, Alberta, Canada). Genomic DNA from this strain was used to construct a genomic inducible expression library in host strain *Escherichia coli* strain B21(DE3). Bacterial strains were grown in Luria-Bertani (LB) media (with 50

µg/mlkanamycin for clones containing pET30 constructs) and maintained at −80° C. in LB broth containing 15% glycerol.

Patient and control sera. Individuals undergoing elective cholecystectomy in Kathmandu, Nepal were enrolled. At the time of cholecystectomy, a venous blood sample was stored and a bile sample was taken for microbiologic analysis as previously described [Dongol S, et al (2012) PLoS One 7: e47342]. Patients were categorized as (1) *S. Typhi* carriers if their bile culture was positive for *S. Typhi*; (2) *S. Paratyphi* A carriers if their bile culture was positive for *S. Paratyphi* A, or (3) cholecystectomy controls if their bile cultures were negative for any organism. Sera samples were also obtained from the following groups: (1) healthy Bangladeshi residents of Dhaka (a typhoid endemic area) enrolled at the International Centre for Diarrhoeal Disease Research, Bangladesh (icddr,b); and (2) acute (day 0-3) and convalescent sera (day 14-28) of Bangladeshi patients who presented to icddr,b with *S. Typhi* bacteremia [Charles R C, Sheikh A, Krastins B, Harris J B, Bhuiyan M S, et al (2010) Characterization of anti-*Salmonella enterica* serotype *Typhi* antibody responses in bacteremic Bangladeshi patients by an immunoaffinity proteomics-based technology. Clin Vaccine Immunol 17: 1188-1195; Sheikh A, Charles R C, Sharmeen N, Rollins S M, Harris J B, et al (2011) In vivo expression of *Salmonella enterica* serotype *Typhi* genes in the blood of patients with typhoid fever in Bangladesh. PLoS Negl Trop Dis 5: e1419; Sheikh A, Bhuiyan M S, Khanam F, Chowdhury F, Saha A, et al (2009) *Salmonella enterica* serovar *Typhi*-specific immunoglobulin A antibody responses in plasma and antibody in lymphocyte supernatant specimens in Bangladeshi patients with suspected typhoid fever. Clin Vaccine Immunol 16: 1587-1594].

Construction of genomic inducible expression library. Genomic DNA was purified from *S. Typhi* strain CT18 using a Genomic DNA Isolation kit (Qiagen, Valencia, Ca), sheared using a Covaris sonicatior (Woburn, Ma) optimized to generate 0.5-1.5 kb DNA fragments, and resulting fragments were gel purified using the Qiagen Qiaquick Gel Extraction kit. After terminal overhangs were removed using End-It® DNA end-repair kit (Epicenter Biotechnologies, Madison, Wis.), the blunt-end products were ligated into pET-30c vectors (Novagen, San Diego, Calif.) that had been digested with EcoRV and treated with calf intestinal alkaline phosphatase. The library was electroporated into *E. coli* DH5α and bacteria were plated onto selective LB media containing kanamycin.

After overnight incubation at 37° C., the plates were scraped and the plasmid DNA from collected colonies was recovered using Qiagen MINIPREP® kit. EcoRl and Kpnl digestion was performed on a random sample of plasmids, and an insertion frequency greater than 80% and insert size between 500 to 1500 bp was verified. The plasmid DNA mixture was electroporated into *E. coli* BL21 (DE3), and collected colonies were stored in LB broth containing 15% glycerol.

Screening for antigens uniquely expressed in vivo in *S. Typhi* carriers. Convalescentsera of 5 patients with bile cultures positive for *S. Typhi* were pooled, and adsorbed with in vitro grown *S. Typhi* strain CT18 and *E. coli* BL21 (DE3) [-Harris J B, Baresch-Bernal A, Rollins S M, Alam A, LaRocque R C, et al (2006) Identification of in vivo-induced bacterial protein antigens during human infection with *Salmonella enterica* serovar *Typhi*. Infect Immun 74: 5161-5168]. Immunoblot techniques were used as previously described [Harris J B, et al (2006) Infect Immun 74: 5161-5168]. Briefly, the genomic library was plated on LB plates containing kanamycin to obtain a colony density of approximately 500 to 1000 clones per plate. After overnight incubation at 37° C., the resultant colonies were lifted off the plate using nitrocellulose membranes, and then the membranes were placed on LB media containing kanamycin and 1 mM isopropyl-β-D-thiogalactopyranoside for 4 hours at 37° C. to induce transcription of insert DNA.

Membranes were exposed to chloroform-soaked blotting paper to lyse bacteria, blocked for 1 hr using 5% milk in PBS with 0.25% Tween-20 (PBS/Tween), washed five times in PBS/Tween, and then incubated overnight with adsorbed sera at 1:10,000 dilution. After membranes were washed 3 times with PBS/Tween, immunoreactive clones were detected using anti-human IgG conjugated to horseradish peroxidase (MP Biomedicals/Cappel, Aurora, Ohio) at a 1:20,000 dilution, and immunoblots were developed with an enhanced chemiluminescence (ECL) kit (Amersham, Piscataway, N.J.). Reactive clones were recovered from the master plates and saved as frozen glycerol stocks.

To confirm immunoreactive clones, secondary screening was performed comparing IgG immunoreactivity of the clones against *E. coli* BL21DE3 with an empty pET30c vector. Inserts of confirmed clones were sequenced to identify gene insert.

Constructs designed to express the full length native protein were generated by amplifying the entire ORF of identified genes by PCR, and cloning these amplicons into pET30c as NdeI and NotI inserts. Immunoreactivity of these full ORF clones was compared to *E. coli* BL21DE3 with an empty pET30c vector. To assess immunoreactivity of identified antigens among the pertinent general population, immunoreactive clones were also screened using pooled sera of individuals living in a typhoid endemic area (Bangladesh). These sera were pre-adsorbed against in vitro grown *E. coli* BL21DE3, as described above, to reduce background reactivity against the host strain.

Functional classifications of identified proteins were assigned using published articles and available protein information resources, including J. Craig Venter Institute annotations (available, e.g., at the world wide web address Hyper-Text Transfer Protocol://cmrjcvi.org/tigr-scripts/CMR/CmrHomePage.cgi) and Pfam 26.0 (available e.g., at the world wide web address Hyper-Text Transfer Protocol://pfam.sanger.ac.uk/).

Purification of YncE. YncE (STY1479) was PCR-amplified from *S. Typhi* strain CT18 and the product was cloned into Gateway vector pDONR221 using BP reaction kit according to manufacturer's instructions (Invitrogen). The full length sequence was verified and transferred from pDONR221 into the Gateway expression vector pDEST17 using LR reaction kit (Invitrogen) generating pDEST17His6-yncE ("His6" disclosed as SEQ ID NO: 27). The reaction product was transformed first into *E. coli* DH5α, and then the recovered plasmid was transformed into the expression strain BL21AI. To overproduce His6-YncE ("His6" disclosed as SEQ ID NO: 27), *E. coli* BL21AI (pDEST17His6-yncE) ("His6" disclosed as SEQ ID NO: 27) was grown in 250 mL LB broth containing ampicillin at 37° C. until OD600 0.6, and then expression of his6-yncE ("His6" disclosed as SEQ ID NO: 27) was induced by the addition of L(+) arabinose (0.2%). After 4 hours, the pellet was harvested by centrifugation, and the cells were lysed by sonication after resuspension in 15 mL lysis buffer (50 mM Tris Hcl, 5% glycerol, 0.1M NaCl pH 8) containing 100 ug/mllysozyme. Following centrifugation, the pellet was washed in lysis buffer with and without 1% Triton X-100, and the pellet was resuspended in 10 mL of 8M urea, 50 mM NaH2PO4 and 300 mM NaCl (pH 7.4). His6-YncE ("His6" disclosed as SEQ ID NO: 27) was purified by HisPur Cobalt Resin (ThermoScientific, Rockford, Ill.) under denaturing conditions per the manufacturer's instructions. His6-YncE ("His6" disclosed as SEQ ID NO: 27) was then refolded by dialysis into 25 mM Tris-HCL 0.15M NaCl, pH 8.0 using decreasing concentrations of urea. Product purity was assessed by polyacrylamide gel electrophoresis and Coomassie staining, and product identity was assessed by Mass spectrometry analysis. Protein concentration was determined via Coomassie (Bradford) Protein Assay Kit (ThermoScientific, Rockford, Ill.).

Evaluation of serum IgG and IgA responses to YncE and *S. Typhi* capsular Vi antigen. To further characterize immunoreactivity of the antigen with the most prominent immunoreactivity in our initial screening, anti-YncE (STY1479) IgG and IgA responses were measured in the sera of 10 *S. Typhi* carriers, 3 *S. Paratyphi* A carriers, 8 patients at acute (day 0-3) and convalescent phase (day 14-28) of typhoid fever with confirmed *S. Typhi* bacteremia, 8 Nepalese controls undergoing elective cholecystectomy with negative bile cultures and 8 healthy Bangladeshis. Plates were coated with 100 ng/well of YncE and then sera were added at a 1:200 dilution. Bound antibody was detected with anti-human IgG or IgA conjugated with horseradish peroxidase (Jackson Laboratories, Bar Harbor, Me.) at a 1:1000 dilution, and peroxidase activity was measured with the substrate 2,2-azinobis (ethylbenzthiazolinesulfonic acid). To compare across plates, readings of samples was divided by readings of an in-house pooled standard, multiplied by 100, and results were expressed as ELISA units (EU). The Mann-Whitney U test was used to compare differences between groups.

For evaluation of anti-Vi IgG and IgA responses, ELISA plates were coated with 200 ng/well of Vi antigen (Sanofi Pasteur, Lyon, France). The above sera were applied at a 1:100 dilution, and bound antibody was detected with anti-human IgG and IgA conjugated with horseradish peroxidase at a 1:1000 dilution. Peroxidase activity was measured with the substrate 2,2-azinobis (ethylbenzthiazolinesulfonic acid). Differences between groups were assessed using the Mann-Whitney U test.

*S. Typhi* antigens identified by IVIAT. In the primary screen of over 120,000 clones, 565 clones were identified as immunogenic; 210 were confirmed by secondary screening.

Sequence analysis of these inserts (many of which carried multiple potentially expressible ORFs) revealed 268 genes of interest with over 20% of genes identified multiple times, supporting validity of their identification and saturation of library screening. We subsequently sub-cloned the full coding sequences of 235 genes into individual expression plasmids, and identified 56 proteins with prominent IgG immunoreactivity using *S. Typhi* carrier sera, comparing immunoreactivity of expression clones to a clone containing an empty vector. Forty-eight of the identified genes are encoded on the chromosome of *S. Typhi*, five (5) are encoded on the drug resistance plasmid pHCM1, and 3 on cryptic plasmid pHCM2. The most highly represented functional groups included proteins of unknown function and those involved in transport and binding, synthesis or salvage of ribonucleotides, and energy metabolism.

To assess the degree of immunoreactivity of antigens identified by IVIAT within the pertinent endemic-zone population, we screened the 56 immunoreactive clones against pooled sera of individuals living in a *S. Typhi* endemic area (Bangladeshi residents of Dhaka) [Brooks W A, Hossain A, Goswami D, Nahar K, Alam K, et al (2005) Bacteremic typhoid fever in children in an urban slum, Bangladesh. Emerg Infect Dis 11: 326-329]. Of these 56 proteins, 13 proteins had more prominent immunoreactivity when screened with sera of *S. Typhi* carriers compared to sera of healthy Bangladeshis. These 13 proteins included a number of putative membrane proteins, lipoproteins, and hemolysin-related proteins (Table 1). YncE, a possible ATP-binding protein, had the overall highest differential immunoreactivity compared to healthy endemic-zone control sera in our immunoblot assay.

Anti-YncE serum responses as a diagnostic biomarker for asymptomatic *S. Typhi* carriage. To further characterize whether the immunoreactivity to YncE in *S. Typhi* carriers was specific, we also evaluated the immunoreactivity to YncE using sera of 5 groups of individuals: (1) *S. Typhi* carriers, (2) patients at the acute and convalescent phase of typhoid fever, (3) *S. Paratyphi* A carriers, (4) individuals who underwent cholecystectomy in Nepal whose bile cultures were negative for any pathogen, and (5) healthy controls from a typhoid endemic area (Dhaka, Bangladesh). We found significantly higher IgG immunoreactivity to YncE in *S. Typhi* carriers compared to bile culture-negative patients (p=0.0205), healthy Bangladeshis (p=0.0005), and patients at the acute and convalescent phases of typhoid infection (p=0.0044 and p=0.0266, respectively); there was a trend toward statistical significance when compared to *S. Paratyphi* A carriers (p=0.22) (FIG. 1A). Of the 10 *S. Typhi* carriers, 7 (70%) had an anti-YncE IgG response (ELISA unit >100). None of 8 bile culture negative controls (0%), 0 of 8 healthy Bangladeshis (0%), 0 of 3 *S. Paratyphi* A carriers (0%) and 1 of 8 (12.5%) Bangladeshis at the acute and convalescent phase of *S. Typhi* had an anti-YncE IgG response. Thus, in our small subset of patients, using a cut-off value of >100 Elisa Units (EU), anti-YncE IgG had a sensitivity of 70%, and specificity of 100% when using endemic zone healthy individuals and cholecystectomy patients without detectable *S. Typhi* as controls. The specificity decreased to 95% if we included patients with acute typhoid fever.

Figure 3:
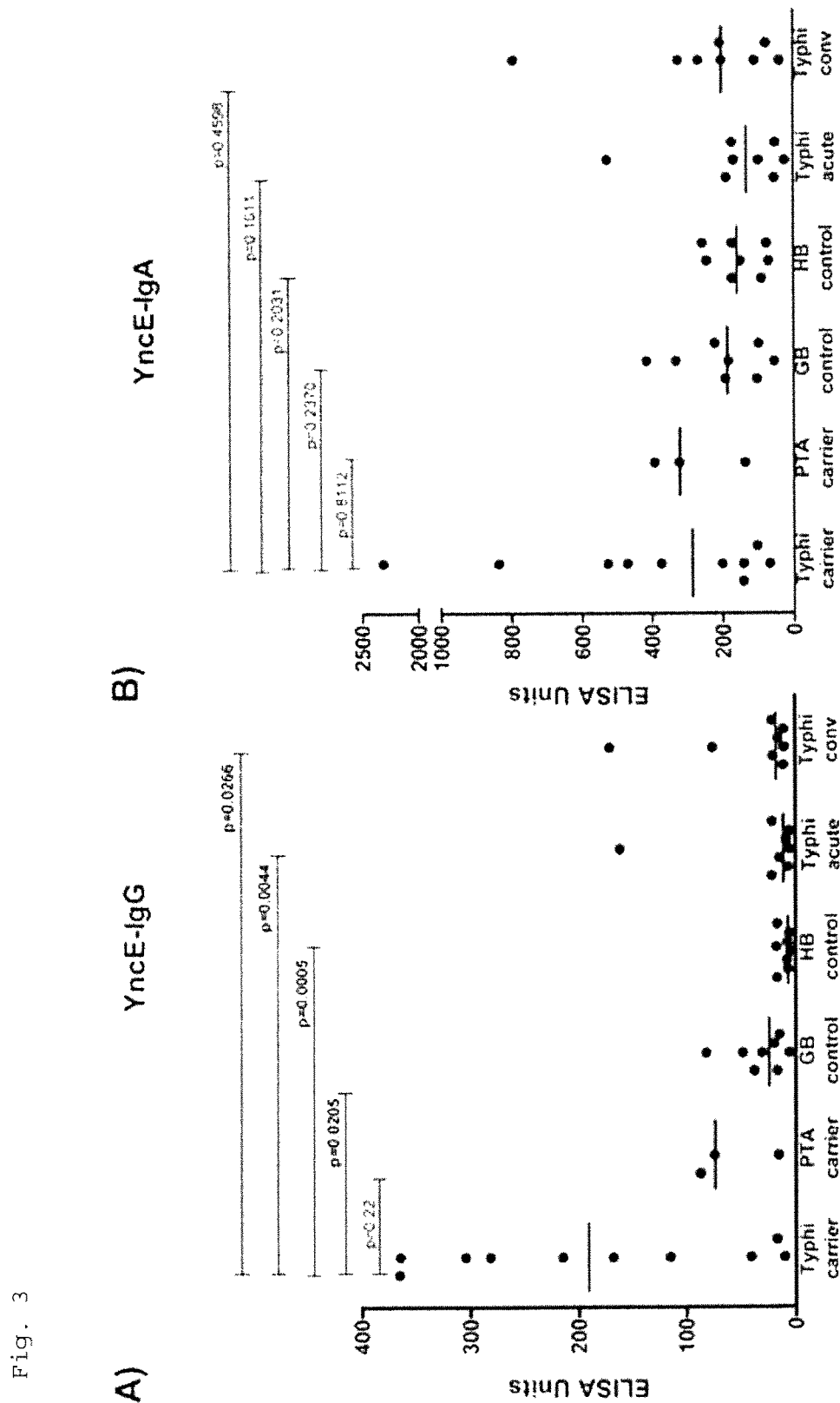
FIG. 3 shows an anti-YncE IgG (FIG. 3A) and IgA (FIG. 3B) responses in S. Typhi carriers (Typhi carrier), S. Paratyphi A Carriers (PTA carrier), Nepalese controls undergoing elective cholecystectomy with negative bile cultures (GB control), Healthy Bangladeshi controls (HB control), and patients at the day 0-3 acute (Typhi acute) and day 14-28 convalescent phase (Typhi cony) of typhoid fever with confirmed S. Typhi bacteremia.

*S. Typhi* carriers also had a higher IgA immunoreactivity to YncE compared to our two control groups: bile culture-negative patients (p=0.2370) and healthy Bangladeshis (p=0.2031) (FIG. 3B).

There was no significant difference between the IgA immunoreactivity to YncE in *S. Typhi* carriers in comparison to patients convalescing from acute typhoid infection or *S. Paratyphi* A carriers.

Figure 4:
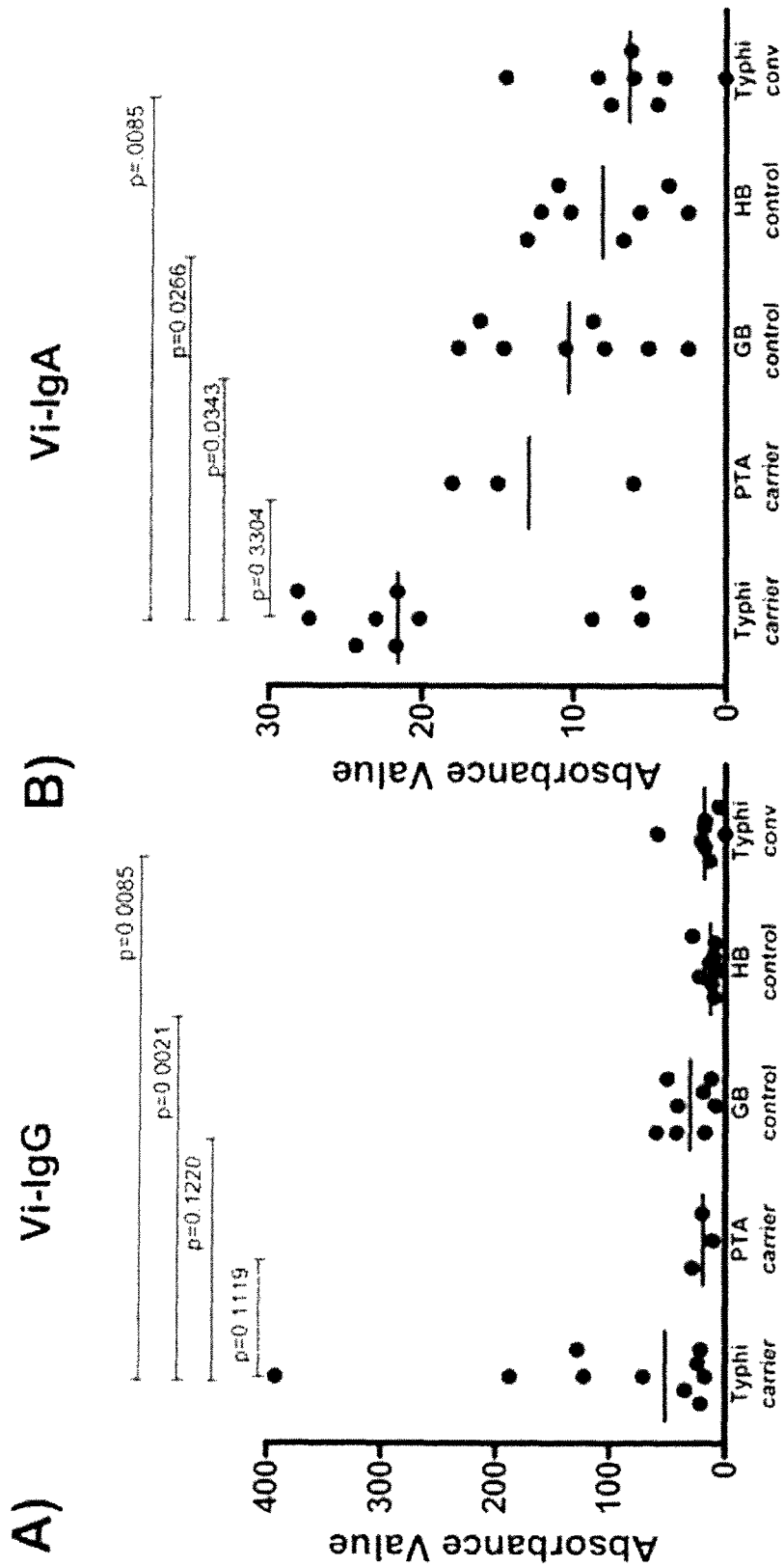
FIG. 4 shows an anti-Vi antigen IgG (FIG. 4A) and IgA (FIG. 4B) responses were evaluated in S. Typhi Carriers (Typhi carrier), S. Paratyphi A Carriers (PTA carrier), Nepalese controls undergoing elective cholecystectomy with negative bile cultures (GB control), healthy Bangladeshi controls (HB control), and day 14-28 convalescent phase (Typhi cony) of typhoid fever with confirmed S. Typhi bacteremia.

Comparison with anti-Vi serum responses. Since immune responses to *S. Typhi* Vi antigen have been the best characterized diagnostic method for identifying *S. Typhi* carriers to date, we also assessed the anti-Vi IgG and IgA responses in the same cohort of patients. We found significantly higher IgG immunoreactivity to Vi antigen in *S. Typhi* carriers compared to healthy Bangladeshis (p=0.0021) and patients convalescing from acute typhoid infection (p=0.0085) (FIG. 4A). There was a trend toward statistical significance when the immunoreactivity of *S. Typhi* carriers to Vi antigen was compared to bile culture-negative patients (p=0.12) and *S. Paratyphi* A carriers (p=0.11) (FIG. 4A). In our evaluation of IgA anti-Vi responses, we did find a significant difference in the immunoreactivity of *S. Typhi* carriers compared to bile culture negative patients (p=0.0343), healthy Bangladeshis (p=0.0266), and patients convalescing from acute typhoid infection (p=0.0085) (FIG. 4B). There was no significant difference in immune responses between *S. Typhi* carriers and *S. Paratyphi* A carriers. The sensitivity for anti-Vi IgG and IgA was 50% (cutoff value >65 EU) and 70% (cutoff value >20 EU), respectively. The specificity was 100%, although the background values for Vi in the controls were higher than those associated with YncE.

Combined YncE and Vi antibody measurements for the detection of *S. Typhi* carriers. In our analysis, using a cut-off value of >100 EU of anti YncE IgG and/or >20 EU anti-Vi IgA, we could identify 9 out 10 *S. Typhi* carriers. There was no added benefit seen when pairing anti-YncE responses with anti-Vi IgG.

DISCUSSION

In our immunoscreen using IVIAT, we were able to identify 56 immunogenic *S. Typhi* proteins using the sera of *S. Typhi* carriers. Of these, 13 had higher immunoreactivity when screened with *S. Typhi* carrier sera compared to sera of endemic zone residents. These proteins represent a working list of candidate diagnostic biomarkers of asymptomatic *S. Typhi* carriage and their analysis may further our understanding of survival adaptations of *S. Typhi* in chronic carriers.

Human epidemiologic studies as well as murine models of *S. Typhi* carriage suggest that gallstones facilitate the development of the chronic carrier state [Crawford R W, et al (2010) Proc Natl Acad Sci USA 107: 4353-4358]. In support of this, we identified SirA in our IVIAT screen, which is part of the two-component response regulator SirA-BarA [Altier C, Suyemoto M, Ruiz A I, Burnham K D, Maurer R (2000) Characterization of two novel regulatory genes affecting *Salmonella* invasion gene expression. Mol Microbiol 35: 635-646]. In *S. Typhimurium*, this regulator plays a role in the down-regulation of genes involved in invasion (i.e. *Salmonella* Pathogenicity Island-1) when the bacterium is in the presence of bile [Prouty A M, Gunn J S (2000) *Salmonella enterica* serovar *Typhimurium* invasion is repressed in the presence of bile. Infect Immun 68: 6763-6769], and mutations in sirA result in decreased biofilm formation on plastic surfaces [Prouty A M, Gunn J S (2000) Infect Immun 68: 6763-6769]. The role SirA may play in human or murine *Salmonella* carriage, or why a cytoplasmic regulatory protein generated a humoral response, has yet to be characterized. Other proteins identified in the IVIAT screen may also affect carriage in the presence of gallstones.

Although *S. Typhi* may persist in the gallbladder in association with gallstones [Gonzalez-Escobedo G, Marshall J M, Gunn J S (2011) Nat Rev Microbiol 9: 9-14], *S. Typhi* likely has other niches of infection, including the gallbladder epithelium, biliary tree, and in macrophages of mesenteric lymph nodes [Monack D M, Mueller A, Falkow S (2004) Nat Rev Microbiol 2: 747; Gonzalez-Escobedo G, Marshall J M, Gunn J S (2011) Nat Rev Microbiol 9: 9-14; Crawford R W, et al (2010) Proc Natl Acad Sci USA 107: 4353-4358; Ristori C., et al (1982Bull Pan Am Health Organ 16: 361-366; Monack D M, Bouley D M, Falkow S (2004) J Exp Med 199: 231-241; Nix R N, Altschuler S E, Henson P M, Detweiler C S (2007) PLoS Pathog 3: e193]. Proteins identified in our screen may play a role in persistence of *S. Typhi* within host cells or the stringent environment of bile. For instance, YejE is a putative permease that is thought to be a component of a putative ABC transporter system. YejE plays a role in survival within epithelial cells and in antimicrobial peptide resistance [Eswarappa S M, Panguluri K K, Hensel M, Chakravortty D (2008) The yejABEF operon of *Salmonella* confers resistance to antimicrobial peptides and contributes to its virulence. Microbiology 154: 666-678]. In both *S. Typhi* and *S. Typhimurium*, yejE expression is upregulated inside host macrophages [Eriksson S, Lucchini S, Thompson A, Rhen M, Hinton J C (2003) Unravelling the biology of macrophage infection by gene expression profiling of intracellular *Salmonella enterica*. Mol Microbiol 47: 103-118; Faucher S P, Porwollik S, Dozois C M, McClelland M, Daigle F (2006) Transcriptome of *Salmonella enterica* serovar *Typhi* within macrophages revealed through the selective capture of transcribed sequences. Proc Natl Acad Sci USA 103: 1906-1911]. PduG is a protein encoded within the pdu operon that is part of the coenzyme B12-dependent 1,2-propranediol utilization pathway [Conner C P, Heithoff D M, Julio S M, Sinsheimer R L, Mahan M J (1998) Differential patterns of acquired virulence genes distinguish *Salmonella* strains. Proc Natl Acad Sci USA 95: 4641-4645]. This operon is upregulated during acute *S. Typhi* and *S. Paratyphi* A infection in humans [Sheikh A, et al (2011) PLoS Negl Trop Dis 5: e1419; Sheikh A, Charles R C, Rollins S M, Harris J B, Bhuiyan M S, et al (2010) Analysis of *Salmonella enterica* serotype Paratyphi A gene expression in the blood of bacteremic patients in Bangladesh. PLoS Negl Trop Dis 4: e908], and may be associated with use of alternative carbon sources in the nutrient-limited environment of the *Salmonella*-containing vacuole within host cells [Conner C P, et al. (1998) Proc Natl Acad Sci USA 95: 4641-4645]. We also identified PurH and XapB, which are proteins involved in purine biosynthesis and acquisition, respectively, by functional classification. In *S. Typhimurium*, PurH is associated with virulence [McFarland W C, Stocker B A (1987) Effect of different purine auxotrophic mutations on mouse-virulence of a Vi-positive strain of *Salmonella* dublin and of two strains of *Salmonella typhimurium*. Microb Pathog 3: 129-141], and we have previously shown that genes involved in purine synthesis are upregulated during acute typhoid infection in humans [Sheikh A, et al (2011) PLoS Negl Trop Dis 5: e1419]. CorC is a hemolysin-related protein involved in magnesium and cobalt efflux, and is part of the CorA transporter system containing CorA-D [Gibson M M, Bagga D A, Miller C G, Maguire M E (1991) Magnesium transport in *Salmonella typhimurium*: the influence of new mutations conferring Co2+ resistance on the CorA Mg2+ transport system. Mol Microbiol 5: 2753-2762]. CorA, with associated proteins, is required for efflux of Mg2+[Gibson M M, et al., (1991) Mol Microbiol 5: 2753-2762]. CorA is required for *S. Typhimurium* virulence [Papp-Wallace K M, Nartea M, Kehres D G, Porwollik S, McClelland M, et al (2008) The CorA Mg2+ channel is required for the virulence of *Salmonella enterica* serovar *Typhimurium*. J Bacteriol 190: 6517-6523], and corA is expressed by *S. Typhi* during acute human infection [Sheikh A, et al (2011) PLoS Negl Trop Dis 5: e1419]. However, while some information is known regarding the above mentioned *Salmonella* carrier-specific antigens, their potential role in carriage is presently unclear.

The majority of the genes identified by IVIAT encode for proteins with putative or unknown function. For example, STY2386 is an uncharacterized lipoprotein found uniquely in *Salmonella*. STY1364 is a hypothetical periplasmic protein in *S. Typhi* and *S. Paratyphi* A, and is rarely found in other *Salmonella* spp. STY1364 belongs to the structural classification of bacterial enterotoxins and is a subtilase cytotoxin subunit B-like protein. We previously identified STY1364 in *S. Typhi* infected patients using a separate immunoscreening technology (immunoaffinity proteomic-based technology, IPT) [Charles R C, et al (2010) Clin Vaccine Immunol 17: 1188-1195].

In our screening, YncE (STY1479) was the most immunoreactive antigen identified, and we thus focused our more detailed analysis of immunoreactivity on this antigen. YncE has a putative N-terminal signal sequence suggestive of export, with ATP and DNA-binding domains. yncE is present in a number of Salmonella spp., and has orthologs in a number of other Gram-negative enteric organisms, including Escherichia coli, Citrobacter spp, and Shigella spp. In E. coli, YncE is secreted into the periplasm via the Sec-dependent pathway [Baars L, Ytterberg A J, Drew D, Wagner S, Thilo C, et al (2006) Defining the role of the Escherichia coli chaperone SecB using comparative proteomics. J Biol Chem 281: 10024-10034], and its expression is induced under iron restricted conditions when repression by the Fur protein is relieved [McHugh J P, Rodriguez-Quinones F, Abdul-Tehrani H, Svistunenko D A, Poole R K, eta!(2003) Global iron-dependent gene regulation in Escherichia coli. A new mechanism for iron homeostasis. J Biol Chern 278: 29478-29486]. Its role in the pathogenesis of Salmonella infection has yet to be characterized. However our results suggest that it may be involved in long-term persistence of the bacterium in chronic carriers In our analysis, we show that S. Typhi carriers have an IgG response to YncE that is not present in bile culture-negative controls in Nepal or healthy controls in Bangladesh. A similar trend was seen for IgA as well. One patient convalescing from acute typhoid infection had a detectable IgG anti-YncE response, and another had an IgA response. This may suggest that anti-YncE responses occur during acute disease; however, it should be noted that we do not know the current or future carrier status of the acute typhoid patients, and an elevated level of YncE during an episode of typhoid fever may represent an acute on chronic infection, or may be a marker of future progression to the chronic carrier state.

All of the identified genes except three (xapB and the two genes encoded on the cryptic plasmid pHCM2) are present in the genome of S. Paratyphi A. It is interesting then, that we did not see an IgG or IgA immune response to YncE in S. Paratyphi A carriers. This finding suggests that S. Typhi and S. Paratyphi A use different strategies to persist in chronic carriers, that expression of YncE may be distinct in these two organisms.

Despite this, in our cohort of patients, measurement of anti-YncE IgG responses did appear to be both sensitive and specific for identifying asymptomatic chronic S. Typhi carriers.

The trending higher anti-YncE IgA levels in S. Typhi carriers than in control groups, that information could support a salivary diagnostic to facilitate community-based screening for carriage.

The other antigens identified in our IVIAT analysis may also be useful diagnostic biomarkers of S. Typhi carriage, and the sensitivity of carrier detection may be improved when responses against these or anti-Vi responses are paired with responses to YncE.

For example, in our analysis, using a cut-off value of >100 EU of anti YncE IgG and/or >20 EU anti-Vi IgA, we could identify 9 out 10 S. Typhi carriers. There was no added benefit seen when pairing anti-YncE responses with anti-Vi IgG. Another potential pairing could include a marker of biliary tract inflammation such as elevated bilirubin values, since S. Typhi carriage is often associated with chronic inflammation of the gallbladder [Crawford R W, et al (2010) Proc Natl Acad Sci USA 107: 4353-4358]. We did not assess this parameter in this study.

While our study included a limited number of patients, it should be noted that it is the largest study involving immunoproteomic screening and pilot confirmation of the carriage state that includes appropriate control groups.

We also note that IVIAT identifies proteins that are uniquely expressed in vivo compared to standard in vitro culturing, and that also induce an antibody response. Proteins that induce cellular responses and/or that are expressed both in vivo and in vitro may also play a role in the pathogenesis of chronic carriage and serve as useful biomarkers for asymptomatic carriage. In addition, altering in vitro culturing conditions may also change the expression profile of S. Typhi, thereby changing the comparison groups. In addition, IVIAT does not identify non-protein antigens that may also be useful in diagnostic assays.

However, we have used IVIAT to identify a subset of immunoreactive antigens in S. Typhi carriers, including YncE.

We claim:

1. A microfluidic device comprising:
    at least one *S. Typhi* specific antigen selected from the group consisting of STY1364 (SEQ ID NO: 1); STY2657 (SEQ ID NO: 2); HCM2.0069c (SEQ ID NO: 3); HCM2.0043 (SEQ ID NO: 4); HCM1.137 (SEQ ID NO: 5); STY2386 (SEQ ID NO: 6); STY1479 (SEQ ID NO: 7); STY2454 (SEQ ID NO: 8); STY2248 (SEQ ID NO: 9); STY3709 (SEQ ID NO: 10); STY2155 (SEQ ID NO: 11); HCM1.213c (SEQ ID NO: 12); and STY0712 (SEQ ID NO: 13);
    one or more 5-120 consecutive amino acid fragments of said selected antigen; or
    any combination thereof.

* * * * *

SEQUENCE LISTING

```
<160> NUMBER OF SEQ ID NOS: 27

<210> SEQ ID NO 1
<211> LENGTH: 141
<212> TYPE: PRT
<213> ORGANISM: Salmonella enterica

<400> SEQUENCE: 1

Met Lys Lys Lys Leu Lys Val Leu Thr Leu Ala Leu Ala Ser Ile Ser
1               5                   10                  15

Ser Val Cys Tyr Ala Ala Met Ala Asp Tyr Asp Thr Tyr Val Ser Asn
            20                  25                  30

Val Gln Ile Asn Asn Leu Ser Tyr Gly Val Tyr Thr Ser Gly Gly Lys
        35                  40                  45

Glu Thr Gln Phe Phe Cys Ile Gly Leu Lys His Gly Ser Glu Ala Ile
    50                  55                  60

Ser Ile Asn Ala Met Cys Lys Val Asp Val Tyr Gly Asn His Lys Gln
65                  70                  75                  80

Gly Phe Asp Asn Met Leu Asn Thr Ala Lys Tyr Tyr Tyr Thr Thr Gly
                85                  90                  95
```

```
Gly Asp Val Arg Ile Tyr Tyr Lys Glu Asn Val Trp Arg Asp Pro Asp
            100                 105                 110

Phe Lys Ser Ala Phe Ser Ser Arg Glu Leu Ile Ala Ile Thr Thr Cys
        115                 120                 125

Ser Ser Ser Ser Tyr Cys Met Gly Pro Thr Val Thr Asn
    130                 135                 140

<210> SEQ ID NO 2
<211> LENGTH: 418
<212> TYPE: PRT
<213> ORGANISM: Salmonella enterica

<400> SEQUENCE: 2

Met Gly Ile Thr Ser Arg Leu Lys Val Met Ser Phe Leu Gln Tyr Phe
1               5                   10                  15

Ile Trp Gly Ser Trp Leu Val Thr Leu Gly Ser Tyr Met Ile Asn Thr
            20                  25                  30

Leu Asp Phe Thr Gly Ala Asn Val Gly Met Val Tyr Ser Ser Lys Gly
        35                  40                  45

Leu Ala Ala Ile Ile Met Pro Gly Ile Met Gly Ile Ile Ala Asp Lys
    50                  55                  60

Trp Leu Arg Ala Glu Arg Ala Tyr Met Leu Cys His Leu Val Cys Ala
65                  70                  75                  80

Gly Ala Leu Leu Tyr Ala Thr Thr Val Thr Asp Pro Gln Thr Met Phe
                85                  90                  95

Trp Val Met Leu Val Asn Ala Met Ala Tyr Met Pro Thr Ile Ala Leu
            100                 105                 110

Ser Asn Ser Val Ser Tyr Ser Cys Leu Ala Lys Ala Gly Gln Asp Pro
        115                 120                 125

Val Thr Ser Phe Pro Pro Val Arg Val Phe Gly Thr Ile Gly Phe Ile
    130                 135                 140

Val Ala Met Trp Thr Val Ser Leu Met Gly Leu Glu Leu Ser Ser Ala
145                 150                 155                 160

Gln Leu Tyr Ile Ala Ser Gly Ala Ser Leu Leu Ala Leu Tyr Ala
                165                 170                 175

Leu Thr Leu Pro Lys Ile Pro Val Ala Glu Lys Lys Ala Asn Thr Thr
            180                 185                 190

Leu Val Ser Lys Leu Gly Leu Asp Ala Phe Val Leu Phe Lys Asn Pro
        195                 200                 205

Arg Met Ala Ile Phe Phe Leu Phe Ala Met Met Leu Gly Ala Val Leu
    210                 215                 220

Gln Ile Thr Asn Val Phe Gly Asn Pro Phe Leu His Asp Phe Ala Arg
225                 230                 235                 240

Asn Pro Glu Phe Ala Asp Ser Phe Val Val Lys Tyr Pro Ser Ile Leu
                245                 250                 255

Leu Ser Val Ser Gln Met Ala Glu Val Gly Phe Ile Leu Thr Ile Pro
            260                 265                 270

Phe Phe Leu Lys Arg Phe Gly Ile Lys Thr Val Met Leu Met Ser Met
        275                 280                 285

Leu Ala Trp Thr Leu Arg Phe Gly Phe Ala Phe Gly Asp Pro Ser
    290                 295                 300

Pro Phe Gly Phe Val Leu Leu Leu Ser Met Ile Val Tyr Gly Cys
305                 310                 315                 320

Ala Phe Asp Phe Phe Asn Ile Ser Gly Ser Val Phe Val Glu Gln Glu
                325                 330                 335
```

```
Val Asp Ser Ser Ile Arg Ala Ser Ala Gln Gly Leu Phe Met Thr Met
            340                 345                 350

Val Asn Gly Val Gly Ala Trp Ile Gly Ser Leu Leu Ser Gly Met Ala
            355                 360                 365

Val Asp Tyr Phe Ser Ile Asp Gly Val Lys Asp Trp Gln Thr Ile Trp
            370                 375                 380

Leu Val Phe Ala Ala Tyr Ala Leu Ala Leu Ala Val Ile Phe Ala Leu
385                 390                 395                 400

Phe Phe Lys Tyr Gln His His Pro Glu Lys Leu Ser Thr Lys Ser Leu
                405                 410                 415

Ala His

<210> SEQ ID NO 3
<211> LENGTH: 524
<212> TYPE: PRT
<213> ORGANISM: Salmonella enterica

<400> SEQUENCE: 3

Met Glu Leu Thr Asp Lys Gln Ile Lys Asp Leu Val Ala Arg Arg His
1               5                   10                  15

Pro Glu Tyr Glu Lys Lys Glu His Trp Asp Phe Leu Ala Ser Thr
            20                  25                  30

Tyr Ala Gly Gly Arg Ala Trp Phe Asn Asp Asn Ile Phe Arg Tyr Phe
            35                  40                  45

Lys Glu Gly Asp Gln Glu Phe Lys Glu Arg Leu Glu Arg Ala Tyr Arg
            50                  55                  60

Phe Asn His Thr Arg Glu Val Val Asn Leu Ile Asn Lys Tyr Leu Phe
65                  70                  75                  80

Lys Glu Val Ile His Arg Asn Thr Asp Glu Ala Pro Glu Gln Ile Arg
                85                  90                  95

Asn Phe Trp Lys Arg Ala Thr Arg Gln Asn Thr Ser Ile Asp Ala Phe
            100                 105                 110

Met Ala Ala Ile Asp Leu Gln Ser Ser Ile Tyr Gly Arg Ile Trp Val
            115                 120                 125

Val Val Asp Ser Thr Met Asn Val Asp Val Glu Ser Ile Ala Asp Glu
            130                 135                 140

Lys Lys Asn Asp Ala Arg Ala Tyr Ala Tyr Trp Ile Ser Pro Gln Gln
145                 150                 155                 160

Leu Leu Asp Val Ala Trp Asp Glu Asp Gly Asn Met Leu Trp Ala Leu
                165                 170                 175

Ile Val Glu Ile Ala Arg Asp Asp Glu Asp Pro Phe Thr Ser Thr Gly
            180                 185                 190

Gln Glu Tyr Gln Arg Tyr Arg Leu Trp Thr Gln Asn Glu Trp Tyr Leu
            195                 200                 205

Phe Arg Glu Glu Val Lys Lys Gly Ser Gly Asn Ser Gly Arg Arg Gln
            210                 215                 220

Ala Lys Val Val Leu Glu Asp Ser Gly Glu His Asn Leu Gly Val Val
225                 230                 235                 240

Pro Val Phe Pro Val Asp Cys Ile Gly Glu Ser Glu Ser Pro Tyr Phe
                245                 250                 255

Ser Pro Ser Leu Ile Asp Asp Ile Ala Tyr Leu Asp Arg Ala Val Ala
            260                 265                 270

Asn Tyr Leu Ser Asn Leu Asp Ala Ile Ile Gln Asp Gln Thr Phe Ser
            275                 280                 285
```

Gln Leu Ala Ile Pro Val Gln Ser Leu Leu Pro Gly Asp Glu Asn His
    290                 295                 300

Thr Lys Val Leu Glu Met Gly Thr Lys Arg Val Phe Thr Phe Asp Ser
305                 310                 315                 320

Glu Ser Gly Asn Gln Pro Phe Tyr Leu Ser Pro Asp Pro Lys Gln Ala
                325                 330                 335

Gln Met Ile Ile Thr Thr Ile Lys Thr Val Ile Asn Glu Ile Tyr His
            340                 345                 350

Ser Val Gly Val Ala Gly Glu Arg Thr Lys Gln Asp Asn Ala Gln Gly
        355                 360                 365

Ile Asp Asn Ser Ser Gly Ala Ala Lys Met Tyr Asp Phe Gln Arg Val
    370                 375                 380

Asn Ser Leu Leu Val Thr Lys Ala Glu Arg Leu Glu Arg Ala Glu Arg
385                 390                 395                 400

Gln Met Met Gln Leu Ala Ala Lys Trp Met Gly Val Glu Leu Asp Glu
                405                 410                 415

Asp His Ser Leu Ile Ala Tyr Pro Glu Ser Phe Asp Ile Arg Gly Leu
            420                 425                 430

Thr Asp Glu Phe Ala Val Ala Glu Lys Leu Ser Leu Leu Gln Ala Pro
        435                 440                 445

Asp Ser Val Arg Arg His Gln Met Glu Met Leu Ile Glu Lys Val Phe
    450                 455                 460

Pro Asn Ile Ser Glu Ala Met Gln Lys Glu Phe Gln Lys Asp Leu Leu
465                 470                 475                 480

Lys Phe Pro Pro Lys Asn Asp Leu Asn Thr Leu Glu Asn Lys Ser Val
                485                 490                 495

Leu Thr Tyr Asp Arg Asp Ala Ala Gln Glu Ser Gly Gln Asp Gln Pro
            500                 505                 510

Arg Gly Asn Gly Asp Ser Ser Thr Gln Glu Thr Glu
        515                 520

<210> SEQ ID NO 4
<211> LENGTH: 351
<212> TYPE: PRT
<213> ORGANISM: Salmonella enterica

<400> SEQUENCE: 4

Met Arg Leu Asn Lys Leu Pro Gly Tyr Gly Leu Pro Glu Leu Ala Phe
1               5                   10                  15

Trp Pro Gln Pro Lys Tyr Glu Arg Asn Glu Trp Ser Ile Tyr Cys Leu
            20                  25                  30

Lys Leu Arg Thr Asp Gly Thr Pro Ala Trp Tyr Arg His Phe Val Asp
        35                  40                  45

Arg Gly Thr Glu Tyr Arg Ala Tyr Gly Asp Asp Tyr Glu Asp Tyr Gln
    50                  55                  60

Thr Ala Lys Glu Arg Ala Leu Glu Leu Asn Lys Ser Val Asp Phe Asn
65                  70                  75                  80

Ile Asp Glu Leu Pro Leu Ser Pro Ala Glu Lys Glu Ser Leu Arg Leu
                85                  90                  95

Lys Val Glu Lys Ala Leu Thr Ala Lys Met Arg Leu Met Asp Glu Glu
            100                 105                 110

His Met Met Phe Asn Glu Ala Val Lys Arg His Ala Lys Ser Pro Arg
        115                 120                 125

Val Ser Ile Glu Glu Leu Ile Leu Lys Pro Asp Asn Glu Asn Leu Arg

-continued

```
                130                 135                 140
Pro Leu Leu Phe Glu Ala Leu Lys Gln Met Pro Tyr Leu His Phe Val
145                 150                 155                 160

Leu Leu Pro Thr Phe Arg Val Tyr Leu Gln Leu Thr Gly Pro Asn Thr
                165                 170                 175

Trp Glu Trp Ser Tyr Ala Gly Ala Arg Glu Ala Lys Ile Gly Tyr Lys
                180                 185                 190

Glu Arg Ile Ala Arg Gly Phe Gly Leu Ser Gly Ala Ala His Trp Gly
                195                 200                 205

Lys Thr Lys Ala Thr Ile Arg Ser Met Leu Leu Pro Gln Ala Asn Lys
210                 215                 220

Leu Leu Gln His Ala Ser Val Lys Arg Met Leu Asp Glu Ala Leu Arg
225                 230                 235                 240

Asn Gly Gln Arg Val Leu Val Ser Gly Asn Phe Val Phe Trp Phe Glu
                245                 250                 255

Asp Lys Asn Gln Ile Gly Trp Ser Val Lys Ala Val Asn Glu Ser Glu
                260                 265                 270

Asn Thr Ser Asn Gly Asn Thr Leu Trp Lys Glu Gly Thr Ile Ile Ser
                275                 280                 285

Lys Asn His Gly Arg Ile Val Val Leu Pro Tyr Thr Lys Glu Asn Gly
                290                 295                 300

Glu His Val Arg Gly Tyr Thr Lys Asn Ala Pro Asn Asp Gly Asn Ala
305                 310                 315                 320

Leu Pro Arg His Lys Asn Glu Tyr Val Glu Leu Pro Phe Glu Val Leu
                325                 330                 335

Glu Gly Asp Leu Met Ile Gly Leu Leu Gly Glu Leu Asn Tyr Glu
                340                 345                 350

<210> SEQ ID NO 5
<211> LENGTH: 251
<212> TYPE: PRT
<213> ORGANISM: Salmonella enterica

<400> SEQUENCE: 5

Met Ala Glu Ile Ala Val Ile Asn His Lys Arg Lys Asn Ser Pro
1                   5                   10                  15

Arg Ile Val Gln Ser Asn Glu Leu Thr Glu Ala Ala Tyr Ser Leu Ser
                20                  25                  30

Arg Asp Gln Lys Arg Leu Leu Tyr Leu Phe Val His Gln Ile Arg Lys
                35                  40                  45

Ser Asp Gly Ser Leu Gln Glu His Asp Gly Ile Cys Glu Ile His Val
                50                  55                  60

Ala Lys Tyr Ala Glu Thr Phe Gly Leu Thr Ser Ala Glu Ala Ser Lys
65                  70                  75                  80

Asp Ile Arg Gln Ala Leu Lys Gly Phe Ala Gly Lys Glu Val Val Phe
                85                  90                  95

Tyr Arg Pro Glu Glu Asp Ala Gly Asp Glu Lys Gly Tyr Glu Ser Phe
                100                 105                 110

Pro Trp Phe Ile Lys Arg Ala His Ser Pro Ser Arg Gly Leu Tyr Ser
                115                 120                 125

Val His Ile Asn Pro Tyr Leu Ile Pro Phe Phe Ile Gly Leu Gln Asn
                130                 135                 140

Arg Phe Thr Gln Phe Arg Leu Ser Glu Thr Lys Glu Ile Thr Asn Pro
145                 150                 155                 160
```

Tyr Ala Met Arg Leu Tyr Glu Ser Leu Cys Gln Tyr Arg Lys Pro Asp
                165                 170                 175

Gly Ser Gly Val Val Ser Leu Lys Ile Asp Trp Ile Met Glu Arg Tyr
            180                 185                 190

Gln Leu Pro Gln Ser Tyr Gln Arg Met Pro Asp Phe Arg Arg Arg Phe
        195                 200                 205

Leu Lys Ala Ser Val Asp Glu Ile Asn Ser Arg Thr Pro Met Arg Leu
    210                 215                 220

Ser Tyr Ile Glu Lys Lys Lys Gly Arg Gln Thr Thr His Ile Val Phe
225                 230                 235                 240

Ser Phe Arg Asp Ile Thr Ser Met Thr Ile Glu
                245                 250

<210> SEQ ID NO 6
<211> LENGTH: 176
<212> TYPE: PRT
<213> ORGANISM: Salmonella enterica

<400> SEQUENCE: 6

Met Gln Val Leu Arg Leu Met Ala Leu Pro Leu Phe Ala Leu Ser Leu
1               5                   10                  15

Ser Val Ser Ile Thr Gly Cys Asp Gln Lys Asn Asp Thr Leu Gln Gly
            20                  25                  30

Lys Gln Asn Asn Met Thr Ala Phe Ile Lys Lys Ile Ala Ala Ser Lys
        35                  40                  45

Glu Ser Glu Glu Thr Gln Arg Tyr Val Gly Asn Leu Asn Gly Ile Glu
    50                  55                  60

Ile Lys Leu Thr Tyr Tyr Tyr Lys Gly Asp Ile Val Leu Arg Gln Ile
65                  70                  75                  80

Ser Glu His Lys Leu Leu Tyr Lys Thr Leu Lys Ala Asn Asn Lys Glu
                85                  90                  95

Glu Ala Gln Lys Met Leu Ser Gln Val Gly Glu Ala Tyr Gln Gly Met
            100                 105                 110

Pro Gly Leu Thr Glu Arg Ile Asp Tyr Tyr Asp Ser Tyr Ala Thr Glu
        115                 120                 125

Tyr Val Asp Ile Asp Phe Thr Gln Ala Lys Ile Ser Asp Leu Cys Lys
    130                 135                 140

Leu Pro Gly Ser Ser Ile Asp Asn Cys Ser Ala Tyr Tyr Leu Ser Met
145                 150                 155                 160

Ile Arg Ser Gln Lys Leu Leu Glu Glu Ser Gly Tyr His Arg Ile Asn
                165                 170                 175

<210> SEQ ID NO 7
<211> LENGTH: 353
<212> TYPE: PRT
<213> ORGANISM: Salmonella enterica

<400> SEQUENCE: 7

Met His Leu Arg His Leu Phe Ser Pro Arg Leu Arg Gly Ser Leu Leu
1               5                   10                  15

Leu Gly Ser Leu Leu Val Ala Ser Ser Phe Ser Thr Leu Ala Ala Glu
            20                  25                  30

Asp Met Leu Arg Lys Ala Val Gly Lys Gly Ala Tyr Glu Met Ala Trp
        35                  40                  45

Ser Gln Gln Glu Asn Ala Leu Trp Leu Ala Thr Ser Gln Ser Arg Lys
    50                  55                  60

Leu Asp Lys Gly Gly Val Val Tyr Arg Leu Asp Pro Val Thr Leu Glu
65                  70                  75                  80

Ile Thr Gln Ala Ile His Asn Asp Leu Lys Pro Phe Gly Ala Thr Ile
                85                  90                  95

Asn Ala Ala Thr Gln Thr Leu Trp Phe Gly Asn Thr Ile Asn Ser Ala
            100                 105                 110

Val Thr Ala Ile Asp Ala Lys Thr Gly Asp Val Lys Gly Arg Leu Val
        115                 120                 125

Leu Asp Ala Arg Lys Arg Thr Glu Glu Val Arg Pro Leu Gln Pro Arg
    130                 135                 140

Glu Leu Val Ala Asp Ala Ala Thr Asn Thr Ile Tyr Ile Ser Gly Val
145                 150                 155                 160

Gly Lys Glu Ser Ala Ile Trp Val Val Asp Gly Glu Thr Ile Lys Leu
                165                 170                 175

Lys Thr Thr Ile Glu Asn Thr Gly Lys Met Ser Thr Gly Leu Ala Leu
            180                 185                 190

Asp Ser Lys Ala Gln Arg Leu Tyr Thr Thr Asn Ala Asp Gly Glu Phe
        195                 200                 205

Ile Thr Ile Asp Thr Ala Ser Asn Lys Ile Leu Ser Arg Lys Lys Leu
    210                 215                 220

Leu Asp Asp Gly Lys Glu His Phe Phe Ile Asn Leu Ser Leu Asp Thr
225                 230                 235                 240

Ala Gly His Arg Ala Phe Ile Thr Asp Ser Lys Ala Thr Glu Val Leu
                245                 250                 255

Val Val Asp Thr Arg Asn Gly Asn Ile Leu Ala Lys Ile Ala Ala Pro
            260                 265                 270

Ala Ser Leu Ala Val Leu Tyr Asn Pro Thr Arg Asn Glu Ala Tyr Val
        275                 280                 285

Thr His Arg Gln Ala Gly Gln Val Ser Val Ile Asp Ala Lys Thr Tyr
    290                 295                 300

Asn Val Val Lys Thr Phe Asp Thr Pro Thr Tyr Pro Asn Ser Leu Ala
305                 310                 315                 320

Leu Ser Ala Asp Gly Lys Thr Leu Tyr Val Ser Val Lys Gln Lys Ser
                325                 330                 335

Thr Arg Glu Gln Glu Ala Thr Gln Pro Asp Asp Val Ile Arg Ile Ala
            340                 345                 350

Leu

<210> SEQ ID NO 8
<211> LENGTH: 341
<212> TYPE: PRT
<213> ORGANISM: Salmonella enterica

<400> SEQUENCE: 8

Met Pro Arg Leu Ser Pro Val Asn Gln Ala Arg Trp Ala Arg Phe Arg
1               5                   10                  15

His Asn Arg Arg Gly Tyr Trp Ser Leu Trp Ile Phe Leu Val Val Phe
                20                  25                  30

Ser Leu Ser Leu Cys Ala Glu Leu Ile Ala Asn Asp Lys Pro Leu Leu
            35                  40                  45

Val Arg Tyr Glu Gly Gln Trp Tyr Phe Pro Leu Val Lys Asn Tyr Ser
        50                  55                  60

Glu Arg Asp Phe Gly Gly Pro Leu Ala Thr Thr Ala Asp Tyr Gln Asp
65                  70                  75                  80

Pro Trp Leu Gln Arg Gln Leu Glu Asn Arg Gly Trp Val Leu Trp Ala
            85                  90                  95

Pro Val Arg Phe Gly Ala Asn Thr Ile Asn Phe Ala Thr Thr Gln Pro
        100                 105                 110

Phe Pro Ser Pro Ser Ala Lys Asn Trp Leu Gly Thr Asp Ala Asn
        115                 120                 125

Gly Gly Asp Val Phe Ala Arg Ile Leu Tyr Gly Thr Arg Ile Ser Ile
130                 135                 140

Leu Phe Gly Leu Met Leu Thr Ile Cys Ser Ser Val Met Gly Val Leu
145                 150                 155                 160

Ala Gly Ala Leu Gln Gly Tyr Tyr Gly Gly Lys Val Asp Leu Trp Gly
                165                 170                 175

Gln Arg Leu Ile Glu Val Trp Ser Gly Met Pro Thr Leu Phe Leu Ile
            180                 185                 190

Ile Leu Leu Ser Ser Val Val Gln Pro Asn Phe Trp Trp Leu Leu Ala
        195                 200                 205

Ile Thr Val Leu Phe Gly Trp Met Ser Leu Val Gly Val Arg Ala
        210                 215                 220

Glu Phe Leu Arg Thr Arg Asn Phe Asp Tyr Ile Arg Ala Ala Gln Ala
225                 230                 235                 240

Leu Gly Val Ser Asp Arg Asp Ile Ile Leu Arg His Met Leu Pro Asn
                245                 250                 255

Ala Met Val Ala Thr Leu Thr Phe Leu Pro Phe Ile Leu Cys Ser Ser
                260                 265                 270

Ile Thr Thr Leu Thr Ser Leu Asp Phe Leu Gly Phe Gly Leu Pro Leu
            275                 280                 285

Gly Ser Pro Ser Leu Gly Glu Leu Leu Leu Gln Gly Lys Asn Asn Leu
290                 295                 300

Gln Ala Pro Trp Leu Gly Ile Ala Ala Phe Leu Ser Val Ala Ile Leu
305                 310                 315                 320

Leu Ser Leu Leu Ile Phe Ile Gly Glu Ala Val Arg Asp Ala Phe Asp
                325                 330                 335

Pro Ala Lys Ala Val
            340

<210> SEQ ID NO 9
<211> LENGTH: 610
<212> TYPE: PRT
<213> ORGANISM: Salmonella enterica

<400> SEQUENCE: 9

Met Arg Tyr Ile Ala Gly Ile Asp Ile Gly Asn Ser Ser Thr Glu Val
1               5                   10                  15

Ala Leu Ala Arg Gln Asp Glu Thr Gly Ala Leu Thr Ile Thr His Ser
            20                  25                  30

Ala Leu Ala Glu Asn Thr Gly Ile Lys Gly Thr Leu Arg Asn Val Phe
        35                  40                  45

Gly Ile Gln Glu Ala Leu Ala Leu Val Ala Lys Arg Ala Gly Ile Asn
    50                  55                  60

Val Ser Asp Ile Ser Leu Ile Arg Ile Asn Glu Ala Thr Pro Val Ile
65                  70                  75                  80

Gly Asp Val Ala Met Glu Thr Ile Thr Glu Thr Ile Ile Thr Glu Ser
                85                  90                  95

Thr Met Ile Gly His Asn Pro Lys Thr Pro Gly Gly Ala Gly Leu Gly
            100                 105                 110

Val Gly Ile Thr Ile Thr Pro Glu Glu Leu Leu Thr Arg Pro Ala Asp
            115                 120                 125

Ser Ser Tyr Ile Leu Val Val Ser Ser Ala Phe Asp Phe Ala Asp Ile
            130                 135                 140

Ala Asn Val Ile Asn Ala Ser Met Arg Ala Gly Tyr Gln Ile Thr Gly
145                 150                 155                 160

Val Ile Leu Gln Arg Asp Asp Gly Val Leu Val Ser Asn Arg Leu Glu
            165                 170                 175

Lys Ser Leu Pro Ile Val Asp Glu Val Leu Tyr Ile Asp Cys Ile Pro
            180                 185                 190

Leu Gly Met Leu Ala Ala Ile Glu Val Ala Val Pro Gly Lys Val Ile
            195                 200                 205

Glu Thr Leu Ser Asn Pro Tyr Gly Ile Ala Thr Val Phe Asn Leu Asn
210                 215                 220

Ala Asp Glu Thr Lys Asn Ile Val Pro Met Ala Arg Ala Leu Ile Gly
225                 230                 235                 240

Asn Arg Ser Ala Val Val Lys Thr Pro Ser Gly Asp Val Lys Ala
            245                 250                 255

Arg Ala Ile Pro Ala Gly Asn Leu Glu Leu Gln Ala Gln Gly Arg Thr
            260                 265                 270

Val Arg Val Asp Val Ala Ala Gly Ala Glu Ala Ile Met Lys Ala Val
            275                 280                 285

Asp Gly Tyr Gly Lys Leu Asp Asn Val Asn Gly Glu Ala Gly Thr Asn
            290                 295                 300

Ile Gly Gly Met Leu Glu His Val Arg Gln Thr Met Ala Glu Leu Thr
305                 310                 315                 320

Asn Lys Pro Ser Ser Glu Ile Phe Ile Gln Asp Leu Leu Ala Val Asp
            325                 330                 335

Thr Ser Val Pro Val Ser Val Thr Gly Gly Leu Ala Gly Glu Phe Ser
            340                 345                 350

Leu Glu Gln Ala Val Gly Ile Ala Ser Met Val Lys Ser Asp Arg Leu
            355                 360                 365

Gln Met Ala Met Ile Ala Arg Glu Ile Glu Gln Lys Leu Asn Ile Asp
            370                 375                 380

Val Gln Ile Gly Gly Ala Glu Ala Glu Ala Ala Ile Leu Gly Ala Leu
385                 390                 395                 400

Thr Thr Pro Gly Thr Thr Arg Pro Leu Ala Ile Leu Asp Leu Gly Ala
            405                 410                 415

Gly Ser Thr Asp Ala Ser Ile Ile Asn Pro Lys Gly Glu Ile Ile Ala
            420                 425                 430

Thr His Leu Ala Gly Ala Gly Asp Met Val Thr Met Ile Ile Ala Arg
            435                 440                 445

Glu Leu Gly Leu Glu Asp Arg Tyr Leu Ala Glu Glu Ile Lys Lys Tyr
450                 455                 460

Pro Leu Ala Lys Val Glu Ser Leu Phe His Leu Arg His Glu Asp Gly
465                 470                 475                 480

Ser Val Gln Phe Phe Pro Thr Pro Leu Pro Pro Ala Val Phe Ala Arg
            485                 490                 495

Val Cys Val Val Lys Pro Asp Glu Leu Val Pro Leu Pro Gly Asp Leu
            500                 505                 510

Ala Leu Glu Lys Val Arg Ala Ile Arg Arg Ser Ala Lys Glu Arg Val
            515                 520                 525

-continued

Phe Val Thr Asn Ala Leu Arg Ala Leu Arg Gln Val Ser Pro Thr Gly
            530                 535                 540

Asn Ile Arg Asp Ile Pro Phe Val Val Leu Val Gly Gly Ser Ser Leu
545                 550                 555                 560

Asp Phe Glu Val Pro Gln Leu Val Thr Asp Ala Leu Ala His Tyr Arg
                565                 570                 575

Leu Val Ala Gly Arg Gly Asn Ile Arg Gly Ser Glu Gly Pro Arg Asn
            580                 585                 590

Ala Val Ala Thr Gly Leu Ile Leu Ser Trp His Lys Glu Phe Ala Tyr
                595                 600                 605

Gly Gln
    610

<210> SEQ ID NO 10
<211> LENGTH: 529
<212> TYPE: PRT
<213> ORGANISM: Salmonella enterica

<400> SEQUENCE: 10

Met Gln Gln Arg Arg Pro Val Arg Arg Ala Leu Leu Ser Val Ser Asp
1               5                   10                  15

Lys Ala Gly Ile Ile Glu Phe Ala Gln Ala Leu Ser Ala Arg Gly Val
            20                  25                  30

Glu Leu Leu Ser Thr Gly Gly Thr Ala Arg Leu Leu Ala Glu Lys Gly
            35                  40                  45

Leu Pro Val Thr Glu Val Ser Asp Tyr Thr Gly Phe Pro Glu Met Met
        50                  55                  60

Asp Gly Arg Val Lys Thr Leu His Pro Lys Val His Gly Gly Ile Leu
65                  70                  75                  80

Gly Arg Arg Gly Gln Asp Asp Ala Ile Met Glu Gln His His Ile Ala
                85                  90                  95

Pro Ile Asp Met Val Val Val Asn Leu Tyr Pro Phe Ala Glu Thr Val
            100                 105                 110

Ala Arg Glu Gly Cys Ser Leu Ala Asp Ala Val Glu Asn Ile Asp Ile
        115                 120                 125

Gly Gly Pro Thr Met Val Arg Ser Ala Ala Lys Asn His Lys Asp Val
130                 135                 140

Ala Ile Val Val Lys Ser Ser Asp Tyr Asp Ala Ile Ile Lys Glu Met
145                 150                 155                 160

Asp Ala Asn Glu Gly Ser Leu Thr Leu Asp Thr Arg Phe Asp Leu Ala
            165                 170                 175

Ile Lys Ala Phe Glu His Thr Ala Ala Tyr Asp Ser Met Ile Ala Asn
        180                 185                 190

Tyr Phe Gly Ser Met Val Pro Ala Tyr His Gly Glu Ser Lys Glu Ala
        195                 200                 205

Ala Gly Arg Phe Pro Arg Thr Leu Asn Leu Asn Phe Ile Lys Lys Gln
        210                 215                 220

Asp Met Arg Tyr Gly Glu Asn Ser His Gln Gln Ala Ala Phe Tyr Ile
225                 230                 235                 240

Glu Glu Asn Val Lys Glu Ala Ser Val Ala Thr Ala Gln Gln Ile Gln
            245                 250                 255

Gly Lys Ala Leu Ser Tyr Asn Asn Ile Ala Asp Thr Asp Ala Ala Leu
        260                 265                 270

Glu Cys Val Lys Glu Phe Asn Glu Pro Ala Cys Val Ile Val Lys His
    275                 280                 285

Ala Asn Pro Cys Gly Val Ala Val Ser Thr Ser Ile Leu Asp Ala Tyr
        290                 295                 300

Asp Arg Ala Tyr Lys Thr Asp Pro Thr Ser Ala Phe Gly Gly Ile Ile
305                 310                 315                 320

Ala Phe Asn Arg Glu Leu Asp Ala Glu Thr Ala Gln Ala Ile Ile Ser
                325                 330                 335

Arg Gln Phe Val Glu Val Leu Ile Ala Pro Ser Ala Ser Glu Glu Ala
            340                 345                 350

Leu Lys Ile Thr Ser Ala Lys Gln Asn Val Arg Val Leu Thr Cys Gly
        355                 360                 365

Gln Trp Ala Ser Arg Val Pro Gly Leu Asp Phe Lys Arg Val Asn Gly
370                 375                 380

Gly Leu Leu Val Gln Asp Arg Asp Leu Gly Met Val Ser Glu Ala Glu
385                 390                 395                 400

Leu Arg Val Val Ser Lys Arg Gln Pro Thr Glu Gln Glu Leu Arg Asp
                405                 410                 415

Ala Leu Phe Cys Trp Lys Val Ala Lys Phe Val Lys Ser Asn Ala Ile
            420                 425                 430

Val Tyr Ala Lys Glu Asn Met Thr Ile Gly Ile Gly Ala Gly Gln Met
        435                 440                 445

Ser Arg Val Tyr Ser Ala Lys Ile Ala Ser Ile Lys Ala Ala Asp Glu
450                 455                 460

Gly Leu Glu Val Lys Gly Ser Ala Met Ala Ser Asp Ala Phe Phe Pro
465                 470                 475                 480

Phe Arg Asp Gly Ile Asp Ala Ala Ala Val Gly Val Ser Cys Val
                485                 490                 495

Ile Gln Pro Gly Gly Ser Ile Arg Asp Asp Glu Val Ile Ala Ala Ala
            500                 505                 510

Asp Glu His Gly Ile Ala Met Ile Phe Thr Asp Met Arg His Phe Arg
        515                 520                 525

His

<210> SEQ ID NO 11
<211> LENGTH: 218
<212> TYPE: PRT
<213> ORGANISM: Salmonella enterica

<400> SEQUENCE: 11

Met Ile Asn Val Leu Leu Val Asp Asp His Glu Leu Val Arg Ala Gly
1               5                   10                  15

Ile Arg Arg Ile Leu Glu Asp Ile Lys Gly Ile Lys Val Val Gly Glu
            20                  25                  30

Ala Cys Cys Gly Glu Asp Ala Val Lys Trp Cys Arg Thr Asn Ala Val
        35                  40                  45

Asp Val Val Leu Met Asp Met Asn Met Pro Gly Ile Gly Gly Leu Glu
    50                  55                  60

Ala Thr Arg Lys Ile Ala Arg Ser Thr Ala Asp Ile Lys Val Ile Met
65                  70                  75                  80

Leu Thr Val His Thr Glu Asn Pro Leu Pro Ala Lys Val Met Gln Ala
                85                  90                  95

Gly Ala Ala Gly Tyr Leu Ser Lys Gly Ala Ala Pro Gln Glu Val Val
            100                 105                 110

Ser Ala Ile Arg Ser Val Tyr Ser Gly Gln Arg Tyr Ile Ala Ser Asp
        115                 120                 125

Ile Ala Gln Gln Met Ala Leu Ser Gln Ile Glu Pro Ala Lys Thr Glu
            130                 135                 140

Thr Pro Phe Ala Ser Leu Ser Glu Arg Glu Leu Gln Ile Met Leu Met
145                 150                 155                 160

Ile Thr Lys Gly Gln Lys Val Asn Glu Ile Ser Glu Gln Leu Asn Leu
                165                 170                 175

Ser Pro Lys Thr Val Asn Ser Tyr Arg Tyr Arg Met Phe Ser Lys Leu
                180                 185                 190

Asn Ile His Gly Asp Val Glu Leu Thr His Leu Ala Ile Arg His Gly
            195                 200                 205

Leu Cys Asn Ala Glu Thr Leu Thr Ser Gln
        210                 215

<210> SEQ ID NO 12
<211> LENGTH: 234
<212> TYPE: PRT
<213> ORGANISM: Salmonella enterica

<400> SEQUENCE: 12

Met Asn Pro Phe Lys Gly Arg His Phe Gln Arg Asp Ile Ile Leu Trp
1               5                   10                  15

Ala Val Arg Trp Tyr Cys Lys Tyr Gly Ile Ser Tyr Arg Glu Leu Gln
            20                  25                  30

Glu Met Leu Ala Glu Arg Gly Val Asn Val Asp His Ser Thr Ile Tyr
        35                  40                  45

Arg Trp Val Gln Arg Tyr Ala Pro Glu Met Glu Lys Arg Leu Arg Trp
50                  55                  60

Tyr Trp Arg Asn Pro Ser Asp Leu Cys Pro Trp His Met Asp Glu Thr
65                  70                  75                  80

Tyr Val Lys Val Asn Gly Arg Trp Ala Tyr Leu Tyr Arg Ala Val Asp
                85                  90                  95

Ser Arg Gly Arg Thr Val Asp Phe Tyr Leu Ser Ser Arg Arg Asn Ser
            100                 105                 110

Lys Ala Ala Tyr Arg Phe Leu Gly Lys Ile Leu Asn Asn Val Lys Lys
        115                 120                 125

Trp Gln Ile Pro Arg Phe Ile Asn Thr Asp Lys Ala Pro Ala Tyr Gly
130                 135                 140

Arg Ala Leu Ala Leu Leu Lys Arg Glu Gly Arg Cys Pro Ser Asp Val
145                 150                 155                 160

Glu His Arg Gln Ile Lys Tyr Arg Asn Asn Val Ile Glu Cys Asp His
                165                 170                 175

Gly Lys Leu Lys Arg Ile Ile Gly Ala Thr Leu Gly Phe Lys Ser Met
            180                 185                 190

Lys Thr Ala Tyr Ala Thr Ile Lys Gly Ile Glu Val Met Arg Ala Leu
        195                 200                 205

Arg Lys Gly Gln Ala Ser Ala Phe Tyr Tyr Gly Asp Pro Leu Gly Glu
210                 215                 220

Met Arg Leu Val Ser Arg Val Phe Glu Met
225                 230

<210> SEQ ID NO 13
<211> LENGTH: 292
<212> TYPE: PRT
<213> ORGANISM: Salmonella enterica

<400> SEQUENCE: 13

```
Met Ser Asp Asp Asn Ser His Ser Ser Asp Thr Val Asn Ser Lys Lys
1               5                   10                  15

Gly Phe Phe Ser Leu Leu Leu Ser Gln Leu Phe His Gly Glu Pro Lys
                20                  25                  30

Asn Arg Asp Glu Leu Leu Ala Leu Ile Arg Asp Ser Gly Gln Asn Glu
            35                  40                  45

Leu Ile Asp Glu Asp Thr Arg Asp Met Leu Glu Gly Val Met Asp Ile
    50                  55                  60

Ala Asp Gln Arg Val Arg Asp Ile Met Ile Pro Arg Ser Gln Met Ile
65                  70                  75                  80

Thr Leu Lys Arg Asn Gln Thr Leu Asp Glu Cys Leu Asp Val Ile Ile
                85                  90                  95

Glu Ser Ala His Ser Arg Phe Pro Val Ile Ser Glu Asp Lys Asp His
            100                 105                 110

Ile Glu Gly Ile Leu Met Ala Lys Asp Leu Leu Pro Phe Met Arg Ser
    115                 120                 125

Asp Ala Glu Ala Phe Ser Met Asp Lys Val Leu Arg Thr Ala Val Val
130                 135                 140

Val Pro Glu Ser Lys Arg Val Asp Arg Met Leu Lys Glu Phe Arg Ser
145                 150                 155                 160

Gln Arg Tyr His Met Ala Ile Val Ile Asp Glu Phe Gly Val Ser
            165                 170                 175

Gly Leu Val Thr Ile Glu Asp Ile Leu Glu Leu Ile Val Gly Glu Ile
            180                 185                 190

Glu Asp Glu Tyr Asp Glu Glu Asp Ile Asp Phe Arg Gln Leu Ser
            195                 200                 205

Arg His Thr Trp Thr Ile Arg Ala Leu Ala Ser Ile Glu Asp Phe Asn
    210                 215                 220

Asp Ala Phe Gly Thr His Phe Ser Asp Glu Glu Val Asp Thr Ile Gly
225                 230                 235                 240

Gly Leu Val Met Gln Ala Phe Gly His Leu Pro Ala Arg Gly Glu Thr
            245                 250                 255

Ile Asp Ile Asp Gly Tyr Gln Phe Lys Val Ala Met Ala Asp Ser Arg
            260                 265                 270

Arg Ile Ile Gln Val His Val Arg Ile Pro Asp Asp Ser Pro Gln Pro
    275                 280                 285

Lys Leu Asp Glu
    290

<210> SEQ ID NO 14
<211> LENGTH: 426
<212> TYPE: DNA
<213> ORGANISM: Salmonella enterica

<400> SEQUENCE: 14
atgaaaaaga aattaaaggt tctgactctt gctcttgcgt caatatccag tgtttgttat    60
gcagctatgg ctgattatga tacgtatgtg agtaatgttc agattaacaa cctgtcttat   120
ggtgtgtata cgtcaggggg taaggaaact cagtttttt gtatcggact gaagcacggg   180
agtgaagcta ttagtatcaa tgccatgtgt aaagtggatg tgtacgggaa tcataaacag   240
gggtttgata acatgctaaa tacagcaaag tattattata caacaggggg ggatgtaagg   300
atatattata aagagaatgt ttggcgcgac cccgatttca aaagtgcatt ctcttccagg   360
gaattaattg cgataactac ttgtagctca tcaagttatt gtatgggcc tacggtgaca   420
``` aattaa                                                                426

<210> SEQ ID NO 15
<211> LENGTH: 1257
<212> TYPE: DNA
<213> ORGANISM: Salmonella enterica

<400> SEQUENCE: 15
atgggtatta cgtcccgctt aaaagtcatg tcgttcttgc aatatttat  ctgggggagc    60 tggctggtta ccctgggctc ttacatgatc aacactctgg attttaccgg cgcgaatgtc   120
ggtatggtct acagctcaaa aggactggca gcgattatca tgccgggcat tatggggatc   180
attgctgata atggctgcg  cgctgagcga gcctatatgc tttgccatct ggtttgcgcg   240
ggggcgttat tgtacgctac caccgttacc gatccccaga cgatgttctg ggtgatgttg   300
gttaatgcga tggcgtatat gccaacgatt gcattatcca tagcgtttc  gtactcctgt   360 ctggcgaaag caggtcagga tccggtaacg tcatttccgc ccgtgcgcgt tttcggcaca   420
ataggtttta ttgttgcgat gtggacggtg agcctgatgg ggctggaact gagcagtgcg   480
caattataca tcgcttctgg cgcatcgtta ttgctggccc tgtatgcgct gacgttaccg   540
aaaattccgg tagccgagaa gaaggcgaac accacgcttg tcagtaagct cggactggat   600
gcttttgttc tgtttaaaaa tccacgcatg gcaatcttct ttttgtttgc gatgatgttg   660
ggggcggtgc tgcaaattac caatgtcttc ggtaatccgt tcctgcatga ttttgcccgt   720
aatcctgagt ttgccgatag ttttgtggtg aagtatccct ctatcttgct ttcagtttcg   780
cagatggcgg aagtgggctt tatcctcacc attccgttct tccttaaacg ctttggtatt   840
aaaacggtaa tgctgatgag catgctggcg tggacgctgc gtttcggctt ctttgccttt   900
ggcgatccat ccccgtttgg ctttgtgcta ttgctgctgt cgatgattgt ttatggctgc   960
gcatttgatt tcttcaacat ctcagggtca gtatttgtag agcaggaggt ggactcaagt  1020
attcgcgcca gcgcgcaggg gctgtttatg accatggtta acggcgtggg ggcgtggatt  1080
gggtctcttt taagcggtat ggccgtggat tattttttcta ttgatggcgt aaaagattgg  1140
caaaccatct ggctggtttt tgccgcctac gctctggcat tggccgttat ttttgcattg  1200
ttctttaaat atcagcacca tccagaaaaa ctgtcgacca atcattagc  acattaa     1257

<210> SEQ ID NO 16
<211> LENGTH: 1575
<212> TYPE: DNA
<213> ORGANISM: Salmonella enterica

<400> SEQUENCE: 16
atggaattga ctgacaagca aatcaaagac cttgtggcac gacgccaccc tgaatatgag    60
aagaaaaaag aacattggga cttcctcgcc agcacctacg ctggcgggcg tgcctggttc   120
aacgacaata tcttccgtta cttcaaagag gcgatcagg  agttcaaaga gcgcctggaa   180
cgcgcttatc gcttcaacca cactcgtgaa gtggtaaacc tcatcaacaa atacctcttc   240
aaagaggtca ttcaccgcaa cactgatgaa gcgccggagc agatccgcaa tttctggaag   300
cgagccacgc gccagaacac ctccatcgat gcgtttatgg cggctatcga tctgcaatca   360 tccattttatg gccgtatctg ggttgtcgtg gacagcacca tgaacgtcga tgttgagtct   420
attgcagacg agaagaaaaa tgatgcgcgt gcctacgctt actggattc  gccacagcag   480 ctgcttgatg ttgcctggga tgaagacggc aatatgttgt gggcgctgat tgttgaaatc   540

```
gcgcgcgacg acgaagatcc gttcacgtca accgggcagg aataccagcg ttaccgtctg      600
tggacgcaaa acgagtggta tctgttccgt gaagaagtga agaaaggttc cggaaatagc      660
ggtcgtcgtc aggccaaagt cgttctggag gatagcggcg agcataatct tggcgtggtg      720
ccggtgttcc cggtggattg cattggtgaa agcgagtctc cgtatttcag tccgtcgttg      780
attgacgaca tcgcctatct tgaccgcgct gtggccaact acctgtcgaa ccttgacgcg      840
attattcagg atcagacatt cagccagctg gcgatcccgg ttcagtcatt gctgccgggc      900
gatgaaaacc acaccaaagt gctcgaaatg ggacaaaac gcgtcttcac cttcgactct      960
gagagcggta atcagccatt ctacctgtct ccagacccga acaggctca gatgatcatc     1020 accacgatta agacggtgat taacgagatc taccattccg ttggtgtggc aggtgagcga     1080
accaagcagg ataacgcaca gggcatcgat aactcttcgg gcgcagcgaa gatgtacgac     1140
ttccagcgcg ttaacagtct gctggtgaca aaagcagagc gcctcgaaag gcagagcgg     1200 cagatgatgc aactggcagc gaaatggatg ggtgtcgaac tggatgaaga ccactctctg     1260
attgcgtacc cggaaagttt cgacattcgc ggtctgactg acgaatttgc cgttgctgag     1320
aaactgtctc tgctccaggc gcctgattct gttcgtcgtc atcagatgga aatgctcatc     1380
gagaaggtct tcccgaacat ttccgaggcg atgcaaaagg aatttcaaaa agatctcttg     1440
aaatttcctc caaaaaatga tcttaatacc cttgaaaata agtcagtact tacttatgat     1500
cgagatgcgg cccaagaaag cgggcaagat caaccccgag ggaatgggga ctcatctact     1560
caagagaccg agtga                                                     1575
```

<210> SEQ ID NO 17
<211> LENGTH: 1056
<212> TYPE: DNA
<213> ORGANISM: Salmonella enterica

<400> SEQUENCE: 17

```
atgcgcttga ataaacttcc cggatatggt cttcctgagc tggctttctg gccgcaaccc       60
aaatacgaaa gaaatgagtg gtcgatttat tgcctgaagc ttcgcactga cggaactccg      120
gcctggtaca gacatttcgt cgatagaggt acagaatacc gcgcatatgg tgacgactat      180
gaggattacc aaaactgcgaa agaaagagca ttggagttga caagagcgt agatttcaat      240 attgatgaac ttcctctctc cccagcagaa aaagagtcat tacgcttaaa agtgaaaaag      300
gccctcaccg cgaaaatgcg actgatggat gaggaacata tgatgttcaa tgaagccgtc      360
aagagacacg ccaaatctcc ccgagtttca atagaagagt taattctaaa acctgataac      420
gagaacctac gtccacttct ttttgaagca ctaaaacaga tgccatatct gcattttgtt      480
cttcttccta ccttccgcgt atatcttcaa ctcacagggc ctaatacttg ggaatggtcg      540
tatgccggag caagagaagc aaaaatcggt tacaaggagc gtattgccag aggttttggt      600
ttatcaggag cggcccattg gggtaaaacc aaggcaacta ttcgctcaat gctgctgccg      660
caagccaata agctgctaca gcatgccagc gtaaaaagaa tgctggatga agctcttcgt      720
aacggccaaa gagttctcgt ctctggaaac tttgttttct ggttcgaaga taagaatcaa      780
attgggtgga gtgttaaagc agtgaacgaa agcgaaaaca cctcaaacgg taatacgctc      840 tggaagaag gaacaatcat ctccaaaaat cacggccgta ttgtcgttct acccttatacg      900 aaggaaaacg gcgagcacgt tagagggtac accaagaacg caccgaatga cggcaatgcg      960
cttccgaggc ataagaatga atacgttgag cttcccttg aagttttgga aggagacctg     1020
atgatcggat tgctcggtga gcttaattac gaataa                              1056
```

<210> SEQ ID NO 18
<211> LENGTH: 756
<212> TYPE: DNA
<213> ORGANISM: Salmonella enterica

<400> SEQUENCE: 18

```
atggcggaaa tagcggttat aaaccataaa aaacgtaaaa atagcccgcg gattgtccag      60
tcaaatgagc tgactgaggc ggcatatagt ctctccaggg atcaaaagcg tctgctgtat     120
ctgttcgttc accagatcag aaaatccgac ggctccctgc aggaacatga cggcatctgc     180
gaaattcacg ttgctaaata cgctgaaaca ttcgggttga cctccgctga agccagtaag     240
gatatacgac aggctttaaa aggttttgcg ggtaaggaag tggttttcta tcgccctgaa     300
gaggatgccg gcgatgaaaa agggtatgaa tcctttccct ggtttattaa acgtgcgcac     360
agcccatcaa gagggcttta cagcgtacat atcaacccat atctgattcc cttcttcatc     420
gggttacaga accggtttac gcagttccgg ctcagtgaaa caaaagagat taccaatccg     480
tacgccatgc gtttatacga atctctgtgc cagtaccgta aacctgatgg ctcaggtgtc     540
gtgtccctga aatcgactg gatcatgaaa cgctaccagc tacctcaaag ttaccagcgt     600
atgccggact ttcgccgccg tttcctgaag gcaagtgttg acgagatcaa cagccggaca     660
ccaatgcgcc tttcttacat cgagaaaaag aaaggccgcc agacgacgca tatcgtattt     720
tccttccgtg atataacctc catgacgatt gaatag                              756
```

<210> SEQ ID NO 19
<211> LENGTH: 531
<212> TYPE: DNA
<213> ORGANISM: Salmonella enterica

<400> SEQUENCE: 19

```
atgcaggttc tacgtcttat ggcactgcca ctattcgcgc tctctctatc ggttagcata      60
actggctgcg atcagaaaaa cgatactctc cagggaaagc aaaataacat gacagcgttt     120
atcaagaaga tagccgctag caaagagtca gaggaaacac aacgctatgt aggtaatctc     180
aacggtattg aaatcaagtt aacctattac tacaaagggg atatcgtttt acgtcaaata     240
tctgaacata aactacttta taagaccctg aaagccaata ataaagaaga agcacaaaaa     300
atgctgagtc aagtcggcga agcttatcag ggtatgccgg gtttgactga acgaatcgac     360
tattatgata gctatgctac ggaatatgtg gatattgatt ttacccaggc aaaaataagc     420
gacctctgta aattgccagg atcatcaatt gacaactgtt ccgcgtacta tctgtcaatg     480
attcgctcgc agaaactgtt ggaagagagc gggtatcata gaatcaatta g              531
```

<210> SEQ ID NO 20
<211> LENGTH: 1062
<212> TYPE: DNA
<213> ORGANISM: Salmonella enterica

<400> SEQUENCE: 20

```
atgcacttac gtcatctttt ttcgccgcgc ctgcgtggtt ctttattgtt aggttcgctc      60
ctcgtcgcat cctcatttag cacgctggcg gcggaagaca tgctgcgtaa agcggtaggc     120
aaaggcgctt atgagatggc ctggagtcag caagaaaacg cgctctggct ggctacatcg     180
caaagccgta aactggataa aggcggcgta gtttatcgtc tcgacccggt gacgctggaa     240
atcacgcaag cgattcataa cgatctcaag ccgttcggcg ccaccatcaa tgccgcgacc     300
```

```
caaacgctgt ggtttggcaa taccattaac agcgcagtta ccgcgattga tgccaaaacg      360
ggtgatgtaa aaggtcgtct ggtacttgat gcgcgcaaac gtactgaaga ggttcgtccg      420
ttacagcccc gtgagctggt tgccgatgcg gcgaccaaca cgatctacat tagcggtgtt      480
ggtaaagaga gtgctatttg gtagtggat ggcgaaacca tcaaactgaa aacgacgatc       540
gaaaataccg gcaaaatgag tacgggtctg gcgctcgaca gtaaagcaca acgcctgtac      600
accaccaatg cggatggcga atttatcacc atcgataccg ccagcaataa aattctcagt      660
cgtaagaagt tgctggatga cggtaaagaa cacttcttta ttaatctgag tctcgatacc      720
gcaggtcatc gcgcgtttat caccgactcg aaggcaactg aggttctggt tgtcgatacc      780
cgtaatggca atattcttgc caaaatcgcg gcgcctgcct ctttggccgt cctgtataat      840
ccgacacgta acgaggcgta tgtgacgcac cgtcaggcag ggcaggtcag cgtgatcgat      900
gcgaagacct ataacgttgt aaaacgttc gatacgccga cgtacccgaa tagcctggcg       960
ctatcggcag acggtaaaac gctctacgtc agcgtgaagc agaaatcgac acgtgaacaa     1020
gaagcgacgc agccggatga tgttattcgc attgctctgt aa                        1062

<210> SEQ ID NO 21
<211> LENGTH: 1026
<212> TYPE: DNA
<213> ORGANISM: Salmonella enterica

<400> SEQUENCE: 21
atgccgcgat taagcccggt caatcaggcc cgctgggcgc gtttccgcca taatcgccgg       60
ggctactggt cactatggat tttcctggta gtgttcagcc tgagcttatg cgcggaactg      120
attgctaacg ataagccatt gctggtgcgc tatgaaggcc agtggtattt ccgctggta      180 aaaaattaca gcgagcgcga tttcggcggc ccgctggcga caacggcaga ctatcaggac      240
ccctggctac aacggcagct tgagaatcgg ggctgggtgt tgtgggcccc cgtacgcttt      300
ggcgccaata ccattaattt tgccaccacg cagcctttcc cctccccgcc ttcggcgaaa      360
aactggctgg gcaccgatgc gaatggcggc gacgttttcg cccgcatcct gtacggcacc      420
cgcatttcta tttttatttgg cctgatgtta acgatttgct ccagcgtcat gggtgtactg      480
gcgggcgcgc tacagggcta ttatggcggc aaagtcgatt tatggggca acgtctcatc      540 gaagtctggt cggggatgcc gaccctgttt ctgattattt tactttccag cgtagtgcag      600
cctaacttct ggtggctgct ggccataacc gtgctgtttg gctggatgag tctggtgggc      660
gtggtgcgcg ccgagttttt acggaccccg aatttttgact atatccgcgc cgcgcaggcg      720
cttggcgtca gcgatcgtga cattatcctg cgccatatgt tgcctaatgc gatggtcgct      780
accctgacat tttaccgtt catttttatgt agttccatca ccaccctgac gtcgctggat      840
tttctgggat tcggtctgcc gcttggctcc ccttctctcg gcgaacttct tttacagggg      900
aaaaacaact tacaggctcc ctggctgggg atcgccgcct ttctgtctgt cgccattctg      960
ctatcgctgc tgattttat cggcgaagcg gtacgcgacg cctttgatcc tgctaaggcg     1020
gtataa                                                               1026

<210> SEQ ID NO 22
<211> LENGTH: 1833
<212> TYPE: DNA
<213> ORGANISM: Salmonella enterica

<400> SEQUENCE: 22
atgcgatata tagctggcat tgacatcggt aactcatcaa cggaagtcgc actggcgcgg       60
```

| | |
|---|---|
| caagatgaga ctggcgcact aacgattaca cacagcgcgc tggcggaaaa caccgggatc | 120 |
| aaaggcacgt tgcgtaacgt gttcggcatt caggaagcgc tcgccctcgt cgcaaagcgc | 180 |
| gcggggatca atgtcagcga tatttcgctc atccgcatta acgaagccac gccggtgatt | 240 |
| ggcgatgtgg cgatggaaac cattaccgaa accatcatca ccgaatcgac aatgatcggc | 300 |
| cataacccaa aaacgccggg cggagcaggc cttggtgtgg gtatcacgat tacgccggag | 360 |
| gagctgttaa cccgcccggc ggactcgtcc tatattctgg tggtatcgtc agcctttgat | 420 |
| tttgctgata tcgccaatgt tatcaacgcc tcaatgcgcg ccggatacca gattaccggc | 480 |
| gtcattttgc agcgcgacga tggcgtactg gtcagcaacc ggctggaaaa atcgctaccg | 540 |
| attgtcgatg aagttctgta catcgactgc attccgctgg ggatgctggc ggcgattgaa | 600 |
| gtcgccgtgc cggaaaaggt tatcgaaacc ctctctaacc cttacggcat cgccaccgta | 660 |
| ttcaacctca acgccgatga gacgaaaaac atcgtcccga tggcgcgcgc gctgattggc | 720 |
| aaccgttccg ccgtggtggt taaaacgcca tccggcgacg tcaaagcgcg cgcaataccc | 780 |
| gccggtaacc tggagctgca ggctcagggt cgtaccgtgc gcgtggatgt tgccgccggt | 840 |
| gccgaagcta tcatgaaagc ggtggacggc tacggcaagc tcgacaacgt caacggcgag | 900 |
| gccgggacca atatcggcgg catgctggag catgtgcgcc agaccatggc cgagctaacc | 960 |
| aataagccga gcagcgagat tttcattcag gatcttctgg ccgttgacac ctcggttccg | 1020 |
| gtgagcgtca ccggcggtct ggccggggag ttctcgctgg agcaggccgt cggcatcgcc | 1080 |
| tcgatggtga atcagaccg tctgcaaatg gcgatgattg cccgtgaaat tgagcagaag | 1140 |
| cttaatatcg acgtgcagat cggcggcgct gaggctgaag ccgccattct gggcgcgctg | 1200 |
| accacgccgg gtaccacccg accgctggcg atcctcgacc tcggcgcggg ctccaccgat | 1260 |
| gcctccatca tcaaccctaa aggtgaaatc atcgccaccc atctcgccgg ggcaggcgac | 1320 |
| atggtcacga tgattattgc ccgcgaactg gggctggaag accgctatct ggcggaagag | 1380 |
| atcaaaaaat accccgctggc taaggtcgaa agcctgttcc acttacgcca cgaggacggc | 1440 |
| agcgtccagt tcttcccgac gccgctgcct cctgcggtgt cgcccgcgt ctgcgtggtg | 1500 |
| aaaccggacg aactggtgcc gcttcccggc gacttagcgc tggaaaaagt gcgcgccatt | 1560 |
| cgccgcagcg ctaaagaacg cgtctttgtc accaacgccc tgcgcgcgct gcgtcaggtc | 1620 |
| agtccaaccg gcaacattcg cgatattccg ttcgtggtgc tggtcggcgg ctcgtcgctg | 1680 |
| gatttcgaag ttccgcagtt ggtcaccgat gcgctggcgc actaccgcct agtcgccggg | 1740 |
| cgaggaaata ttcgcggcag cgaaggccca agaaacgcgg tggccaccgg tctgattctc | 1800 |
| tcctggcaca aggagtttgc atatggacag taa | 1833 |

<210> SEQ ID NO 23
<211> LENGTH: 1590
<212> TYPE: DNA
<213> ORGANISM: Salmonella enterica

<400> SEQUENCE: 23

| | |
|---|---|
| atgcaacaac gtcgtccagt ccgccgcgct ttgctcagtg tttctgacaa ggccggtatc | 60 |
| atcgaattcg cccaggcact ttccgcacgc ggtgtggagc tgctgtctac gggggcacc | 120 |
| gcccgcctgt tagcagaaaa aggcctgccg gtgaccgaag tttccgatta caccggtttc | 180 |
| ccggaaatga tggatggacg cgtaaagacc ctgcatccaa agtacacgg tggcatcctc | 240 |
| ggtcgtcgcg gtcaggacga tgccattatg gaacagcacc acatcgcccc tatcgatatg | 300 |

```
gttgtcgtta acctatatcc gttcgccgaa accgtggcac gcgaaggctg ctcgctggca    360
gatgcagtag agaacattga tatcggcggc ccgaccatgg tgcgctctgc tgctaagaac    420
cataaagacg tcgccatcgt ggtgaagagc agcgactacg acgccattat taaagagatg    480
gatgctaacg aaggttctct gaccctcgac acccgtttcg atctcgcgat taaagccttc    540
gaacacaccg ccgcctacga cagcatgatc gccaactact tcggcagcat ggttccggcc    600
taccacggtg aaagcaaaga agccgccggt cgcttcccgc gtacgctgaa cctgaacttc    660
attaagaagc aggatatgcg ctacggcgag aacagccacc agcaggctgc cttctatata    720
gaagagaatg tgaaagaagc atccgttgcc accgcacagc agattcaggg caaagcgctc    780
tcttataaca atatcgccga taccgatgcg gcgctggaat gcgtgaaaga gttcaacgag    840
ccagcctgcg tgatcgtcaa gcacgccaac ccgtgcggcg tggcggtaag tacctcgatt    900
ctcgatgctt atgaccgtgc gtataaaaca gacccgacct ccgcgttcgg cggcattatc    960
gccttcaacc gcgagctgga tgccgaaacc gcgcaggcca tcatctcccg tcagttcgtg   1020
gaagtgctca tcgccccatc cgcaagcgaa gaagcgctga aaatcacctc agccaagcag   1080
aacgtccgtg ttctgacctg cggccaatgg gcaagccgcg ttccgggcct ggatttcaaa   1140
cgcgttaacg gcggtctgct ggttcaggac agggatctgg gtatggtgag cgaagctgaa   1200
ctgcgcgtgg tgtccaaacg ccagccgacc gagcaggaac tgcgcgatgc gctgttctgc   1260
tggaaggtag ccaagttcgt gaaatccaac gccattgtgt atgccaaaga gaacatgact   1320
atcggcatag gcgcaggcca gatgagccgc gtgtactccg cgaaaatcgc tagcattaaa   1380
gcggctgacg aaggtctgga agtgaaaggc tctgctatgg cttccgacgc gttcttcccg   1440
ttccgtgatg gcattgatgc cgctgccgct gtcggcgtga gctgcgttat ccagcctggc   1500
ggttctatcc gtgatgatga agtcattgcc gccgccgacg aacacggcat tgcgatgatc   1560
ttcaccgaca tgcgccactt ccgccattaa                                    1590

<210> SEQ ID NO 24
<211> LENGTH: 657
<212> TYPE: DNA
<213> ORGANISM: Salmonella enterica

<400> SEQUENCE: 24
ttgatcaacg ttcttcttgt tgatgaccac gaactggtgc gcgcagggat acgacgcatt     60
cttgaagata taagggcat taaagttgtc ggtgaagcgt gctgcggaga ggatgcggta    120
aaatggtgcc gtactaacgc cgttgacgtc gtgctgatgg atatgaacat gcccggtatt    180
ggcggccttg aggcgacgcg taaaattgcc cgatcgacag cggatatcaa agtgatcatg    240
ctgaccgtcc atacggagaa cccgttgccc gccaaagtga tgcaggctgg cgcagctggc    300
tatctcagca aaggcgctgc gcctcaggag gtggtgagcg ctattcgttc ggtgtattcc    360
ggacaacgtt atatcgcctc cgatatcgct caacagatgg cgctcagtca gattgagcct    420
gcaaaaacgg aaacgccgtt cgccagtttg tctgaacgcg agttgcagat tatgctgatg    480
atcaccaagg gccagaaggt caatgagatt tcagaacagc tgaatctcag tcctaaaacg    540
gtgaacagct atcgctatcg tatgttcagt aaattaaaca ttcatggtga tgttgagctg    600
actcacctgg caatccgcca tggcctgtgt aatgcggaga cgttaacaag ccagtga      657

<210> SEQ ID NO 25
<211> LENGTH: 705
<212> TYPE: DNA
<213> ORGANISM: Salmonella enterica
```

<400> SEQUENCE: 25

```
atgaacccat tcaaaggccg gcattttcag cgtgacatca ttctgtgggc cgtacgctgg    60
tactgcaaat acggcatcag ttaccgtgag ctgcaggaga tgctggctga acgcggagtg   120
aatgtcgatc actccacgat ttaccgctgg gttcagcgtt atgcgcctga aatggaaaaa   180
cggctgcgct ggtactggcg taacccttcc gatctttgcc cgtggcacat ggatgaaacc   240
tacgtgaagg tcaatggccg ctgggcgtat ctgtaccggg ccgttgacag ccggggccgc   300
actgtcgatt tttatctctc ctcccgtcgt aacagcaaag ctgcataccg gtttctgggt   360
aaaatcctca caacgtgaa gaagtggcag atcccgcgat tcatcaacac ggataaagcg   420
cccgcctatg gtcgcgcgct tgctctgctc aaacgcgaag gccggtgccc gtctgacgtt   480
gaacaccgac agattaagta ccggaacaac gtgattgaat gcgatcatgg caaactgaaa   540
cggataatcg gcgccacgct gggatttaaa tccatgaaga cggcttacgc caccatcaaa   600
ggtattgagg tgatgcgtgc actacgcaaa ggccaggcct cagcatttta ttatggtgat   660
cccctgggcg aaatgcgcct ggtaagcaga gtttttgaaa tgtaa              705
```

<210> SEQ ID NO 26
<211> LENGTH: 879
<212> TYPE: DNA
<213> ORGANISM: Salmonella enterica

<400> SEQUENCE: 26

```
atgagcgacg acaattcaca cagtagtgac acagtaaaca gtaaaaaggg atttttttcc    60
ctgctactca gccagctttt ccacggtgaa cctaaaaacc gtgatgagtt gctggcgctg   120
atccgtgatt ccgggcagaa cgagcttatc gatgaagata cgcgcgatat gctcgaaggc   180
gtaatggaca tcgccgacca gcgcgttcgc gatattatga tcccgcgctc ccagatgatt   240
accctgaaac gcaaccagac gctggacgaa tgtctcgatg ttatcatcga gtccgcccac   300
tcgcgttttc cggtgatcag cgaagataaa gatcacattg aagggattct gatggccaaa   360
gatttgctgc cgtttatgcg cagcgatgcc gaagccttca gcatggacaa agtgttacgt   420
accgcggttg tcgtaccgga aagcaaacgg gttgaccgta tgctcaagga attccgctcc   480
cagcgctacc atatggccat cgttatcgat gagtttggcg gcgtttccgg ccttgtgact   540
atcgaagaca tcctcgaact gattgtcggt gaaattgaag atgagtatga cgaagaagac   600
gatatcgact ccgtcagct tagccgccat acctggacga ttcgcgcgct ggcgtcgatt   660
gaagacttca tgacgctttt cggcacccac ttcagcgatg aagaagtcga taccatcggc   720
gggctggtga tgcaggcgtt cggccattta ccggcccgcg gcgaaaccat tgacattgat   780
ggttaccagt tcaaagtggc aatggccgat agtcgtcgta ttattcaggt gcatgtcagg   840
atcccggatg actcgcccca gccaaaactg gacgaataa              879
```

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
    6xHis tag

<400> SEQUENCE: 27

```
His His His His His His
1               5
```